(12) United States Patent
Walther et al.

(10) Patent No.: US 9,260,498 B2
(45) Date of Patent: Feb. 16, 2016

(54) LEUKOLECTINS AND USES THEREOF

(75) Inventors: Bernt Th. Walther, Bergen (NO); Mirushe Miftari, Bergen (NO)

(73) Assignee: LEUKOLECT AS, Bergen (NO)

( * ) Notice: Subject to any disclaimer, the term of this patent is extended or adjusted under 35 U.S.C. 154(b) by 0 days.

(21) Appl. No.: 13/126,225

(22) PCT Filed: Oct. 29, 2009

(86) PCT No.: PCT/GB2009/002569
§ 371 (c)(1),
(2), (4) Date: Apr. 27, 2011

(87) PCT Pub. No.: WO2010/049688
PCT Pub. Date: May 6, 2010

(65) Prior Publication Data
US 2011/0280882 A1    Nov. 17, 2011

(30) Foreign Application Priority Data

Oct. 29, 2008   (GB) .................................. 0819883.0

(51) Int. Cl.
C07K 14/42      (2006.01)
C07K 14/47      (2006.01)
(52) U.S. Cl.
CPC .................................. C07K 14/4726 (2013.01)
(58) Field of Classification Search
None
See application file for complete search history.

(56) References Cited

U.S. PATENT DOCUMENTS

| 5,607,679 | A | 3/1997 | Rhodes | |
|---|---|---|---|---|
| 2007/0141652 | A1 | 6/2007 | Zheng et al. | |
| 2013/0129742 | A1* | 5/2013 | Walther et al. ............. | 424/139.1 |

FOREIGN PATENT DOCUMENTS

| WO | 94/11497 | 5/1994 |
|---|---|---|
| WO | 99/29836 | 6/1999 |
| WO | 99/62315 | 12/1999 |
| WO | 2004/078140 | 9/2004 |

OTHER PUBLICATIONS

Galliano et al. Structural and biochemical characterization of a new type of lectin RT isolated from carp eggs. Biochem. J. 376:433-440(2003).*
Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Metzler et al. Solution structure of human CTLA-4 and delineation of a CD80/CD86 binding site conserved in CD28. Nat Struct Biol. 4(7):527-531, 1997.*
Bork Powers and pitfalls in sequence analysis: the 70% hurdle. Genome Res. Apr. 2000;10(4):398-400.*
Doerks et al. Protein annotation: detective work for function prediction. Trends Genet. Jun. 1998;14(6):248-50.*
Smith et al. The challenges of genome sequence annotation or "the devil is in the details". 1997, Nature Biotechnology 15:1222-1223.*
Brenner. Errors in genome annotation. 1999, Trends in Genetics 15:132-133.*
Bork et al Go hunting in sequence databases but watch out for the traps. (1996, Trends in Genetics 12:425-427).*
Bowie et al Deciphering the message in protein sequences: tolerance to amino acid substitutions. (1990, Science 247:1306-1310).*
Hagenmaier et al., The hatching process in fish embryos—IV. The enzymological properties of a highly purified enzyme (chorionase) from the hatching fluid of the rainbow trout, Salmo gairdneri rich, Comparative Biochemistry and Physiology 49B:313-324 (1974).
International Search Report for PCT/GB2009/002569 dated Dec. 29, 2009.
Adzhubei, A. et al., Annotated expressed sequence tags (ESTs) from pre-smolt Atlantic salmon (*Salmo salar*) in a searchable data resource, BMC Genomics 2007; 8:209.
Beisel, H. et al., Tachylectin-2: crystal structure of a specific GlcNAc/GalNAc-binding lectin involved in the innate immunity host defense of the Japanese horseshoe crab Tachypleus tridentatus, The EMBO Journal, 1999; 18(9):2313-22.
Galliano, M. et al., Structural and biochemical characterization of a new type of lectin isolated from carp eggs, Biochem J. (2003) 376; 433-440.
Low, D. et al., A novel human tectonin protein with multivalent beta-propeller folds interacts with ficolin and binds bacterial LPS, PLoS One, 2009; 4(7):e6260.
MacGillivray, A. et al., The heterogeneity of mouse-chromatin nonhistone proteins as evidenced by two-dimensional polyacrylamide-gel electrophoresis and ion-exchange chromatography. Eur. J. Biochem., 1974; 41(1):181-90.
Medzhitov, R. et al., Innate immunity: the virtues of a nonclonal system of recognition, Cell, 1997; 91(3):295-8.
Miller, S. et al., A simple salting out procedure for extracting DNA from human nucleated cells, Nucleic Acids Research, 1988; 16(3):1215.
Oppen-Berntsen, D. et al., The effects of hypoxia, alkalinity and neurochemicals on hatching of Atlantic salmon (*Salmo salar*) eggs, Aquaculture, 1990; 86:417-430.
Shapiro, M. et al., RNA splice junctions of different classes of eukaryotes: sequence statistics and functional implications in in gene expression, Nucleic Acids Research, 1987; 15(17):7155-74.
Shigenaga, T. et al., Separation of large and small granules from horseshoe crab (*Tachypleus tridentatus*) hemocytes and characterization of their components, J. Biochem., 1993; 114(3):307-16.
Smulian, A. et al., Expressed sequence tags from Pneumocystis carinii, S24C6 AGS-1 Pneumocystis carinii cDNA 3-, mRNA sequence, Genbank Accession 2000: AW333642.
GenBank Accession No. A8E602, amino acid sequence from Xenopus laevis, dated Nov. 13, 2007.

(Continued)

*Primary Examiner* — Maher Haddad
(74) *Attorney, Agent, or Firm* — Wenderoth, Lind & Ponack, L.L.P.

(57) ABSTRACT

The present invention relates to a polypeptide, described as a lectin, its encoding nucleic acid sequence and antibodies to the polypeptide and their use in various medical applications, particularly for treating or preventing an autoimmune disorder, an inflammatory disorder or damaged skin in an animal.

9 Claims, 35 Drawing Sheets

(56) References Cited

OTHER PUBLICATIONS

Genbank Accession BT047111.1, Leong, J. et al., Salmo salar and Esox lucius full-length cDNA sequences reveal changes in evolutionary pressures on a post-tetraploidization genome, dated Aug. 24, 2010.

GenBank Accession No. DY694834.1, nucleic acid sequence from Salmo salar, dated Nov. 20, 2008.

GenBank Accession No. FJ643619, Mitfari, J. et al., Molecular cloning and characterization of the leukolectin gene isolated from the human leukocytes, *Homo sapien* leukolectin mRNA, complete cds, dated Feb. 14, 2009.

Genbank Accession BT058707, Leong, J. et al., Salmo salar full-length cDNAs, Salmo salar clone, dated Feb. 17, 2009.

GenBank Accession No. ACI66912; Fish-egg lectin. Aug. 24, 2010.

English translation of Russian Decision on Grant, issued in corresponding Russian Patent Application No. 2011121616/10(031987).

\* cited by examiner

FIG. 3B

```
                      170       180       190       200       210       220       230       240
                        |         |         |         |         |         |         |         |
Human/1-255         CWAVNKNDDIYLMSLNQDCQNKGWSHIEGKLSMIEVATDGSVFGVNSAGSVYTRDGITASKPEGTGWSNIFMGMLMGHVT
Salmon/1-255        CWAVNKNDDIYLMSLNQDCQNKGWSHIEGKLSMIEVATDGSVFGVNSAGSVYTRDGITASKPEGTGWSNIPMGMLMGHVT
Salmon/1-208        CWAVNKNDDIYLMSLNQDCQNNGWSHIEGKLSMIEVATDGSVFGVNSAGSVYTRDGITASKPEGTGWSNIPMCMLMGHVT
Chicken/1-196       CWAVNKNDDIYLMSLNQDCQNKGWSHIDGKLSMIEVATDGSVFGVNSAGSVYTRDGITASKPEGTGWSNIFMGMLMGHVT
Cod/1-158           CWAVNKNDDIYLMSLNQDCQNKGWSHIDGKLSMIEVATDGSVFGVNSAGSVYTRD-------------------------

Unigene/ssa23163/
contig1/1-260       CWAVNNNDDIYLMSLNQDCQNNGWSHIEGKLSMIEVATDGSVFGVNSVGSVYTRDGITASKPEGTGWSHVPMCMQMKHVT
Unigene/ssa23163
contig2/1-250       CWAVNKNDDIYLMSLNQDCQNKGWSHIEGKLSMIEVATDGSVFGVNSAGQVYTRDGITASKPEGTGWSNVLMYPMKHVT Conservation        -------7---------9--------------------9--9------3223342332333220111011532

250
                        |
Human/1-255         YDLGRLWVISKSGGTMVCTH
Salmon/1-255        YDLGRLMVVSKSAVTMVCTH
Salmon/1-208        YDLGRLMVVSKSAVTMVCTH
Chicken/1-196       YDLGRLWVV-----------
Cod/1-158           --------------------

Unigene/ssa23163/
contig1/1-250       YDLGRLWVISKSGFTMVCKH
Unigene/ssa23163
Contig2/1-260       YDLGRLWVISNSGFTMVCKH Conservation        342332332-----------
```

FIG. 4A-1

MRATAAVLLVLCLLTISHAWDCQEVVNIKNLMQIDAGLGQVVATDTGRIPYYLVGDKWIRLPGSLKHTVGPAGIW

GVNKDYAIYKYVAGNWVQAAGLLKQLDAGGEQFIVGANMNDTPYRLTSSATVGYKGPGSPLPWTGLPGAVKYY

SCGPFGCWAVNKNDDIYLMSLNQDCQNKGWSHIEGKLSMIEVATDGSVFGVNSAGSVYTRDGITASKPEGTGW

SNIPMGMLMGHVTYDLGRLWVVSKSGGTMVCTH

FIG. 4A-2

MRTTAAFLLVLCLLAISHAWDCQEVVNIKLMQIDAGLGQVVATDTSQIPYYLVGDKWIRLPGSLKHITVGPAGIWGVNKD

YAIYKYVAGNWVQAAGLLKQLDAGGEQFIVGANMNDTPYCLTSSATVGYKGPGSPLPWTGLPGAVKYYSCGPFGCWA

VNKNDDIYLMSLNQDCQNKGWSHIEGKLSMIEVATDGSVFGVNSAGSVYTRDGITASKPEGTGWSNIPMGMLMGHVTY

DLGRLWVVSKSAVTMVCTH

FIG. 4A-3

SIPYYLVGDKWIRLPGSLKHITVGPAGIWGVNKDYAIYKYVAGNWVQAAGLPKQLDAGGEQFIVGANMDTPYCLT

SSATVGYKGPGSSPLPWTGLPGAVKYYSCGPFGCWAVNKNDDIYLMSLNQDCQNKGWSHIEGKLSMIEVATDGSV

FGVNSAGSVYTRDGITASKPEGTGWSNIPMCMLMGHVTYDLGRLWVVSKSAVTMVCTH

FIG. 4A-4

IPYYLVGDKWIRLPGSLKHITVGPAGIWGVNKDYAIYKYVAGNWVQAAGLLKQLDAGGEQFIVGANMDTPYCLTS

SATVGYKGPGSSPLPWTGLPGAVKYYSCGPFGCWAVNKNDDIYLMSLNQDCQNKGWSHIDGKLSMIEVATDGSVF

GVNSAGSVYTRDGITASKPEGTGWSNIPMGMLMGHVTYDLGRLWVV

FIG. 4A-5

LVGDKWIRLPGSLKHITVGPAGIWGVNKDYAIYKYVAGNWVQAAGLLKQLDAGGEQFIVGANMNDTPYCLTSSATVGYKG

PGSPLPWTGLPGAVKYYSCGPFGCWAVNKNDDIYLMSLNQDCQNKGWSHIDGKLSMIEVATDGSVFGVNSAGSVVYTRD

FIG. 4A-6

LDCTVIDGNLKQIDAGSGSVVGVNNLNETFVLIDNVFTKISGSLKHFSVGPAGQLGVNTANNIFKYQSGGFVQLAGL

LKQVDAGGDQIIAGVNMYDDIYCLNMDANNKWPSSNTPWVQINGKLKYYSCGPYSCWGVNSNDQIFIMKDVSSN

VCSGSGSFINIPGLLSMIEVATDGSVFGVNSQGNLYQRTGVTRSKPDGTDWISMVACPNGHKHVSFDLGVLWLVC

VDGSIRKCILTD

FIG. 4A-7

MLILGVLILLGAEASAETLCIPGRMKQLDAGAGRVVAVKSNGDVYQLLENNWVQIPGKLIHVTVGPAGLWGVNKDKN

IYKYVDNDWLQVDGLLNQIDAGGNRFVGVNDNEDIFCLNQDQTTSNAVKLDYKGVDGKLKYYSSGGYGSWGVNA

AYDIFYRRNVHPMSCQGTNWENVEGKLVLEVAEDGSVYGVNYNGHVYYKREGITAGNPMGTSWTYLKVDEKVRHVS

YDRGVLYVYVTIDDRIFRC

FIG. 4A-8

MKVYQGVLLLLSCQILYTLALDCTIMNGNLKQIDAGSGSVVGVNDLNQAFVLQDDVFNPVSKSLKHFSVGPAGQLG

VNKTYYIFKLMSGRFVEFFPGLLKQVDAGGDQIIAGVNMNDDIFCLNMDASNQWPSSTTPWVTINGKLKYYSCGPY

SCWGVNSDDYIFMMKGVSSNACSGGGMFVNIPGLLSMIEVGTDGSVFGVNYEAKLYQRVGVSRSNPAGTDWIS

MIACPNGHKHVSFDLGVLWVVCVDGSIRKCTL

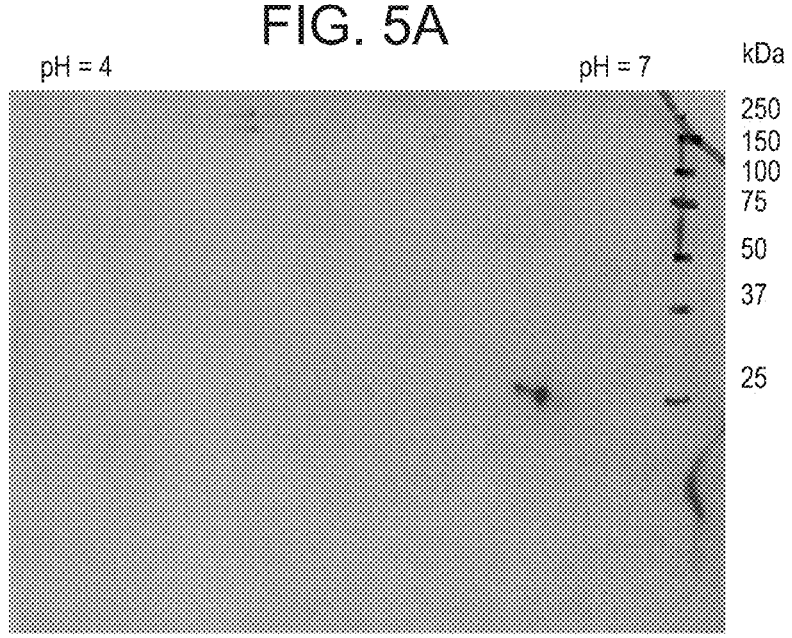
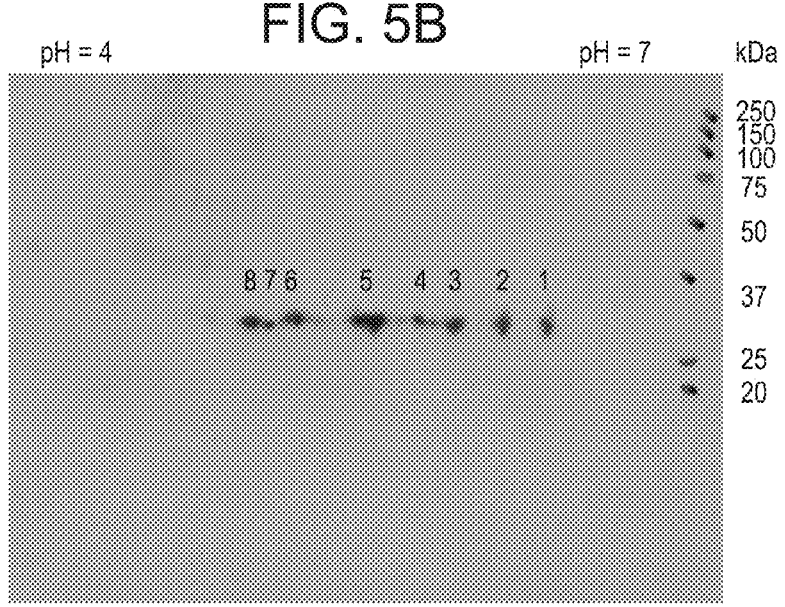

FIG. 9B-1

```
TGTGCAGGGCTATAAAAGCGCAAAGTCTTCCAATGGGACAATTGAAGTCTGGTGTACAAC
CAAACGTATACTGTAGATCTACATAGACATCATGAGAGCCACTGCAGCCGTCCTATTGGT
CCTCTGTCTCCTGACCATCAGTCATGGTAAGTTACCATCATCTGAAACATGCTTGATCAA
CTTGGAGTTGAAGTTTTTCTTGGTATACTCTACTCATATGTCTTTGTCTCCATAGCATGG
GACTGTCAGGAGGTAGTAAACATCAAGAATCTGATGCAGATCGATGCAGGACTGGGGCAA
GTGGTTGCTACGGACACAAGTCAAATCCCCTACTACCTGGTAGGTGATAAATGGATCCGT
CTGCCTGGTTCCCTGAAGCATATCACTGTAGGACCAGCAGGGATCTGGGGTGTCAACAAG
GACTATGCAATCTACAAGTATGTGGCCGGTAACTGGGTCAAGCTGCAGGTAAGTGGAGA
GCATTACTCAATATTTATCCAGAGGACACCTGCTTATTAGCTTTCCTGATACCATCAGGC
TGTTGAAAAAACGATTGATGTTTTAAATTGTAACTTGTAGGTAATTTGGCAGTACTCCT
TGTTTGCTTGTCTGTCTGTCTTTGTGGTCTTGGCCTTCTGAAACAGTTGGATGCTGGAGG
TGAACAGTTTATTGTGGGGCTAACATGAACGATACTCCATACTGTCTGACAAGTAGTGC
CACAGTTGGCTACAAGGGTCCAGGCTCACCCCTTCCATGGACAGGATTGCCAGGAGCTGT
GAAGTACTACAGCTGCGGACCCTTTGGGTGCTGGGCAGTCAACAAGAATGATGATATCTA
CTTAATGAGTGTAAGATCTGGGAAAGAGTGGGAGAGCTGGAGTAGAGTAGTAGAGGATGG
AGAGTGTCAGTTATTTTAAAACTGTTTCATATTATAACTGTTGAAATTGTCCTAAAACCC
TGATTGTATCATTTTGTTTCCAGCTGAATCAAGACTGCCAAAACAAGGGGTGGAGTCACA
TTCAAGGCAAGCTTTCCATGATTGAGGTGGCAACTGATGGTAGTGTCTTTCGGGTCAACT
CTGCGGGTAGTGTTTATACCCAGGTAAGGTTGCTACTGAACTATGTGTATGGTCCACCAC
CCCCCCCCCCCAACAGTATTAACTTGAAAATGACTTGTAATAATAACTTAGAATAATAA
TGGTATACCCTTTAATTATAACTCTGATCCTTACAGTACATGCTATGTGAATCTCCTTAC
ACAAAAACTAAATATTGTAGGTACATAAATAAAATCAGTTAAATATAATCAGATCTAAAC
TTATAGGACTTATTAAGAAATGTGTAGACAGTGTATGATAAAATATGTAAAAGTTGGATG
TCCTGTAAAGCTACAGTTTGGGATAAAAAACAACAACTTCCCAGACACCCCACCACTTGT
TCTGGTAAACAGCTGAGGAATGTAGTTAGAGAAATGTAACCACTCTCACATTCATACATG
GAGCTACGGATGCAAAGACACAACAATTTTTTTATTAAAAAAAAAAAAATGTTTATATTT
TCTTTTAAAGCTAAACATTGTTTGTTTACAATAACATTGTTTACAAACAATTGAGTAAAA
GCTTACATTTTGGCTTCTAATGTGGTTGAATAAAGCTCAAGATGCAGAAGTTATATTCTT
CAAAAATCTATGGCTATATTTAATTATTAAAGTCCAAAAATGGATGTACTTAAAAAAAAT
GGATAAGCTTTAAAACATGAACCCCAACCCTTTCTTCAACACAGAGACGGCATCACAGCC
AGTAAACCAGAGGGCACCGGATGGAGCAATATCCCAATGGGCATGCTCATGGGCCACGTG
ACCTACGACCTGGGCCGTCTTTGGGTCGTCTCCAAGTCTGGCGGCACCATGGTGTGCACA
CATTAGCCTCTTCTCTGTAGCTGAAGGCCGTTCGGGATCTGTCTAAAGTTCACTTGCGAA
CTCATTGATCTCTCTTTCTGGAAAGCCTTTAGTTCATTAGTTCATAAAAATCCTTCATT
TTAAAACCTATTGCTCTACCTATTATTTTCAGTTCTTCAATTATCTTATTGCCATTTAAA
AAAATATCAATGAAGATGTTATATTTTCTTGACCACTCCTTGATTAACACTTCAATAGAT
CTTTGCCATGGAGGCTATTTAAGTGTAGTGTAAACTAGGGCACGGTCATGTTGCTCACAA
TCCACATGGGTTTTGCTGTGCTTCAGAGGTCATCAATAGGATTTGACGGAATCCTTGTCA
TTGTTTATTATCTCATTATATAATCATTTCCTGCAAAAATAAA
```

2323 bp

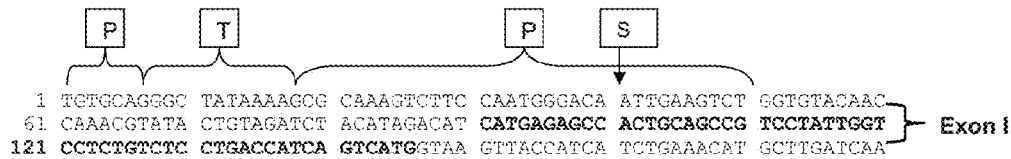

FIG. 9B-2

```
 181 CTTGGAGTTG AAGTTTTTCT TGGTATACTC TACTCATATG TCTTTGTCTC CATAGCATGG ⎤
 241 GACTGTCAGG AGGTAGTAAA CATCAAGAAT CTGATGCAGA TCGATGCAGG ACTGGGGCAA │
 301 GTGGTTGCTA CGGACACAAG TCAAATCCCC TACTACCTGG TAGGTGATAA ATGGATCCGT ├ Exon II
 361 CTGCCTGGTT CCCTGAAGCA TATCACTGTA GGACCAGCAG GGATCTGGGG TGTCAACAAG ⎦
 421 GACTATGCAA TCTACAAGTA TGTGGCCGGT AACTGGGTTC AAGCTGCAGC TAACTGCACA
 481 GCATTACTCA ATATTTATCC ACAGGACACC TGCTTATTAG CTTTCCTCAT ACCATCAGCC
 541 TGTTGAAAAA AACGATTGAT GTTTTAAATT GTAACTTGTA GGTAATTTGG CAGTACTCCT
 601 TGTTTGCTTG TCTGTCTGTC TTTGTGGTCT TGGCCTTCTG AAACAGTTGG ATGCTGGAGG ⎤
 661 TGAACAGTTT ATTGTGGGGG CTAACATGAA CGATACTCCA TACTGTCTGA CAAGTAGTGC │
 721 CACAGTTGGC TACAAGGGTC CAGGCTCACC CCTTCCATGG ACAGGATTGC CAGGAGCTGT ├ Exon III
 781 GAAGTACTAC AGCTGCGGAC CCTTTGGGTG CTGGGCAGTC AACAAGAATG ATGATATCTA │
 841 CTTAATGAGT GTAAGATCTG GGAAGAGTG GGAGAGCTGG AGTAGAGTAG TAGAGGATGG ⎦

901 AGAGTGTCAG TTATTTTAAA ACTGTTTCAT ATTATAACTG TTGAAATTGT CCTAAACCC ⎤
 961 TGATTGTATC ATTTTGTTTC CAGCTGAATC AAGACTGCCA AAACAAGGGG TGGAGTCACA ├ Exon IV
1021 TTGAAGGCAA GCTTTCCATG ATTGAGGTGG CAACTGATGG TAGTGTCTTT GGGGTCAACT ⎦
1081 CTGCGGGTAG TGTTTATACC CAGGTAAGGT TGCTACTGAA CTATGTGTAT GGTCCACCAC
1141 CCCCCCCCCC CCAACAGTAT TAACTTGAAA ATGACTTGTA ATAATAACTT AGAATAATAA
1201 TTTAATTATA ACTCTGATCC TTACGTACA ATGCTCCTTAC
1261 ACAAAAACTA AATATTGTAG GTACATAAAT AAAATCAGTT AAATATAATC AGATCTAAAC
1321 TTATAGGACT TATTAAGAAA TGTGTAGACA GTGTATGATA AAATATGTAA AAGTTGGATG
1381 TCCTGTAAAG CTACAGTTTG GGATAAAAAA CAACAACTTC CCAGACACCC CACCCACTTGT
1441 TCTGGTAAAC AGCTGAGGAA TGTAGTTAGA GAAATGTAAC CACTCTCACA TTCATACATG
1501 GAGCTACGGA TGCAAAGACA CAACAATTTT TTTATTAAAA AAAAAAAAAT GTTTATATTT
1561 TCTTTTAAAG CTAAACATTG TTTGTTTACA ATAACATTGT TTACAAACAA TTGAGTAAAA
1621 GCTTACATTT TGGCTTCTAA TGTGTTGAA TAAAGCTCAA GATGCAGAAG TTATATTCTT
1681 CAAAATCTA TGGCTATATT TAATTATTAA AGTCCAAAAA TGGATGTACT TAAAAAAAAT
1741 GGATAAGCTT TAAAACATGA ACCCCAACCC TTTCTTCAAC ACAGAGACGG CATCACAGCC ⎤
1801 AGTAAACCAG AGGGCACCGG ATGGAGCAAT ATCCCAATGG GCATGCTCAT GGGCCACGTG │
1861 ACCTACGACC TGGGCCGTCT TTGGGTCGTC TCCAAGTCTG GCGGCACCAT GGTGTGCACA ├ Exon V
1921 CATTAGCCTC TTCTCTGTAG CTGAAGGCCG TTCGGGATCT GTCTAAAGTT CACTTGCGAA ⎦
1981 CTCATTGATC TCTCTTTCTG GAAAAGCCTT TAGTTCATTA GTTCATAAAA ATCCTTCATT
2041 TTAAAACCTA TTGCTCTACC TATTATTTTC AGTTCTTCAA TTATCTTATT GCCATTTAAA
2101 AAAATATCAA TGAAGATGTT ATATTTTCTT GACCACTCCT TGATTAACAC TTCAATAGAT
2161 CTTTGCCATG GAGGCTATTT AAGTGTAGTG TAAACTAGGG CACGGTCATG TTGCTCACAA
2221 TCCACATGGG TTTTGCTGTG CTTCAGAGGT CATCAATAGG ATTTGACGGA ATCCTTGTCA
2281 TTGTTTATTA TCTCATTATA TAATCATTTC CTGCAAAAAT AAA ⎤
//                                                          └─┬─┘
                                                             PA
```

FIG. 10C-1
Ensembl Human Blast

| Query Start | Subject End | Chromosome Ori | Chromosome Name | Stats (Start) | (End) | Ori | (Name) | Start | End | Ori | Score | E-val | (%ID) | Length |
|---|---|---|---|---|---|---|---|---|---|---|---|---|---|---|
| 133 | 245 | + | ENSP00000369121 | 976 | 1094 | + | Chr7 | 97685045 | 97690243 | - | 162 | 3.1e-14 | 27.94 | 136 |
| 70 | 225 | + | ENSP00000369121 | 206 | 375 | + | Chr7 | 97704080 | 97710756 | - | 161 | 3.4e-07 | 28.65 | 185 |
| 128 | 242 | + | ENSP00000369121 | 226 | 347 | + | Chr7 | 97704164 | 97708474 | - | 146 | 6.2e-06 | 29.77 | 131 |
| 67 | 229 | + | ENSP00000352510 | 1174 | 1312 | + | Chr14 | 101988597 | 102033664 | + | 146 | 8.8e-06 | 29.75 | 158 |
| 24 | 247 | + | ENSP00000343459 | 722 | 953 | + | Chr2 | 87058229 | 87066443 | + | 140 | 6.9e-05 | 26.32 | 266 |
| 24 | 247 | + | ENSP00000332727 | 722 | 953 | + | Chr2 | 87064748 | 87072960 | + | 140 | 6.9e-05 | 26.32 | 266 |
| 28 | 247 | + | ENSP00000381253 | 2 | 227 | + | Chr2 | 87058247 | 87056443 | - | 139 | 4.9e-05 | 26.15 | 260 |
| 28 | 247 | + | ENSP00000381214 | 2 | 227 | + | Chr2 | 87064748 | 87072942 | + | 139 | 4.9e-05 | 26.15 | 260 |
| 99 | 255 | + | ENSP00000370907 | 21 | 165 | + | Chr10 | 420559 | 435060 | + | 138 | 2.1e-05 | 30.11 | 175 |
| 99 | 255 | + | ENSP00000280886 | 417 | 561 | + | Chr10 | 420559 | 435060 | + | 138 | 9.8e-05 | 30.11 | 175 |
| 16 | 155 | + | ENSP00000367888 | 797 | 950 | + | Chr11 | 46857407 | 46864487 | + | 136 | 0.00019 | 28.89 | 160 |
| 16 | 155 | + | ENSP00000256991 | 842 | 995 | + | Chr11 | 46857407 | 46864487 | + | 136 | 0.00019 | 28.89 | 160 |
| 23 | 155 | + | ENSP00000351261 | 217 | 351 | + | Chr1 | 158329597 | 158330379 | + | 135 | 6.2e-05 | 31.25 | 160 |
| 23 | 155 | + | ENSP00000357065 | 217 | 351 | + | Chr1 | 158329597 | 158330379 | + | 135 | 7.3e-05 | 31.25 | 160 |
| 23 | 155 | + | ENSP00000316664 | 217 | 351 | + | Chr1 | 158329597 | 158330379 | + | 135 | 7.3e-05 | 31.25 | 160 |
| 50 | 249 | + | ENSP00000381646 | 22 | 221 | + | Chr21 | 41610590 | 41642416 | + | 133 | 4.9e-05 | 27.66 | 235 |
| 44 | 237 | + | ENSP00000325146 | 736 | 944 | + | Chr6 | 75932094 | 75944330 | - | 133 | 0.00061 | 26.25 | 240 |
| 44 | 237 | + | ENSP00000359153 | 736 | 944 | + | Chr6 | 75932094 | 75944330 | - | 133 | 0.00061 | 26.25 | 240 |
| 102 | 196 | + | ENSP00000358286 | 668 | 778 | + | Chr10 | 115963265 | 115968173 | + | 131 | 0.00034 | 33.33 | 117 |
| 102 | 196 | + | ENSP00000358288 | 668 | 778 | + | Chr10 | 115963265 | 115968173 | + | 131 | 0.00034 | 33.33 | 117 |
| 102 | 196 | + | ENSP00000251864 | 668 | 778 | + | Chr10 | 115963265 | 115968173 | + | 131 | 0.00037 | 33.33 | 117 |
| 19 | 117 | + | ENSP00000369121 | 235 | 344 | + | Chr7 | 97705760 | 97708447 | - | 130 | 3.1e-14 | 30.51 | 118 |
| 63 | 241 | + | ENSP00000348169 | 43 | 206 | + | ChrY | 15243520 | 15344542 | + | 130 | 0.00031 | 30.00 | 190 |
| 63 | 241 | + | ENSP00000345535 | 43 | 206 | + | ChrY | 15243520 | 15344542 | + | 130 | 0.00031 | 30.00 | 190 |
| 102 | 177 | + | ENSP00000358287 | 611 | 699 | + | Chr10 | 115963265 | 115967349 | + | 129 | 0.00053 | 34.04 | 94 |
| 129 | 247 | + | ENSP00000347081 | 855 | 973 | + | Chr2 | 107849171 | 107853826 | - | 129 | 0.00088 | 30.77 | 143 |
| 47 | 237 | + | ENSP00000352510 | 835 | 1035 | + | Chr14 | 101974220 | 101985740 | + | 128 | 0.00088 | 22.42 | 223 |
| 157 | 242 | + | ENSP00000369121 | 175 | 257 | + | Chr7 | 97708379 | 97711827 | - | 127 | 0.00067 | 30.93 | 97 |
| 83 | 219 | + | ENSP00000362743 | 42 | 165 | + | Chr2 | 231611029 | 231619968 | + | 127 | 0.00010 | 26.49 | 151 |
| 153 | 246 | + | ENSP00000369121 | 205 | 308 | + | Chr7 | 97708108 | 97710759 | - | 126 | 0.00084 | 25.89 | 112 |
| 129 | 247 | + | ENSP00000016946 | 854 | 977 | + | Chr2 | 109946276 | 109950918 | + | 126 | 0.0018 | 31.25 | 144 |

FIG. 10C-2

Ensembl Human Blast

| | | | | | | | | | | | |
|---|---|---|---|---|---|---|---|---|---|---|---|
| 129 | 247 | + | ENSP00000330842 | 654 | 977 | + | Chr.2 | 110727569 | 110732211 | + | 126 | 0.0016 | 31.25 | 144 |
| 53 | 160 | + | ENSP00000329051 | 148 | 254 | + | Chr.9 | 138968231 | 138968740 | + | 125 | 0.00040 | 30.65 | 124 |
| 54 | 238 | + | ENSP00000342194 | 68 | 260 | + | Chr.19 | 3332881 | 3385345 | + | 125 | 0.00049 | 28.57 | 210 |
| 54 | 238 | + | ENSP00000378543 | 59 | 251 | + | Chr.19 | 3332881 | 3385345 | + | 125 | 0.00050 | 28.57 | 210 |
| 61 | 235 | + | ENSP00000288167 | 41 | 215 | + | Chr.3 | 53858757 | 53866026 | + | 125 | 0.00059 | 27.27 | 198 |
| 54 | 238 | + | ENSP00000342859 | 68 | 260 | + | Chr.19 | 3332881 | 3385345 | + | 125 | 0.00060 | 28.57 | 210 |
| 54 | 238 | + | ENSP00000269778 | 68 | 260 | + | Chr.19 | 3332881 | 3385345 | + | 125 | 0.00060 | 28.57 | 210 |
| 109 | 228 | + | ENSP00000257359 | 396 | 533 | + | Chr.11 | 129786673 | 129791346 | + | 125 | 0.0011 | 28.66 | 157 |
| 129 | 221 | + | ENSP00000303659 | 855 | 946 | + | Chr.2 | 106408017 | 106412576 | - | 125 | 0.0022 | 34.26 | 108 |
| 26 | 255 | + | ENSP00000229195 | 134 | 375 | + | Chr.12 | 69010347 | 69018816 | + | 124 | 0.00060 | 25.00 | 276 |
| 27 | 218 | + | ENSP00000381054 | 616 | 808 | + | Chr.11 | 112631859 | 112651199 | + | 124 | 0.0013 | 28.63 | 227 |
| 27 | 218 | + | ENSP00000318472 | 626 | 818 | + | Chr.11 | 112631859 | 112651199 | + | 124 | 0.0013 | 28.63 | 227 |
| 64 | 242 | + | ENSP00000264350 | 125 | 305 | + | Chr.4 | 89599628 | 89607236 | + | 123 | 0.0016 | 29.27 | 205 |
| 55 | 222 | + | ENSP00000369121 | 963 | 1124 | + | Chr.7 | 97684955 | 97690282 | - | 123 | 0.0023 | 25.79 | 190 |
| 45 | 192 | + | ENSP00000355720 | 195 | 355 | + | Chr.1 | 225987247 | 225988340 | + | 123 | 0.00086 | 26.70 | 176 |
| 124 | 231 | + | ENSP00000376771 | 46 | 163 | + | Chr.11 | 111401542 | 111404556 | + | 123 | 0.0010 | 30.08 | 133 |
| 124 | 231 | + | ENSP00000280246 | 46 | 163 | + | Chr.11 | 111401542 | 111404556 | + | 123 | 0.0012 | 30.08 | 133 |
| 73 | 234 | + | ENSP00000384533 | 467 | 639 | + | Chr.2 | 29233714 | 29256008 | - | 123 | 0.0014 | 23.74 | 198 |
| 69 | 253 | + | ENSP00000000412 | 63 | 244 | + | Chr.12 | 8985783 | 8989437 | + | 122 | 0.00060 | 26.76 | 213 |
| 129 | 221 | + | ENSP00000306637 | 654 | 945 | + | Chr.12 | 11286458 | 112868708 | + | 122 | 0.0044 | 34.86 | 109 |
| 72 | 185 | + | ENSP00000377534 | 213 | 324 | + | Chr.2 | 8342029 | 8344635 | + | 121 | 0.0010 | 28.03 | 132 |
| 72 | 185 | + | ENSP00000301455 | 251 | 362 | + | Chr.2 | 8342029 | 8344635 | + | 121 | 0.0012 | 28.03 | 132 |
| 118 | 227 | + | ENSP00000380066 | 655 | 749 | + | Chr.19 | 43778142 | 43778945 | + | 121 | 0.0025 | 30.33 | 122 |
| 88 | 241 | + | ENSP00000354541 | 55 | 215 | + | Chr.3 | 174805245 | 175008315 | - | 121 | 0.0025 | 26.63 | 184 |
| 44 | 210 | + | ENSP00000376938 | 67 | 250 | + | Chr.19 | 43778142 | 43778945 | + | 121 | 0.0025 | 29.84 | 191 |
| 118 | 227 | + | ENSP00000221409 | 655 | 749 | + | Chr.12 | 75310500 | 75317822 | + | 121 | 0.0025 | 30.33 | 122 |
| 44 | 210 | + | ENSP00000376939 | 102 | 265 | + | Chr.12 | 75310500 | 75317822 | + | 121 | 0.0026 | 29.84 | 191 |
| 44 | 210 | + | ENSP00000378940 | 129 | 292 | + | Chr.12 | 75310500 | 75317822 | + | 121 | 0.0027 | 29.84 | 191 |
| 44 | 210 | + | ENSP00000261183 | 144 | 307 | + | Chr.12 | 75310500 | 75317822 | + | 121 | 0.0027 | 29.84 | 191 |
| 124 | 239 | + | ENSP00000366272 | 324 | 441 | + | Chr.10 | 21999558 | 22002556 | + | 121 | 0.0032 | 29.41 | 136 |
| 124 | 239 | + | ENSP00000366258 | 324 | 441 | + | Chr.10 | 21999558 | 22002556 | + | 120 | 0.0033 | 29.41 | 136 |
| 133 | 249 | + | ENSP00000322242 | 223 | 340 | + | Chr.12 | 119479489 | 119482964 | + | 120 | 0.0031 | 28.37 | 141 |
| 26 | 156 | + | ENSP00000358106 | 426 | 573 | + | Chr.6 | 105836433 | 105878277 | - | 119 | 0.0034 | 27.27 | 165 |
| 60 | 158 | + | ENSP00000355637 | 35 | 128 | + | Chr.1 | 227760639 | 227760920 | - | 119 | 0.0036 | 28.45 | 116 |

FIG. 10C-3

Ensembl Human Blast

| | | | | | | | | | | | | | | |
|---|---|---|---|---|---|---|---|---|---|---|---|---|---|---|
| 83 | 241 | + | ENSP00000275857 | 43 | 208 | + | ChrX | 5957322 | 6079381 | , | 119 | 0.0040 | 29.47 | 190 |
| 83 | 241 | + | ENSP00000370485 | 43 | 208 | + | ChrX | 5957322 | 6079381 | , | 119 | 0.0040 | 29.47 | 190 |
| 83 | 241 | + | ENSP00000370482 | 43 | 208 | + | ChrX | 5957322 | 6079381 | , | 119 | 0.0040 | 29.47 | 190 |
| 58 | 147 | + | ENSP00000251375 | 32 | 124 | + | Chr19 | 59797965 | 59798390 | + | 118 | 0.0016 | 30.69 | 101 |
| 108 | 234 | + | ENSP00000293805 | 264 | 403 | + | Chr17 | 6869144 | 6871016 | + | 118 | 0.0028 | 30.52 | 154 |
| 58 | 147 | + | ENSP00000251372 | 32 | 124 | + | Chr19 | 59797965 | 59798390 | + | 118 | 0.0029 | 30.69 | 101 |
| 106 | 234 | + | ENSP00000368859 | 488 | 623 | + | Chr2 | 29236765 | 29258008 | + | 118 | 0.0043 | 26.11 | 157 |
| 50 | 155 | + | ENSP00000379819 | 116 | 213 | + | Chr2 | 227818935 | 227824325 | + | 118 | 0.0069 | 31.93 | 119 |
| 50 | 155 | + | ENSP00000335120 | 116 | 213 | + | Chr2 | 227818935 | 227824325 | + | 118 | 0.0093 | 31.93 | 119 |
| 50 | 155 | + | ENSP00000323334 | 116 | 213 | + | Chr2 | 227818935 | 227824325 | + | 118 | 0.0093 | 31.93 | 119 |
| 50 | 155 | + | ENSP00000302781 | 116 | 213 | + | Chr2 | 227818935 | 227824325 | , | 117 | 0.010 | 31.93 | 119 |
| 50 | 155 | + | ENSP00000379833 | 116 | 213 | + | Chr2 | 227818935 | 227824325 | , | 117 | 0.010 | 31.93 | 119 |
| 47 | 155 | + | ENSP00000301921 | 89 | 184 | + | Chr8 | 10621273 | 10621560 | + | 117 | 0.0028 | 31.67 | 120 |
| 101 | 242 | + | ENSP00000313437 | 292 | 449 | + | Chr12 | 54517267 | 54518678 | + | 117 | 0.0038 | 29.51 | 183 |
| 106 | 234 | + | ENSP00000385148 | 381 | 514 | + | Chr2 | 29236765 | 29258008 | , | 117 | 0.0043 | 25.16 | 155 |
| 106 | 234 | + | ENSP00000385594 | 488 | 621 | + | Chr2 | 29236765 | 29258008 | + | 117 | 0.0054 | 25.16 | 155 |
| 106 | 234 | + | ENSP00000327009 | 488 | 621 | + | Chr2 | 29236765 | 29258008 | , | 117 | 0.0054 | 25.16 | 155 |
| 127 | 242 | + | ENSP00000377736 | 28 | 163 | + | Chr12 | 54517267 | 54518014 | + | 116 | 0.0019 | 30.25 | 152 |
| 18 | 255 | + | ENSP00000384533 | 193 | 437 | + | Chr2 | 29211962 | 29233626 | , | 115 | 0.0087 | 24.36 | 275 |
| 55 | 159 | + | ENSP00000259870 | 224 | 310 | + | Chr6_COX | 31187185 | 31187445 | + | 115 | 0.0036 | 27.35 | 117 |
| 55 | 159 | + | ENSP00000372839 | 224 | 310 | + | Chr6_COX | 31218960 | 31219220 | , | 115 | 0.0036 | 27.35 | 117 |
| 55 | 159 | + | ENSP00000373024 | 224 | 310 | + | Chr6_QBL | 31214480 | 31214740 | , | 115 | 0.0036 | 27.35 | 117 |
| 18 | 255 | + | ENSP00000368859 | 192 | 436 | + | Chr2 | 29211962 | 29233626 | + | 115 | 0.0085 | 24.36 | 275 |
| 18 | 255 | + | ENSP00000385148 | 85 | 329 | + | Chr2 | 29211962 | 29233626 | , | 115 | 0.0068 | 24.36 | 275 |
| 18 | 255 | + | ENSP00000385594 | 192 | 436 | + | Chr2 | 29211962 | 29233626 | + | 115 | 0.0085 | 24.36 | 275 |
| 18 | 255 | + | ENSP00000327009 | 192 | 436 | + | Chr2 | 29211962 | 29233626 | , | 115 | 0.0085 | 24.36 | 275 |
| 58 | 200 | + | ENSP00000084242 | 192 | 436 | + | Chr4 | 81195562 | 81212699 | + | 115 | 0.0071 | 24.36 | 275 |
| 58 | 200 | + | ENSP00000295465 | 14 | 154 | + | Chr4 | 81195562 | 81212699 | + | 114 | 0.0046 | 26.79 | 168 |
| 58 | 200 | + | ENSP00000314883 | 14 | 154 | + | Chr4 | 81195562 | 81212699 | + | 114 | 0.0056 | 26.79 | 168 |
| 58 | 200 | + | ENSP00000382324 | 14 | 154 | + | Chr4 | 81195562 | 81212699 | + | 114 | 0.0071 | 26.79 | 168 |
| 58 | 200 | + | ENSP00000385575 | 14 | 154 | + | Chr4 | 81195562 | 81212699 | , | 114 | 0.0072 | 26.79 | 168 |
| 58 | 200 | + | ENSP00000306185 | 14 | 154 | + | Chr4 | 81195562 | 81212699 | , | 114 | 0.0073 | 26.79 | 168 |
| 104 | 232 | + | ENSP00000225655 | 2 | 115 | + | Chr17 | 4790018 | 4792431 | , | 113 | 0.0021 | 29.08 | 141 |
| 22 | 127 | + | ENSP00000274327 | 34 | 144 | + | Chr5 | 64943399 | 64949820 | - | 113 | 0.010 | 26.83 | 123 |

FIG. 10C-4
Ensembl Human Blast

| | | | | | | | | | | | | |
|---|---|---|---|---|---|---|---|---|---|---|---|---|
| 22 | 127 | + | ENSP00000370406 | 34 | 144 | + | Chr5 | 64343339 | 64949820 | - | 113 | 0.011 | 26.83 | 123 |
| 34 | 187 | + | ENSP00000355262 | 191 | 345 | + | Chr1 | 201453611 | 201458920 | . | 112 | 0.0089 | 26.67 | 180 |
| 33 | 155 | + | ENSP00000368364 | 66 | 185 | + | Chr19 | 40695404 | 40696022 | . | 112 | 0.0099 | 28.47 | 144 |
| 30 | 215 | + | ENSP00000352510 | 174 | 369 | + | Chr14 | 101950765 | 101967908 | + | 111 | 0.044 | 27.43 | 226 |
| 48 | 155 | + | ENSP00000373691 | 1242 | 1368 | + | Chr15 | 43175062 | 43176851 | . | 111 | 0.0070 | 26.21 | 145 |
| 48 | 155 | + | ENSP00000267837 | 1242 | 1368 | + | Chr15 | 43175062 | 43176851 | . | 111 | 0.0070 | 26.21 | 145 |
| 48 | 155 | + | ENSP00000379945 | 1242 | 1368 | + | Chr15 | 43175062 | 43176851 | . | 111 | 0.0070 | 26.21 | 145 |
| 85 | 138 | + | ENSP00000341261 | 109 | 161 | + | Chr21 | 43694742 | 43694900 | . | 110 | 0.0050 | 36.07 | 61 |
| 54 | 145 | + | ENSP00000360693 | 80 | 161 | + | Chr9 | 138968049 | 138968668 | + | 108 | 0.0084 | 32.65 | 98 |
| 133 | 181 | + | ENSP00000301698 | 361 | 399 | + | Chr16 | 803734 | 803850 | + | 104 | 1.8e-05 | 35.85 | 53 |
| 68 | 184 | + | ENSP00000325146 | 1769 | 1869 | + | Chr6 | 75900351 | 75903962 | . | 102 | 0.77 | 31.75 | 126 |
| 68 | 184 | + | ENSP00000359153 | 1769 | 1869 | + | Chr6 | 75900351 | 75903962 | . | 102 | 0.77 | 31.75 | 126 |
| 33 | 135 | + | ENSP00000349790 | 64 | 163 | + | Chr6 | 71060798 | 71066576 | + | 101 | 0.0041 | 27.50 | 120 |
| 101 | 208 | + | ENSP00000369121 | 696 | 794 | + | Chr7 | 97696315 | 97698510 | . | 97 | 6.5e-08 | 25.21 | 119 |
| 29 | 138 | + | ENSP00000369121 | 1035 | 1158 | + | Chr7 | 97644665 | 97688966 | + | 93 | 2.3 | 26.87 | 134 |
| 120 | 242 | + | ENSP00000259870 | 137 | 272 | + | Chr6_COX | 31187299 | 31187706 | + | 93 | 0.59 | 30.52 | 154 |
| 120 | 242 | + | ENSP00000372839 | 137 | 272 | + | c6_COX | 31219074 | 31219481 | + | 92 | 0.74 | 30.52 | 154 |
| 120 | 242 | + | ENSP00000373024 | 137 | 272 | + | c6_QBL | 31214594 | 31215001 | + | 92 | 0.74 | 30.52 | 154 |
| 106 | 179 | + | ENSP00000384242 | 488 | 573 | + | Chr2 | 29236765 | 29243906 | . | 91 | 1.8 | 24.47 | 94 |
| 37 | 248 | + | ENSP00000369121 | 796 | 1010 | + | Chr7 | 97689671 | 97696311 | + | 90 | 4.5 | 22.92 | 253 |
| 27 | 76 | + | ENSP00000301698 | 280 | 331 | + | Chr16 | 803491 | 803646 | + | 88 | 1.8e-05 | 35.59 | 59 |
| 190 | 251 | + | ENSP00000376924 | 434 | 491 | + | Chr7 | 129154393 | 129182218 | + | 85 | 0.0091 | 32.86 | 70 |
| 190 | 251 | + | ENSP00000223190 | 434 | 491 | + | Chr7 | 129154393 | 129182218 | + | 85 | 0.0091 | 32.86 | 70 |
| 190 | 251 | + | ENSP00000376922 | 434 | 491 | + | Chr7 | 129154393 | 129182218 | + | 85 | 0.0091 | 32.86 | 70 |
| 16 | 70 | + | ENSP00000376922 | 297 | 370 | + | Chr7 | 129137573 | 129144339 | + | 81 | 0.0091 | 29.49 | 78 |
| 16 | 70 | + | ENSP00000223190 | 297 | 370 | + | Chr7 | 129137573 | 129144339 | + | 81 | 0.0091 | 29.49 | 78 |
| 16 | 70 | + | ENSP00000376922 | 297 | 370 | + | Chr7 | 129137573 | 129144339 | + | 81 | 0.0091 | 29.49 | 78 |
| 129 | 155 | + | ENSP00000349790 | 353 | 382 | + | Chr6 | 71036789 | 71040479 | + | 74 | 0.0041 | 43.75 | 32 |
| 149 | 168 | + | ENSP00000373691 | 1515 | 1542 | + | Chr15 | 43173661 | 43173744 | . | 66 | 0.0070 | 35.71 | 28 |
| 149 | 168 | + | ENSP00000267837 | 1515 | 1542 | + | Chr15 | 43173661 | 43173744 | . | 66 | 0.0070 | 35.71 | 28 |
| 149 | 168 | + | ENSP00000379945 | 1515 | 1542 | + | Chr15 | 43173661 | 43173744 | . | 66 | 0.0070 | 35.71 | 28 |
| 129 | 146 | + | ENSP00000349790 | 841 | 857 | + | Chr6 | 70992366 | 70992416 | . | 64 | 0.035 | 50.00 | 20 |
| 31 | 88 | + | ENSP00000369121 | 6 | 58 | + | Chr7 | 97713221 | 97713379 | - | 58 | 2.7e-07 | 26.67 | 60 |

FIG. 14B

```
                      TECPR 4                                                         TECPR 5
                170       180       190       200       210       220       230       240
Lect_EPFL    KLKQIDGGYNH--VYGVNSNNDIF-------TLPVDGSGSWRH-IPGKLKHVSASGTHSVFGTGPDDTIWR-----CRKPCV
GBP_SUDO     KLKQIDGGHKY--VYGVNSANQIF-------SRAVDGSGNWRH-IPGSLAHVTASGDDIFGVNKAQNIFR-----CKKPCI
L6_TATR      RLKQIDGGGQSM--VYGVNSANAIY------RRPVDGSGSWQQ-ISGSLKHITGSSGLSEVFGVNSNDQIYR-----CTKPCS
GBP_TATR     SLKQVDGGRDL--VYGVTQNDEIF-------RRPVDGSGGWVN-IPGRLKHISGGSGSWEVFGVNCNDQIFR-----CKKPCS
TLP_TATR     RLKQIDGGGQSM--VYGVNSANAIY------RRPVDGSGSWQQ-ISGSLKHITGSSGISEVFGVNSNDQIYR-----CTKPCS
Tect1_PHPO   ALTNVSVGKDGTVYGVNRGHQIY--------RWDGSKVDLVLGEIVQIHVSDAEKIVGVNHLDRIYR-----------LKHG
GlP_DARE     KLKYYSCGPYS--CCGVNSADRIFIMKGVSSNACSGDGTFVN-IPGLLSMIEVGTDGSVFGVNYEAKLFQRVGVSRSNPAG
PMP_CAAU     KLKYYSCGPYS--CWGVNHNDQIFIMKDVSSSVCSGSGSFVN-IPGLLSMIEVATDGSVYGVNSQGSLFKRTGVTRCTPDG
FEL_CYCA     KLKYYSCGPYS--CWGVNSNDQIFIMKDVSSNVCSGSGSFIN-IPGLLSMIEVATDGSVFGVNSQGNLYQRTGVTRSKPDG
LL_SASA      AVKYYSCGPFG--CWAVNKNDDIYLMSL----NQDCQNKG-WSH-IEGKLSMIEVATDGSVFGVNSAGSVYTRDGITASKPEG Consensus    RLKQ++GGPYS--VYGVNSNDQIFIMKDVSSRPVDGSGSWVN--IPG+L+HIEVSGDGSVFGVNSNDQIYRRTGVTCSKPCG
```

```
                250       260       270       280
Lect_EPFL    GEWERI-----DGGLKQCDATING-LYGVNSGDSIFRSALGL-------
GBP_SUDO     GEWEQM-----EGKLNQCDATING-VFGVKS--GTFRHVIGA-------
L6_TATR      GQWSLI-----DGRLKQCDATGNT-IVGVNSVDNIYRSG----------
GBP_TATR     GQWVRL-----SGYLKQCDASGDS-LLGVNSNDDIFESVPASKSCWMNPFL
TLP_TATR     GQWSLI-----DGKLKQCDAT----------------------------
Tect1_PHPO   KDWEKL-----DGELTWVSVGHHGEVWGVNKLHHIYKATL---------
GlP_DARE     TDWISMIACPIG--HKHVSLDLGVLMVCVDGSIRKCTL-----------
PMP_CAAU     TDWIPVVACPNG--HQHVSFDLGVLMVCVDGSIRKCS------------
FEL_CYCA     TDWISMVACPNG--BKHVSFDLGVLMLVCVDGSIRKCILTD--------
LL_SASA      TGWSNI-----PMGMLMGHVTYDLGRLMVSKSGGTMVCTH---------

Consensus    GDW++IVACPDGKLKQCDATDLGVLWGVNSDGSI+KCTLG---------
```

FIG. 15

```
Leukolectin
           1           10          20          30    36
Consensus  XXWXXLPGXLKXXXVGPX-XGVWGVNKNDXXXLVG
Identity
R1         WDCQEVNIKNLMQIDAGLGQVVATDTGRIPYYLVG
R2         DKWIRLPGSLKHVTVGPA--GIWGVNKDYAIYKYVA
R3         GNWVQAAGLLKQLDAGGEQFIV-GANMNDTPYRLTS
R4         LPWTGLPGAVKYYSCGP---FGCWAVNKNDDIYLMSL
R5         KGWSHIEGKLSMIEVATD-GSVFGVNSAGSVYTRDG Fish egg Lectin FEL
           1           10          20          30    35
Consensus  GXFXQIXGLLKQIXXGPDXXV-GVNSXENIFXLXD
Identity
R1         LDCTVIDGNLKQIDAGSGSVV-GVNNLNETFVLID
R2         NVFTKISGSLKHFSVGPAGQL-GVNTANNIFKYQS
R3         GGFVQLAGLLKQVDAGGDQIIAGVNMYDDIYCLNM
R4         TPWVQINGKLKYYSCGPYSC-WGVNSNDQIFIMKD
R5         GSFINIPGLLSMIEVATDGSSVFGVNSQGNLYQRTG
```

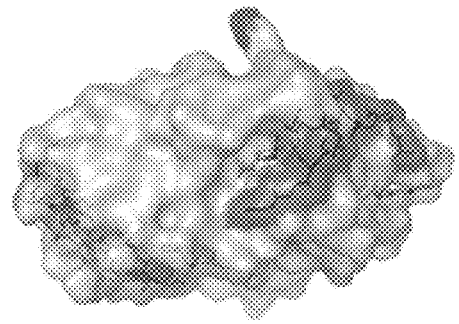
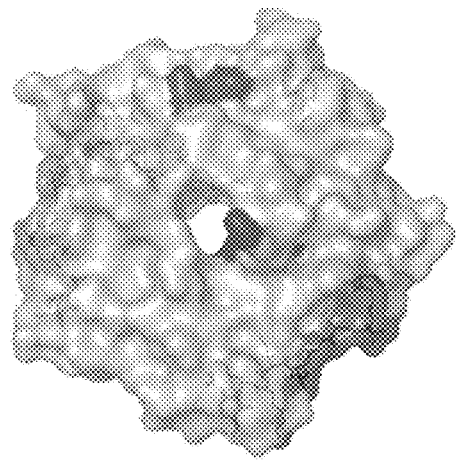

SEQUENCE LISTING

```
<160> NUMBER OF SEQ ID NOS: 67

<210> SEQ ID NO 1
<211> LENGTH: 255
<212> TYPE: PRT
<213> ORGANISM: Salmo salar

<400> SEQUENCE: 1

Met Arg Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
            20                  25                  30

Gln Ile Asp Ala Gly Leu Gly Gln Val Val Ala Thr Asp Thr Ser Gln
        35                  40                  45

Ile Pro Tyr Tyr Leu Val Gly Asp Lys Trp Ile Arg Leu Pro Gly Ser
    50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95
```

```
Gly Leu Leu Lys Gln Leu Asp Ala Gly Gly Glu Gln Phe Ile Val Gly
                100                 105                 110

Ala Asn Met Asn Asp Thr Pro Tyr Cys Leu Thr Ser Ser Ala Thr Val
            115                 120                 125

Gly Tyr Lys Gly Pro Gly Ser Pro Leu Pro Trp Thr Gly Leu Pro Gly
        130                 135                 140

Ala Val Lys Tyr Tyr Ser Cys Gly Pro Phe Gly Cys Trp Ala Val Asn
145                 150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
210                 215                 220

Ile Pro Met Gly Met Leu Met Gly His Val Thr Tyr Asp Leu Gly Arg
225                 230                 235                 240

Leu Trp Val Val Ser Lys Ser Ala Val Thr Met Val Cys Thr His
                245                 250                 255

<210> SEQ ID NO 2
<211> LENGTH: 208
<212> TYPE: PRT
<213> ORGANISM: Salmo salar

<400> SEQUENCE: 2

Ser Ile Pro Tyr Tyr Leu Val Gly Asp Lys Trp Ile Arg Leu Pro Gly
1               5                   10                  15

Ser Leu Lys His Ile Thr Val Gly Pro Ala Gly Ile Trp Gly Val Asn
            20                  25                  30

Lys Asp Tyr Ala Ile Tyr Lys Tyr Val Ala Gly Asn Trp Val Gln Ala
        35                  40                  45

Ala Gly Leu Pro Lys Gln Leu Asp Ala Gly Gly Glu Gln Phe Ile Val
50                  55                  60

Gly Ala Asn Met Asp Asp Thr Pro Tyr Cys Leu Thr Ser Ser Ala Thr
65                  70                  75                  80

Val Gly Tyr Lys Gly Pro Gly Ser Pro Leu Pro Trp Thr Gly Leu Pro
                85                  90                  95

Gly Ala Val Lys Tyr Tyr Ser Cys Gly Pro Phe Gly Cys Trp Ala Val
            100                 105                 110

Asn Lys Asn Asp Asp Ile Tyr Leu Met Ser Leu Asn Gln Asp Cys Gln
        115                 120                 125

Asn Asn Gly Trp Ser His Ile Glu Gly Lys Leu Ser Met Ile Glu Val
130                 135                 140

Ala Thr Asp Gly Ser Val Phe Gly Val Asn Ser Ala Gly Ser Val Tyr
145                 150                 155                 160

Thr Arg Asp Gly Ile Thr Ala Ser Lys Pro Glu Gly Thr Gly Trp Ser
                165                 170                 175

Asn Ile Pro Met Cys Met Leu Met Gly His Val Thr Tyr Asp Leu Gly
            180                 185                 190

Arg Leu Trp Val Val Ser Lys Ser Ala Val Thr Met Val Cys Thr His
        195                 200                 205
```

-continued

```
<210> SEQ ID NO 3
<211> LENGTH: 158
<212> TYPE: PRT
<213> ORGANISM: Gadus morhua

<400> SEQUENCE: 3

Leu Val Gly Asp Lys Trp Ile Arg Leu Pro Gly Ser Leu Lys His Ile
1               5                   10                  15

Thr Val Gly Pro Ala Gly Ile Trp Gly Val Asn Lys Asp Tyr Ala Ile
            20                  25                  30

Tyr Lys Tyr Val Ala Gly Asn Trp Val Gln Ala Ala Gly Leu Leu Lys
        35                  40                  45

Gln Leu Asp Ala Gly Gly Glu Gln Phe Ile Val Gly Ala Asn Met Asn
    50                  55                  60

Asp Thr Pro Tyr Cys Leu Thr Ser Ser Ala Thr Val Gly Tyr Lys Gly
65                  70                  75                  80

Pro Gly Ser Pro Leu Pro Trp Thr Gly Leu Pro Gly Ala Val Lys Tyr
                85                  90                  95

Tyr Ser Cys Gly Pro Phe Gly Cys Trp Ala Val Asn Lys Asn Asp Asp
            100                 105                 110

Ile Tyr Leu Met Ser Leu Asn Gln Asp Cys Gln Asn Lys Gly Trp Ser
        115                 120                 125

His Ile Asp Gly Lys Leu Ser Met Ile Glu Val Ala Thr Asp Gly Ser
    130                 135                 140

Val Phe Gly Val Asn Ser Ala Gly Ser Val Tyr Thr Arg Asp
145                 150                 155

<210> SEQ ID NO 4
<211> LENGTH: 196
<212> TYPE: PRT
<213> ORGANISM: Gallus gallus

<400> SEQUENCE: 4

Ile Pro Tyr Tyr Leu Val Gly Asp Lys Trp Ile Arg Leu Pro Gly Ser
1               5                   10                  15

Leu Lys His Ile Thr Val Gly Pro Ala Gly Ile Trp Gly Val Asn Lys
            20                  25                  30

Asp Tyr Ala Ile Tyr Lys Tyr Val Ala Gly Asn Trp Val Gln Ala Ala
        35                  40                  45

Gly Leu Leu Lys Gln Leu Asp Ala Gly Gly Glu Gln Phe Ile Val Gly
    50                  55                  60

Ala Asn Met Asn Asp Thr Pro Tyr Cys Leu Thr Ser Ser Ala Thr Val
65                  70                  75                  80

Gly Tyr Lys Gly Pro Gly Ser Pro Leu Pro Trp Thr Gly Leu Pro Gly
                85                  90                  95

Ala Val Lys Tyr Tyr Ser Cys Gly Pro Phe Gly Cys Trp Ala Val Asn
            100                 105                 110

Lys Asn Asp Asp Ile Tyr Leu Met Ser Leu Asn Gln Asp Cys Gln Asn
        115                 120                 125

Lys Gly Trp Ser His Ile Asp Gly Lys Leu Ser Met Ile Glu Val Ala
    130                 135                 140

Thr Asp Gly Ser Val Phe Gly Val Asn Ser Ala Gly Ser Val Tyr Thr
145                 150                 155                 160

Arg Asp Gly Ile Thr Ala Ser Lys Pro Glu Gly Thr Gly Trp Ser Asn
                165                 170                 175

Ile Pro Met Gly Met Leu Met Gly His Val Thr Tyr Asp Leu Gly Arg
```

-continued

```
                  180                 185                 190

Leu Trp Val Val
        195

<210> SEQ ID NO 5
<211> LENGTH: 255
<212> TYPE: PRT
<213> ORGANISM: Homo sapiens

<400> SEQUENCE: 5

Met Arg Ala Thr Ala Ala Val Leu Leu Val Leu Cys Leu Leu Thr Ile
1               5                   10                  15

Ser His Ala Trp Asp Cys Gln Glu Val Val Asn Ile Lys Asn Leu Met
            20                  25                  30

Gln Ile Asp Ala Gly Leu Gly Gln Val Val Ala Thr Asp Thr Gly Arg
        35                  40                  45

Ile Pro Tyr Tyr Leu Val Gly Asp Lys Trp Ile Arg Leu Pro Gly Ser
    50                  55                  60

Leu Lys His Val Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95

Gly Leu Leu Lys Gln Leu Asp Ala Gly Gly Glu Gln Phe Ile Val Gly
            100                 105                 110

Ala Asn Met Asn Asp Thr Pro Tyr Arg Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly Pro Phe Gly Cys Trp Ala Val Asn
145                 150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Ser Lys Ser Gly Gly Thr Met Val Cys Thr His
                245                 250                 255

<210> SEQ ID NO 6
<211> LENGTH: 255
<212> TYPE: PRT
<213> ORGANISM: Danio rerio

<400> SEQUENCE: 6

Met Gly Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
            20                  25                  30

Gln Ile Asp Ala Gly Leu Gly Gln Val Val Ala Thr Asp Thr Ser Gln
        35                  40                  45

Ile Pro Tyr Tyr Leu Val Gly Asp Lys Trp Ile Arg Leu Pro Gly Ser
```

```
            50                  55                  60
Leu Lys His Ile Thr Val Gly Pro Ala Gly Ile Trp Gly Val Asn Lys
 65                  70                  75                  80

Asp Tyr Ala Ile Tyr Lys Tyr Val Ala Gly Asn Trp Val Gln Ala Ala
                 85                  90                  95

Gly Leu Leu Lys Gln Leu Asp Ala Gly Gly Asn Gln Phe Ile Val Gly
            100                 105                 110

Ala Asn Met Asn Asp Thr Pro Tyr Arg Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly Pro Phe Gly Cys Trp Ala Val Asn
145                 150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Thr Lys Ser Gly Gly Thr Met Val Cys Thr His
                245                 250                 255

<210> SEQ ID NO 7
<211> LENGTH: 255
<212> TYPE: PRT
<213> ORGANISM: Salmo salar

<400> SEQUENCE: 7

Met Arg Thr Thr Ala Ala Phe Leu Leu Val Leu Cys Leu Leu Ala Ile
  1               5                  10                  15

Ser His Ala Trp Asp Cys Gln Glu Val Val Asn Ile Lys Asn Leu Met
             20                  25                  30

Gln Ile Asp Ala Gly Leu Gly Gln Val Val Ala Thr Asp Thr Ser Gln
         35                  40                  45

Ile Pro Tyr Tyr Leu Val Gly Asp Lys Trp Ile Arg Leu Pro Gly Ser
     50                  55                  60

Leu Lys His Ile Thr Val Gly Pro Ala Gly Ile Trp Gly Val Asn Lys
 65                  70                  75                  80

Asp Tyr Ala Ile Tyr Lys Tyr Val Ala Gly Asn Trp Val Gln Ala Ala
                 85                  90                  95

Gly Leu Leu Lys Gln Leu Asp Ala Gly Gly Asn Gln Phe Val Val Gly
            100                 105                 110

Ala Asn Met Asp Asp Thr Pro Phe Cys Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly His Phe Gly Cys Trp Ala Val Asn
145                 150                 155                 160

Lys Asn Asp Asp Ile Phe Leu Met Ser Leu Asn Gln Asp Cys Gln Asn
                165                 170                 175
```

```
Asn Gly Trp Ser His Ile Asp Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Ser Lys Ser Gly Gly Thr Met Val Cys Thr His
                245                 250                 255

<210> SEQ ID NO 8
<211> LENGTH: 255
<212> TYPE: PRT
<213> ORGANISM: Salmo salar

<400> SEQUENCE: 8

Met Gly Thr Thr Ala Ala Phe Leu Leu Val Leu Cys Leu Ala Ile
1               5                   10                  15

Ser His Ala Trp Asp Cys Gln Glu Val Val Asn Ile Lys Asn Leu Met
                20                  25                  30

Gln Ile Asp Ala Gly Leu Gly Gln Val Val Ala Thr Asp Thr Ser Gln
            35                  40                  45

Ile Pro Tyr Tyr Leu Val Gly Asp Lys Trp Ile Arg Leu Pro Gly Ser
    50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95

Gly Leu Leu Lys Gln Leu Asp Ala Gly Gly Glu Gln Phe Ile Val Gly
            100                 105                 110

Ala Asn Met Asn Asp Thr Pro Tyr Cys Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly Pro Phe Gly Cys Trp Ala Val Asn
145                 150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Tyr Lys Ser Ala Val Thr Met Val Cys Thr His
                245                 250                 255

<210> SEQ ID NO 9
<211> LENGTH: 1214
<212> TYPE: DNA
<213> ORGANISM: Homo sapiens
<220> FEATURE:
<221> NAME/KEY: misc_feature
<222> LOCATION: (1214)..(1214)
```

<223> OTHER INFORMATION: n is a, c, g, or t

<400> SEQUENCE: 9

| | | | | | |
|---|---|---|---|---|---|
| atgagagcca | ctgcagccgt | cctattggtc | ctctgtctcc | tgaccatcag | tcatgcatgg | 60 |
| gactgtcagg | aggtagtaaa | catcaagaat | ctgatgcaga | tcgatgcagg | actggggcaa | 120 |
| gtggttgcta | cggacacagg | tcgaatcccc | tactacctgg | taggtgataa | atggatccgt | 180 |
| ctgcctggtt | ccctgaagca | tgtcactgta | ggaccagcag | ggatctgggg | tgtcaacaag | 240 |
| gactatgcaa | tctacaagta | tgtggccggt | aactgggttc | aagctgcagg | ccttctgaaa | 300 |
| cagtggatg | ctggaggtga | acagtttatt | gtggggcta | acatgaacga | tactccatac | 360 |
| cgtctgacaa | gtagtgccac | agttggctac | aagggtccag | gctcaccct | tccatggaca | 420 |
| ggattgccag | gagctgtgaa | gtactacagc | tgcggaccct | ttgggtgctg | ggcagtcaac | 480 |
| aagaatgatg | atatctactt | aatgagtctg | aatcaagact | gccaaaacaa | ggggtggagt | 540 |
| cacattgaag | gcaagctttc | catgattgag | gtggcaactg | atggtagtgt | ctttggggtc | 600 |
| aactctgcgg | gtagtgttta | taccagagac | ggcatcacac | ccagtaaacc | agagggcacc | 660 |
| ggatggagca | atatcccaat | gggcatgctc | atgggccacg | tgacctacga | cctgggccgt | 720 |
| ctttgggtcg | tctccaagtc | tggcggcacc | atggtgtgca | cacattagcc | tcttctctgt | 780 |
| agctgaaggc | cgttcgggat | ctgtctaaag | ttcacttgcg | aactcattga | tctctctttc | 840 |
| tggaaaagcc | tttagttcat | tagttcataa | aaatccttca | ttttaaaacc | tattgctcta | 900 |
| cctattattt | tcagttcttc | aattatctta | ttgccattta | aaaaaatatc | aatgaagatg | 960 |
| ttatattttc | ttgaccactc | cttgattaac | acttcaatag | atctttgcca | tggaggctat | 1020 |
| ttaagtgtag | tgtaaactag | ggcatggtca | tgttgctcac | aatccacatg | ggttttgctg | 1080 |
| tgcttcagag | gtcatcaata | ggattggatg | gaatccttgt | cattgtttat | tatctcatta | 1140 |
| tataaacatt | tcctgcaaaa | ataaagcatt | cattttgaaa | ctattgtaaa | aaaaaaaaa | 1200 |
| aaaaaaaaaa | aaan | | | | | 1214 |

<210> SEQ ID NO 10
<211> LENGTH: 2323
<212> TYPE: DNA
<213> ORGANISM: Salmo salar

<400> SEQUENCE: 10

| | | | | | |
|---|---|---|---|---|---|
| tgtgcagggc | tataaaagcg | caaagtcttc | caatgggaca | attgaagtct | ggtgtacaac | 60 |
| caaacgtata | ctgtagatct | acatagacat | catgagagcc | actgcagccg | tcctattggt | 120 |
| cctctgtctc | ctgaccatca | gtcatggtaa | gttaccatca | tctgaaacat | gcttgatcaa | 180 |
| cttggagttg | aagttttttct | tggtatactc | tactcatatg | tctttgtctc | catagcatgg | 240 |
| gactgtcagg | aggtagtaaa | catcaagaat | ctgatgcaga | tcgatgcagg | actggggcaa | 300 |
| gtggttgcta | cggacacaag | tcaaatcccc | tactacctgg | taggtgataa | atggatccgt | 360 |
| ctgcctggtt | ccctgaagca | tatcactgta | ggaccagcag | ggatctgggg | tgtcaacaag | 420 |
| gactatgcaa | tctacaagta | tgtggccggt | aactgggttc | aagctgcagg | taagtggaga | 480 |
| gcattactca | atatttatcc | agaggacacc | tgcttattag | ctttcctgat | accatcaggc | 540 |
| tgttgaaaaa | aacgattgat | gttttaaatt | gtaacttgta | ggtaatttgg | cagtactcct | 600 |
| tgtttgcttg | tctgtctgtc | tttgtggtct | tggccttctg | aaacagttgg | atgctggagg | 660 |
| tgaacagttt | attgtggggg | ctaacatgaa | cgatactcca | tactgtctga | caagtagtgc | 720 |
| cacagttggc | tacaagggtc | caggctcacc | ccttccatgg | acaggattgc | caggagctgt | 780 |

-continued

```
gaagtactac agctgcggac cctttgggtg ctgggcagtc aacaagaatg atgatatcta      840
cttaatgagt gtaagatctg ggaaagagtg ggagagctgg agtagagtag tagaggatgg      900
agagtgtcag ttattttaaa actgtttcat attataactg ttgaaattgt cctaaaaccc      960
tgattgtatc attttgtttc cagctgaatc aagactgcca aaacaagggg tggagtcaca     1020
ttgaaggcaa gctttccatg attgaggtgg caactgatgg tagtgtcttt ggggtcaact     1080
ctgcgggtag tgtttatacc caggtaaggt tgctactgaa ctatgtgtat ggtccaccac     1140
cccccccccc ccaacagtat taacttgaaa atgacttgta ataataactt agaataataa     1200
tggtataccc tttaattata actctgatcc ttacagtaca tgctatgtga atctccttac     1260
acaaaaacta atattgtag gtacataaat aaaatcagtt aaatataatc agatctaaac      1320
ttataggact tattaagaaa tgtgtagaca gtgtatgata aaatatgtaa aagttggatg     1380
tcctgtaaag ctacagtttg ggataaaaaa caacaacttc ccagacaccc caccacttgt     1440
tctggtaaac agctgaggaa tgtagttaga gaaatgtaac cactctcaca ttcatacatg     1500
gagctacgga tgcaaagaca caacaatttt tttattaaaa aaaaaaaaat gtttatattt     1560
tcttttaaag ctaaacattg tttgtttaca ataacattgt ttacaaacaa ttgagtaaaa     1620
gcttacattt tggcttctaa tgtggttgaa taaagctcaa gatgcagaag ttatattctt     1680
caaaaatcta tggctatatt taattattaa agtccaaaaa tggatgtact taaaaaaaat     1740
ggataagctt taaacatga accccaaccc tttcttcaac acagagacgg catcacagcc      1800
agtaaaccag agggcaccgg atggagcaat atcccaatgg gcatgctcat gggccacgtg     1860
acctacgacc tgggccgtct ttgggtcgtc tccaagtctg gcggcaccat ggtgtgcaca     1920
cattagcctc ttctctgtag ctgaaggccg ttcgggatct gtctaaagtt cacttgcgaa     1980
ctcattgatc tctctttctg gaaaagcctt tagttcatta gttcataaaa atccttcatt     2040
ttaaaaccta ttgctctacc tattattttc agttcttcaa ttatcttatt gccatttaaa     2100
aaaatatcaa tgaagatgtt atattttctt gaccactcct tgattaacac ttcaatagat     2160
ctttgccatg gaggctattt aagtgtagtg taaactaggg cacggtcatg ttgctcacaa     2220
tccacatggg ttttgctgtg cttcagaggt catcaatagg atttgacgga atccttgtca     2280
ttgtttatta tctcattata taatcatttc ctgcaaaaat aaa                       2323
```

<210> SEQ ID NO 11
<211> LENGTH: 765
<212> TYPE: DNA
<213> ORGANISM: Salmo salar

<400> SEQUENCE: 11

```
atgagagcca ctgcagccgt cctattggtc ctctgtctcc tgaccatcag tcatgcatgg       60
gactgtcagg aggtagtaaa catcaagaat ctgatgcaga tcgatgcagg actggggcaa      120
gtggttgcta cggacacaag tcaaatcccc tactacctgg taggtgataa atggatccgt      180
ctgcctggtt ccctgaagca tatcactgta ggaccagcag ggatctgggg tgtcaacaag      240
gactatgcaa tctacaagta tgtggccggt aactgggttc aagctgcagg ccttctgaaa      300
cagttggatg ctggaggtga acagtttatt gtgggggcta catgaacga tactccatac       360 tgtctgacaa gtagtgccac agttggctac aagggtccag gctcacccct tccatggaca      420
ggattgccag gagctgtgaa gtactacagc tgcggaccct ttgggtgctg gcagtcaac      480 aagaatgatg atatctactt aatgagtctg aatcaagact gccaaaacaa ggggtggagt      540
```

```
cacattgaag gcaagctttc catgattgag gtggcaactg atggtagtgt ctttggggtc        600
aactctgcgg gtagtgttta taccagagac ggcatcacag ccagtaaacc agagggcacc        660
ggatggagca atatcccaat gggcatgctc atgggccacg tgacctacga cctgggccgt        720
ctttgggtcg tctccaagtc tggcggcacc atggtgtgca cacat                       765

<210> SEQ ID NO 12
<211> LENGTH: 683
<212> TYPE: DNA
<213> ORGANISM: Salmo salar

<400> SEQUENCE: 12
actggggcaa gtggttgcta cggacacaag tcaaatcccc tactacctgg taggtgataa        60
atggatccgt ctgcctggtt ccctgaagca tatcactgta ggaccagcag ggatctgggg       120
tgtcaacaag gactatgcaa tctacaagta tgtggccggt aactgggttc aagctgcagg       180
cgttccgaaa cagttggatg ctggaggtaa ccagtttgtt gtgggggcta acatggacga       240
tactccattt tgtctgacaa gtagtgccac agttggctac aagggtccag gctcacccct       300
tccatggaca ggattgccag gagctgtgaa gtactacagc tgcggacact ttgggtgctg       360
ggcagtcaac aagaatgatg atattttctt aatgagtctg aatcaagact gccaaaacaa       420
cgggtggagt cacattgatg gcaagctttc catgattgag gtggcaactg atggtagtgt       480
ctttggggtc aactctgcgg gtagtgttta taccagagac ggcatcacag ccagtaaacc       540
agagggcacc ggatggagca atatcccaat gggcatgctc atgggccacg tgacctacga       600
cctgggccgt ctttgggtcg tctccaagtc tggcggcacc atggtgtgca cacattagcc       660
tcttctctgt agctgaaggc cgt                                               683

<210> SEQ ID NO 13
<211> LENGTH: 488
<212> TYPE: DNA
<213> ORGANISM: Gadus morhua

<400> SEQUENCE: 13
caatccccta ctacctggta ggtgataaat ggatccgtct gcctggttcc ctgaagcata        60
tcactgtagg accagcaggg atctggggtg tcaacaagga ctatgcaatc tacaagtatg       120
tggccggtaa ctgggttcaa gctgcaggcc ttctgaaaca gttggatgct ggaggtgaac       180
agtttattgt gggggctaac atgaacgata ctccatactg tctgacaagt agtgccacag       240
ttggctacaa gggtccaggc tcacccttc atggacagg attgccagga gctgtgaagt         300
actacagctg cggaccctt gggtgctggg cagtcaacaa gaatgatgat atctacttaa         360
tgagtctgaa tcaagactgc aaaacaagg gtggagtca cattgaaggc aagctttcca        420
tgattgaggt ggcaactgat ggtagtgtct ttggggtcaa ctctgcgggt agtgtttata       480
ccagagac                                                                488

<210> SEQ ID NO 14
<211> LENGTH: 626
<212> TYPE: DNA
<213> ORGANISM: Gallus gallus

<400> SEQUENCE: 14
caggactggg gcaagtggtt gctacggaca caagtcaaat cccctactac ctggtaggtg        60
ataaatggat ccgtctgcct ggttccctga agcatatcac tgtaggacca gcagggatct       120
ggggtgtcaa caaggactat gcaatctaca gtatgtggc cggtaactgg gttcaagctg        180
```

```
caggccttct gaaacagttg gatgctggag gtgaacagtt tattgtgggg gctaacatga    240
acgatactcc atactgtctg acaagtagtg ccacagttgg ctacaagggt ccaggctcac    300
cccttccatg gacaggattg ccaggagctg tgaagtacta cagctgcgga cgctttgggt    360
gctgggcagt caacaagaat gatgatatct acttaatgag tctgaatcaa gactgccaaa    420
acaaggggtg gagtcacatt gaaggcaagc tttccatgat tgaggtggca actgatggta    480
gtgtctttgg ggtcaactct gcgggtagtg tttataccag agacggcatc acagccgtaa    540
accagagggc accggatgga gcaatatccc aatgggcatg ctcatgggcc acgtgaccta    600
cgacctgggc cgtctttggg tcgtct                                         626
```

<210> SEQ ID NO 15
<211> LENGTH: 1089
<212> TYPE: DNA
<213> ORGANISM: Danio rerio
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1078)..(1078)
<223> OTHER INFORMATION: n is a, c, g, or t

<400> SEQUENCE: 15

```
nnaaaannta aaatanngta ggtacannnn aaatcagtta aatataatca gatntaaant      60
tntaggacta ttaagaaatg tgtagacagc gtacgataaa atatgtaaaa gttggatgtc     120
ctgtaaagct acagtttggg ataaaaaaca acaacttncc agacacccca ccacttgttn     180
tggtaaacag ntgaggaatg tagttagaga aatgtaacca ntctcacatt catacatgga     240
gttacggatg caaagacaca acaatttttt gtttacattn ttttttaacat gttttttaaa     300
gcaatacaca ttgtttgttt acaataacat tgtttacaaa caattgagta aaagcttaca     360
ttttggcttc tgtgtggttg aaataaagct caagaggcag aagttatatt cttcaaaaat     420
caatggctat atttaattat taaagttcca aaaaggatgt acttaataaa atggataagc     480
tttaaaacat gaaccccaac cctttcttca acacagagac ggcatcacag ccagtaaacc     540
agagggcacc ggatggagca atatcccaat gtgtatgctc atgggccacg tgacctacga     600
cctgggccgt ctttgggtcg tctccaagtc tgccgtcacc atggtgtgca cacattagcc     660
tcttctctgt agctgaaggc cgttcggat ccgtccaaag ttccctggcg aactcattga     720
tctctctttc tggaaaagcc tttagttcat aaaaatcctt cattttaaaa cctattgctc     780
tacctattat tttcagttct tcaatgatct tattgacatt taaaaaaaat atcattgaag     840
attttatatt ttcttgacaa ctcctagatt aacacttcaa tagacctttg ccatggaggc     900
tatttaagtg tagtgtaaac tagggcacgg tcatgttgct cacaatccac atgggttttg     960
ctgtgcttca aggtcatca ataaatcact agtgcggccg cctgcaggtc gaccatatgg    1020
gagagctccc aacgcgtngg atgcataagc gaccatatgg gagagctccc aacgcgtngg    1080
atgcataag                                                            1089
```

```
<210> SEQ ID NO 16
<211> LENGTH: 38
<212> TYPE: DNA
<213> ORGANISM: Artificial sequence
<220> FEATURE:
<223> OTHER INFORMATION: NWA15dPET(#23):  NcoI

<400> SEQUENCE: 16
gcaccatggc catgggctgg gactgtcagg aggtagta                              38

<210> SEQ ID NO 17
<211> LENGTH: 36
<212> TYPE: DNA
<213> ORGANISM: Artificial sequence
<220> FEATURE:
<223> OTHER INFORMATION: CH.A15dPET(#13):  ACC65I

<400> SEQUENCE: 17
ccgaagcttg gtaccatgtg tgcacaccat ggtgac                                36

<210> SEQ ID NO 18
<211> LENGTH: 17
<212> TYPE: PRT
<213> ORGANISM: Artificial sequence
<220> FEATURE:
<223> OTHER INFORMATION: Leukolectin consensus 1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
```

```
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 18

Xaa Trp Xaa Xaa Leu Pro Gly Xaa Leu Lys Xaa Xaa Xaa Val Gly Pro
1               5                   10                  15

Xaa

<210> SEQ ID NO 19
<211> LENGTH: 13
<212> TYPE: PRT
<213> ORGANISM: Artificial sequence
<220> FEATURE:
<223> OTHER INFORMATION: Leukolectin consensus 2
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 19

Gly Val Asn Lys Asn Asp Xaa Xaa Tyr Xaa Leu Val Gly
1               5                   10

<210> SEQ ID NO 20
<211> LENGTH: 23
<212> TYPE: DNA
<213> ORGANISM: Artificial sequence
<220> FEATURE:
<223> OTHER INFORMATION: Zebrafish LLF1

<400> SEQUENCE: 20
atgcagatcg atgcaggact ggg                                          23

<210> SEQ ID NO 21
<211> LENGTH: 24
<212> TYPE: DNA
<213> ORGANISM: Artificial sequence
<220> FEATURE:
<223> OTHER INFORMATION: Zebrafish LLF2

<400> SEQUENCE: 21
tggttccctg aagcatgtca ctgt                                         24

<210> SEQ ID NO 22
<211> LENGTH: 24
<212> TYPE: DNA
<213> ORGANISM: Artificial sequence
<220> FEATURE:
<223> OTHER INFORMATION: Zebrafish LLR1

<400> SEQUENCE: 22
gaaagagaga tcaatgagtt cgca                                         24

<210> SEQ ID NO 23
```

```
<211> LENGTH: 25
<212> TYPE: DNA
<213> ORGANISM: Artificial sequence
<220> FEATURE:
<223> OTHER INFORMATION: Zebrafish LLR2

<400> SEQUENCE: 23
caaagacact accatcagtt gccac                                          25

<210> SEQ ID NO 24
<211> LENGTH: 24
<212> TYPE: DNA
<213> ORGANISM: Artificial sequence
<220> FEATURE:
<223> OTHER INFORMATION: Zebrafish LLR3

<400> SEQUENCE: 24
gtccgcagct gtagtacttc acag                                           24

<210> SEQ ID NO 25
<211> LENGTH: 23
<212> TYPE: DNA
<213> ORGANISM: Artificial sequence
<220> FEATURE:
<223> OTHER INFORMATION: GeneRacer 5' primer

<400> SEQUENCE: 25
cgactggagc acgaggacac tga                                            23

<210> SEQ ID NO 26
<211> LENGTH: 26
<212> TYPE: DNA
<213> ORGANISM: Artificial sequence
<220> FEATURE:
<223> OTHER INFORMATION: GeneRacer 5' Nested primer

<400> SEQUENCE: 26
ggacactgac atggactgaa ggagta                                         26

<210> SEQ ID NO 27
<211> LENGTH: 25
<212> TYPE: DNA
<213> ORGANISM: Artificial sequence
<220> FEATURE:
<223> OTHER INFORMATION: Zebrafish LLR4

<400> SEQUENCE: 27
agcctggacc cttgtagcca actgt                                          25

<210> SEQ ID NO 28
<211> LENGTH: 25
<212> TYPE: DNA
<213> ORGANISM: Artificial sequence
<220> FEATURE:
<223> OTHER INFORMATION: GeneRacer 3' primer

<400> SEQUENCE: 28
gctgtcaacg atacgctacg taacg                                          25

<210> SEQ ID NO 29
<211> LENGTH: 23
<212> TYPE: DNA
<213> ORGANISM: Artificial sequence
<220> FEATURE:
<223> OTHER INFORMATION: GeneRacer 3' Nested primer

<400> SEQUENCE: 29
```

```
cgctacgtaa cggcatgaca gtg                                              23
```

<210> SEQ ID NO 30
<211> LENGTH: 27
<212> TYPE: DNA
<213> ORGANISM: Artificial sequence
<220> FEATURE:
<223> OTHER INFORMATION: Zebrafish LLF4

<400> SEQUENCE: 30

```
gtgaggtggc aactgatggt agtgtct                                          27
```

<210> SEQ ID NO 31
<211> LENGTH: 29
<212> TYPE: DNA
<213> ORGANISM: Artificial sequence
<220> FEATURE:
<223> OTHER INFORMATION: Salmon LL/F

<400> SEQUENCE: 31

```
tacggacaca ggtcgaatcc cctactacc                                        29
```

<210> SEQ ID NO 32
<211> LENGTH: 25
<212> TYPE: DNA
<213> ORGANISM: Artificial sequence
<220> FEATURE:
<223> OTHER INFORMATION: Salmon LL/R

<400> SEQUENCE: 32

```
acagagaaga ggctaatgtg tgcac                                            25
```

<210> SEQ ID NO 33
<211> LENGTH: 22
<212> TYPE: PRT
<213> ORGANISM: Salmo salar

<400> SEQUENCE: 33

Trp Asp Cys Gln Glu Val Val Asn Ile Lys Asn Leu Met Gln Ile Asp
1               5                   10                  15

Ala Gly Leu Gly Gln Val
            20

<210> SEQ ID NO 34
<211> LENGTH: 18
<212> TYPE: PRT
<213> ORGANISM: Salmo salar

<400> SEQUENCE: 34

Met Arg Ala Thr Ala Val Leu Leu Val Leu Cys Leu Leu Thr Ile Ser
1               5                   10                  15

His Ala

<210> SEQ ID NO 35
<211> LENGTH: 78
<212> TYPE: PRT
<213> ORGANISM: Salmo salar

<400> SEQUENCE: 35

Trp Asp Cys Gln Glu Val Val Asn Ile Lys Asn Leu Met Gln Ile Asp
1               5                   10                  15

Ala Gly Leu Gly Gln Val Val Ala Thr Asp Thr Ser Gln Ile Pro Tyr
            20                  25                  30

```
Tyr Leu Val Gly Asp Lys Trp Ile Arg Leu Pro Gly Ser Leu Lys His
        35                  40                  45

Ile Thr Val Gly Pro Ala Gly Ile Trp Gly Val Asn Lys Asp Tyr Ala
 50                  55                  60

Ile Tyr Lys Tyr Val Ala Gly Asn Trp Val Gln Ala Gly
 65                  70                  75
```

<210> SEQ ID NO 36
<211> LENGTH: 73
<212> TYPE: PRT
<213> ORGANISM: Salmo salar

<400> SEQUENCE: 36

```
Gly Leu Leu Lys Gln Leu Asp Ala Gly Gly Glu Gln Phe Ile Val Gly
 1               5                  10                  15

Ala Asn Met Asn Asp Thr Pro Tyr Cys Leu Thr Ser Ser Ala Thr Val
                20                  25                  30

Gly Tyr Lys Gly Pro Gly Ser Pro Leu Pro Trp Thr Gly Leu Pro Gly
        35                  40                  45

Ala Val Lys Tyr Tyr Ser Cys Gly Pro Phe Gly Cys Trp Ala Val Asn
 50                  55                  60

Lys Asn Asp Asp Ile Tyr Leu Met Ser
 65                  70
```

<210> SEQ ID NO 37
<211> LENGTH: 39
<212> TYPE: PRT
<213> ORGANISM: Salmo salar

<400> SEQUENCE: 37

```
Leu Asn Gln Asp Cys Gln Asn Lys Gly Trp Ser His Ile Glu Gly Lys
 1               5                  10                  15

Leu Ser Met Ile Glu Val Ala Thr Asp Gly Ser Val Phe Gly Val Asn
                20                  25                  30

Ser Ala Gly Ser Val Tyr Thr
        35
```

<210> SEQ ID NO 38
<211> LENGTH: 47
<212> TYPE: PRT
<213> ORGANISM: Salmo salar

<400> SEQUENCE: 38

```
Arg Asp Gly Ile Thr Ala Ser Lys Pro Glu Gly Thr Gly Trp Ser Asn
 1               5                  10                  15

Ile Pro Met Gly Met Leu Met Gly His Val Thr Tyr Asp Leu Gly Arg
                20                  25                  30

Leu Trp Val Val Ser Lys Ser Ala Val Thr Met Val Cys Thr His
        35                  40                  45
```

<210> SEQ ID NO 39
<211> LENGTH: 260
<212> TYPE: PRT
<213> ORGANISM: Salmo salar

<400> SEQUENCE: 39

```
Ile Tyr Arg Asp Ile Met Arg Thr Thr Ala Ala Phe Leu Leu Val Leu
 1               5                  10                  15

Cys Leu Leu Ala Ile Ser His Ala Trp Asp Cys Gln Pro Val Val Asp
```

```
                 20                  25                  30
Ile Lys Asn Leu Met Gln Ile Asp Ala Gly Leu Gly Gln Val Val Ala
             35                  40                  45

Thr Asp Thr Ser Gln Ile Pro Tyr Tyr Leu Val Gly Asp Lys Trp Ile
         50                  55                  60

Arg Met Pro Gly Ser Leu Lys His Ile Thr Val Gly Pro Ala Gly Ile
 65                  70                  75                  80

Trp Gly Val Asn Lys Asp Tyr Ala Ile Tyr Lys Tyr Val Ala Gly Asn
                 85                  90                  95

Trp Val Gln Ala Ala Gly Leu Leu Lys Gln Leu Asp Ala Gly Gly Asp
            100                 105                 110

Gln Phe Val Val Gly Ala Asn Met Asn Asp Thr Pro Phe Cys Leu Ala
            115                 120                 125

Ser Ser Ala Thr Val Gly Tyr Lys Gly Pro Gly Ser Pro Leu Pro Trp
        130                 135                 140

Thr Gly Leu Pro Gly Ser Val Lys Tyr Ser Cys Gly Pro Phe Gly
145                 150                 155                 160

Cys Trp Ala Val Asn Asn Asn Asp Asp Ile Tyr Leu Met Ser Leu Asn
                165                 170                 175

Gln Asp Cys Gln Asn Asn Gly Trp Ser His Ile Glu Gly Lys Leu Ser
            180                 185                 190

Met Ile Glu Val Ala Thr Asp Gly Ser Val Phe Gly Val Asn Ser Val
        195                 200                 205

Gly Ser Val Tyr Thr Arg Asp Gly Ile Thr Ala Ser Lys Pro Glu Gly
    210                 215                 220

Thr Gly Trp Ser His Val Pro Met Cys Met Gln Met Lys His Val Thr
225                 230                 235                 240

Tyr Asp Leu Gly Arg Leu Trp Val Ile Ser Lys Ser Gly Phe Thr Met
                245                 250                 255

Val Cys Thr His
            260

<210> SEQ ID NO 40
<211> LENGTH: 260
<212> TYPE: PRT
<213> ORGANISM: Salmo salar

<400> SEQUENCE: 40

Ile Tyr Arg Asp Ile Met Arg Ala Thr Ala Val Leu Leu Val Leu
 1               5                  10                  15

Cys Leu Leu Thr Leu Ser His Ala Trp Asp Cys Gln Ile Val Ala Asn
                 20                  25                  30

Ile Lys Asn Leu Met Gln Ile Asp Ala Gly Leu Gly Gln Val Val Ala
             35                  40                  45

Thr Asp Thr Ser Gln Ile Pro Tyr Tyr Leu Val Gly Asp Lys Trp Ile
         50                  55                  60

Arg Met Pro Gly Ser Leu Arg His Ile Thr Val Gly Pro Ala Gly Ile
 65                  70                  75                  80

Trp Gly Val Ser Asn Gly Asn Leu Met Phe Lys Tyr Val Ala Gly Asn
                 85                  90                  95

Trp Val Gln Phe Ala Thr Ser Ala Lys Gln Leu Asp Ala Gly Gly Asp
            100                 105                 110

Glu Phe Val Val Gly Asp Asn Met Asp Asp Val Pro Trp Cys Leu Ser
        115                 120                 125
```

```
Arg Ser Ala Ser Leu Gly Phe Met Gly Ala Asp Ser Ser Leu Arg Gly
130                 135                 140

Ile Met Leu Pro Gly Ala Val Lys Tyr Phe Ser Cys Gly Pro Phe Gly
145                 150                 155                 160

Cys Trp Ala Val Asn Lys Asn Asp Asp Ile Tyr Leu Met Ser Leu Asn
                165                 170                 175

Gln Asp Cys Gln Asn Lys Gly Trp Ser His Ile Glu Gly Lys Leu Ser
            180                 185                 190

Met Ile Glu Val Ala Thr Asp Gly Ser Val Phe Gly Val Asn Ser Ala
            195                 200                 205

Gly Gln Val Tyr Thr Arg Asp Gly Ile Thr Ala Ser Lys Pro Glu Gly
210                 215                 220

Thr Gly Trp Ser Asn Val Leu Met Tyr Met Pro Met Lys His Val Thr
225                 230                 235                 240

Tyr Asp Leu Gly Arg Leu Trp Val Ile Ser Asn Ser Gly Phe Thr Met
                245                 250                 255

Val Cys Lys His
            260

<210> SEQ ID NO 41
<211> LENGTH: 238
<212> TYPE: PRT
<213> ORGANISM: Cyprinus carpio

<400> SEQUENCE: 41

Leu Asp Cys Thr Val Ile Asp Gly Asn Leu Lys Gln Ile Asp Ala Gly
1               5                   10                  15

Ser Gly Ser Val Val Gly Val Asn Asn Leu Asn Glu Thr Phe Val Leu
                20                  25                  30

Ile Asp Asn Val Phe Thr Lys Ile Ser Gly Ser Leu Lys His Phe Ser
                35                  40                  45

Val Gly Pro Ala Gly Gln Leu Gly Val Asn Thr Ala Asn Asn Ile Phe
            50                  55                  60

Lys Tyr Gln Ser Gly Gly Phe Val Gln Leu Ala Gly Leu Leu Lys Gln
65                  70                  75                  80

Val Asp Ala Gly Gly Asp Gln Ile Ile Ala Gly Val Asn Met Tyr Asp
                85                  90                  95

Asp Ile Tyr Cys Leu Asn Met Asp Ala Asn Asn Lys Trp Pro Ser Ser
                100                 105                 110

Asn Thr Pro Trp Val Gln Ile Asn Gly Lys Leu Lys Tyr Tyr Ser Cys
            115                 120                 125

Gly Pro Tyr Ser Cys Trp Gly Val Asn Ser Asn Asp Gln Ile Phe Ile
130                 135                 140

Met Lys Asp Val Ser Ser Asn Val Cys Ser Gly Ser Gly Ser Phe Ile
145                 150                 155                 160

Asn Ile Pro Gly Leu Leu Ser Met Ile Glu Val Ala Thr Asp Gly Ser
                165                 170                 175

Val Phe Gly Val Asn Ser Gln Gly Asn Leu Tyr Gln Arg Thr Gly Val
            180                 185                 190

Thr Arg Ser Lys Pro Asp Gly Asp Trp Ile Ser Met Val Ala Cys
        195                 200                 205

Pro Asn Gly His Lys His Val Ser Phe Asp Leu Gly Val Leu Trp Leu
            210                 215                 220

Val Cys Val Asp Gly Ser Ile Arg Lys Cys Ile Leu Thr Asp
225                 230                 235
```

<210> SEQ ID NO 42
<211> LENGTH: 246
<212> TYPE: PRT
<213> ORGANISM: Engystomops pustulosus

<400> SEQUENCE: 42

Met Ile Leu Ile Leu Gly Val Leu Leu Gly Ala Glu Ala Ser Ala
1               5                   10                  15

Glu Thr Leu Cys Ile Pro Gly Arg Met Lys Gln Leu Asp Ala Gly Ala
            20                  25                  30

Gly Arg Val Val Ala Val Lys Ser Asn Gly Asp Val Tyr Gln Leu Leu
        35                  40                  45

Glu Asn Asn Trp Val Gln Ile Pro Gly Lys Leu Ile His Val Thr Val
50                  55                  60

Gly Pro Ala Gly Leu Trp Gly Val Asn Lys Asp Lys Asn Ile Tyr Lys
65                  70                  75                  80

Tyr Val Asp Asn Asp Trp Leu Gln Val Asp Gly Leu Leu Asn Gln Ile
                85                  90                  95

Asp Ala Gly Gly Asn Arg Phe Val Val Gly Val Asn Asp Asn Glu Asp
            100                 105                 110

Ile Phe Cys Leu Asn Gln Asp Gln Thr Thr Ser Asn Ala Val Lys Leu
        115                 120                 125

Asp Tyr Lys Gly Val Asp Gly Lys Leu Lys Tyr Tyr Ser Ser Gly Gly
    130                 135                 140

Tyr Gly Ser Trp Gly Val Asn Ala Ala Tyr Asp Ile Phe Tyr Arg Arg
145                 150                 155                 160

Asn Val His Pro Met Ser Cys Gln Gly Thr Asn Trp Glu Asn Val Glu
                165                 170                 175

Gly Lys Leu Val Met Leu Glu Val Ala Glu Asp Gly Ser Val Tyr Gly
            180                 185                 190

Val Asn Tyr Asn Gly His Val Tyr Lys Arg Glu Gly Ile Thr Ala Gly
        195                 200                 205

Asn Pro Met Gly Thr Ser Trp Thr Tyr Leu Lys Val Asp Glu Lys Val
    210                 215                 220

Arg His Val Ser Tyr Asp Arg Gly Val Leu Tyr Val Val Thr Ile Asp
225                 230                 235                 240

Asp Arg Ile Phe Arg Cys
                245

<210> SEQ ID NO 43
<211> LENGTH: 256
<212> TYPE: PRT
<213> ORGANISM: Danio rerio

<400> SEQUENCE: 43

Met Lys Val Tyr Gln Gly Val Leu Leu Leu Ser Cys Gln Ile Leu
1               5                   10                  15

Tyr Thr Leu Ala Leu Asp Cys Thr Ile Met Asn Gly Asn Leu Lys Gln
            20                  25                  30

Ile Asp Ala Gly Ser Gly Ser Val Val Gly Val Asn Asp Leu Asn Gln
        35                  40                  45

Ala Phe Val Leu Gln Asp Asp Val Phe Asn Pro Val Ser Lys Ser Leu
50                  55                  60

Lys His Phe Ser Val Gly Pro Ala Gly Gln Leu Gly Val Asn Lys Thr
65                  70                  75                  80

```
Tyr Tyr Ile Phe Lys Leu Met Ser Gly Arg Phe Val Glu Phe Pro Gly
                85                  90                  95

Leu Leu Lys Gln Val Asp Ala Gly Gly Asp Gln Ile Ile Ala Gly Val
            100                 105                 110

Asn Met Asn Asp Asp Ile Phe Cys Leu Asn Met Asp Ala Ser Asn Gln
            115                 120                 125

Trp Pro Ser Ser Thr Thr Pro Trp Val Thr Ile Asn Gly Lys Leu Lys
        130                 135                 140

Tyr Tyr Ser Cys Gly Pro Tyr Ser Cys Trp Val Asn Ser Asp Asp
145                 150                 155                 160

Tyr Ile Phe Met Met Lys Gly Val Ser Ser Asn Ala Cys Ser Gly Gly
                165                 170                 175

Gly Met Phe Val Asn Ile Pro Gly Leu Leu Ser Met Ile Glu Val Gly
            180                 185                 190

Thr Asp Gly Ser Val Phe Gly Val Asn Tyr Glu Ala Lys Leu Tyr Gln
            195                 200                 205

Arg Val Gly Val Ser Arg Ser Asn Pro Ala Gly Thr Asp Trp Ile Ser
        210                 215                 220

Met Ile Ala Cys Pro Asn Gly His Lys His Val Ser Phe Asp Leu Gly
225                 230                 235                 240

Val Leu Trp Val Val Cys Val Asp Gly Ser Ile Arg Lys Cys Thr Leu
                245                 250                 255

<210> SEQ ID NO 44
<211> LENGTH: 242
<212> TYPE: PRT
<213> ORGANISM: Ephydatia fluviatilis

<400> SEQUENCE: 44

Met Gln Gln Leu Lys Ala Ser Trp Trp Phe Ala Ala Cys Phe Ala Ala
1               5                   10                  15

Val Tyr Gly Gln Asn Trp Val Gln Ile Pro Gly Gly Leu Lys His Val
            20                  25                  30

Ser Ala Ser Val Asn Tyr Ile Trp Gly Val Asn Ser Ala Asp Gln Ile
        35                  40                  45

Tyr Arg Cys Pro Asn Pro Cys Ser Gly Glu Trp Val Gln Ile Pro Gly
    50                  55                  60

Gly Leu Lys Gln Ile Asp Ala Gly Asp Met Glu Val Trp Gly Val Asn
65                  70                  75                  80

Ser Asn Asp Asp Ile Phe Lys Arg Asn Val Asp Gly Ser Gly Asp Trp
                85                  90                  95

Ile His Leu Pro Gly Lys Leu Lys His Val Ser Ala Ser Gly Asn Gly
            100                 105                 110

Tyr Ile Trp Gly Val Asn Ser Asn Asp Asp Ile Phe Lys Cys Lys Lys
        115                 120                 125

Pro Cys Thr Gly Ala Trp Ile Gln Val Ser Gly Lys Leu Lys Gln Ile
    130                 135                 140

Asp Gly Gly Tyr Asn His Val Tyr Gly Val Asn Ser Asn Asn Asp Ile
145                 150                 155                 160

Phe Thr Leu Pro Val Asp Gly Ser Gly Ser Trp Arg His Ile Pro Gly
                165                 170                 175

Lys Leu Lys His Val Ser Ala Ser Gly Thr His Ser Val Phe Gly Thr
            180                 185                 190

Gly Pro Asp Asp Thr Ile Trp Arg Cys Arg Lys Pro Cys Val Gly Glu
```

```
                  195                 200                 205
Trp Glu Arg Ile Asp Gly Gly Leu Lys Gln Cys Asp Ala Thr Ile Asn
    210                 215                 220
Gly Leu Tyr Gly Val Asn Ser Gly Asp Ser Ile Phe Arg Ser Ala Leu
225                 230                 235                 240
Gly Leu

<210> SEQ ID NO 45
<211> LENGTH: 238
<212> TYPE: PRT
<213> ORGANISM: Suberites domuncula

<400> SEQUENCE: 45

Met Ser Lys Leu Thr Leu Leu Leu Ala Val Cys Ile Ser Ala
1               5                   10                  15

Phe Gly Gln Phe Gln Gln Ile Ser Arg Asp Met Lys His Val Ser Ala
                20                  25                  30

Ser Val Ser Tyr Leu Trp Gly Val Asp His Ser Asp Asn Ile Phe Arg
            35                  40                  45

Cys Asp Arg Pro Cys Asn Gly Lys Trp Val Gln Val Pro Gly Lys Leu
        50                  55                  60

Lys Gln Ile Asp Val Gly Asp Glu Val Trp Gly Val Asn Ser Gly
65                  70                  75                  80

Asp His Ile Tyr Lys Arg Pro Ala Asp Gly Ser Gly Ala Trp Lys Gly
                85                  90                  95

Ile Gly Gly Arg Leu Lys His Val Thr Ala Ser Gly Asn Gly Tyr Ile
            100                 105                 110

Trp Gly Val Asn Ser Gly Asp Asn Ile Tyr Lys Cys Lys Lys Pro Cys
        115                 120                 125

Asn Gly Lys Trp Ile His Val Gly Gly Lys Leu Lys Gln Ile Asp Gly
130                 135                 140

Gly His Lys Tyr Val Tyr Gly Val Asn Ser Ala Asn Gln Ile Phe Ser
145                 150                 155                 160

Arg Ala Val Asp Gly Ser Gly Asn Trp Arg His Ile Pro Gly Ser Leu
                165                 170                 175

Ala His Val Thr Ala Ser Gly Ser Asp Asp Ile Phe Gly Val Asn Lys
            180                 185                 190

Ala Gln Asn Ile Phe Arg Cys Lys Lys Pro Cys Ile Gly Glu Trp Glu
        195                 200                 205

Gln Met Glu Gly Lys Leu Asn Gln Cys Asp Ala Thr Ile Asn Gly Val
    210                 215                 220

Phe Gly Val Lys Ser Gly Thr Phe Arg His Val Ile Gly Ala
225                 230                 235

<210> SEQ ID NO 46
<211> LENGTH: 221
<212> TYPE: PRT
<213> ORGANISM: Tachypleus tridentatus

<400> SEQUENCE: 46

Val Gln Trp His Gln Ile Pro Gly Lys Leu Met His Ile Thr Ala Thr
1               5                   10                  15

Pro His Phe Leu Trp Gly Val Asn Ser Asn Gln Gln Ile Tyr Leu Cys
                20                  25                  30

Arg Gln Pro Cys Tyr Asp Gly Gly Trp Thr Gln Ile Ser Gly Ser Leu
            35                  40                  45
```

```
Lys Gln Val Asp Ala Asp Asp His Glu Val Trp Gly Val Asn Arg Asn
         50                   55                   60

Asp Asp Ile Tyr Lys Arg Pro Val Asp Gly Ser Gly Ser Trp Val Arg
 65                   70                   75                   80

Val Ser Gly Lys Leu Lys His Val Ser Ala Ser Gly Tyr Gly Tyr Ile
                     85                   90                   95

Trp Gly Val Asn Ser Asn Asp Gln Ile Tyr Lys Cys Pro Lys Pro Cys
                    100                  105                  110

Asn Gly Ala Trp Thr Gln Val Asn Gly Arg Leu Lys Gln Ile Asp Gly
                    115                  120                  125

Gly Gln Ser Met Val Tyr Gly Val Asn Ser Ala Asn Ala Ile Tyr Arg
                    130                  135                  140

Arg Pro Val Asp Gly Ser Gly Ser Trp Gln Gln Ile Ser Gly Ser Leu
145                  150                  155                  160

Lys His Ile Thr Gly Ser Gly Leu Ser Glu Val Phe Gly Val Asn Ser
                    165                  170                  175

Asn Asp Gln Ile Tyr Arg Cys Thr Lys Pro Cys Ser Gly Gln Trp Ser
                    180                  185                  190

Leu Ile Asp Gly Arg Leu Lys Gln Cys Asp Ala Thr Gly Asn Thr Ile
                    195                  200                  205

Val Gly Val Asn Ser Val Asp Asn Ile Tyr Arg Ser Gly
                    210                  215                  220

<210> SEQ ID NO 47
<211> LENGTH: 256
<212> TYPE: PRT
<213> ORGANISM: Tachypleus tridentatus

<400> SEQUENCE: 47

Met Lys Asn Ile Met Tyr Phe Ser Leu Val Thr Leu Leu Leu Thr Phe
 1                    5                   10                   15

Leu Val Val Ser Pro Thr Leu Ala Glu Trp Thr His Ile Asn Gly Lys
                     20                   25                   30

Leu Ser His Leu Thr Val Thr Pro Arg Phe Val Trp Gly Val Asn Asn
                     35                   40                   45

Val His Asp Ile Phe Arg Cys Thr Arg Pro Cys Thr Gly Ser Asn Trp
 50                   55                   60

Ile Lys Val Glu Gly Ser Leu Lys Gln Ile Asp Ala Asp Asp His Glu
 65                   70                   75                   80

Val Trp Gly Val Asn Ser Asn Asp Asn Ile Tyr Lys Arg Pro Val Asp
                     85                   90                   95

Gly Asn Gly Ser Trp Ile Gln Ile Lys Gly Leu Lys His Val Ser
                    100                  105                  110

Ala Ser Gly Tyr Gly Tyr Ile Trp Gly Val Asn Ser Lys Asp Gln Ile
                    115                  120                  125

Phe Lys Cys Pro Lys Pro Cys Asn Gly Glu Trp Glu Leu Val Asp Gly
                    130                  135                  140

Ser Leu Lys Gln Val Asp Gly Arg Asp Leu Val Tyr Gly Val Thr
145                  150                  155                  160

Gln Asn Asp Glu Ile Phe Arg Arg Pro Val Asp Gly Ser Gly Val Trp
                    165                  170                  175

Val Asn Ile Pro Gly Lys Leu Lys His Ile Ser Gly Ser Gly Ser Trp
                    180                  185                  190

Glu Val Phe Gly Val Asn Cys Asn Asp Gln Ile Phe Arg Cys Lys Lys
```

```
                195                 200                 205

Pro Cys Ser Gly Gln Trp Val Arg Leu Ser Gly Tyr Leu Lys Gln Cys
    210                 215                 220

Asp Ala Ser Gly Asp Ser Leu Leu Gly Val Asn Ser Asn Asp Asp Ile
225                 230                 235                 240

Phe Glu Ser Val Pro Ala Ser Lys Ser Cys Trp Met Asn Pro Phe Leu
                245                 250                 255

<210> SEQ ID NO 48
<211> LENGTH: 203
<212> TYPE: PRT
<213> ORGANISM: Tachypleus tridentatus

<400> SEQUENCE: 48

Gln Trp His Gln Ile Pro Gly Lys Leu Met His Ile Thr Ala Thr Pro
1               5                   10                  15

His Phe Leu Trp Gly Val Asn Ser Asn Gln Gln Ile Tyr Leu Cys Arg
                20                  25                  30

Gln Pro Cys Tyr Asp Gly Gln Trp Thr Gln Ile Ser Gly Ser Leu Lys
            35                  40                  45

Gln Val Asp Ala Asp Asp His Glu Val Trp Gly Val Asn Arg Asn Asp
50                  55                  60

Asp Ile Tyr Lys Arg Pro Val Asp Gly Ser Gly Thr Trp Val Arg Val
65                  70                  75                  80

Ser Gly Lys Leu Lys His Val Ser Ala Ser Gly Tyr Gly Tyr Ile Trp
                85                  90                  95

Gly Val Asn Ser Asn Asp Gln Ile Tyr Lys Cys Pro Lys Pro Cys Asn
                100                 105                 110

Gly Ala Trp Thr Gln Val Asn Gly Arg Leu Lys Gln Ile Asp Gly Gly
            115                 120                 125

Gln Ser Met Val Tyr Gly Val Asn Ser Ala Asn Ala Ile Tyr Arg Arg
130                 135                 140

Pro Val Asp Gly Ser Gly Ser Trp Gln Gln Ile Ser Gly Ser Leu Lys
145                 150                 155                 160

His Ile Thr Gly Ser Gly Ile Ser Glu Val Phe Gly Val Asn Ser Asn
                165                 170                 175

Asp Gln Ile Tyr Arg Cys Thr Lys Pro Cys Ser Gly Gln Trp Ser Leu
            180                 185                 190

Ile Asp Gly Lys Leu Lys Gln Cys Asp Ala Thr
            195                 200

<210> SEQ ID NO 49
<211> LENGTH: 217
<212> TYPE: PRT
<213> ORGANISM: Physarum polycephalum

<400> SEQUENCE: 49

Met Val His Trp Glu Lys His Glu Gly Glu Leu Ser Val Val Gly Val
1               5                   10                  15

Gly Ala Gly Ser Asn Asp Ile Trp Gly Val Asn His Leu Gly His Ile
                20                  25                  30

Tyr His Trp Asp Gly His Lys Trp His Lys Val Asp Gly Glu Leu Thr
            35                  40                  45

Asn Ile Ser Val Gly His Asp Gly Glu Val Trp Gly Val Asn Lys Asn
50                  55                  60

His Asn Ile Tyr Arg Leu Asp Arg Ser Asn Asn Lys Trp Thr Gln Ile
```

```
                65                  70                  75                  80
Pro Gly Glu Leu Val Gln Val Ser Val Gly Ser His His His Val Trp
                    85                  90                  95

Gly Val Asn His Leu Asp His Ile Tyr Lys Trp Asp His His His Asn
                100                 105                 110

Lys Trp Asp Lys Ile Asp Gly Ala Leu Thr Asn Val Ser Val Gly Lys
                115                 120                 125

Asp Gly Thr Val Tyr Gly Val Asn Arg Gly His Gln Ile Tyr Arg Trp
        130                 135                 140

Asp Gly Ser Lys Val Asp Leu Val Leu Gly Glu Leu Val Gln Ile His
145                 150                 155                 160

Val Ser Asp Ala Glu Lys Ile Val Gly Val Asn His Leu Asp His Ile
                165                 170                 175

Tyr Arg Leu Lys His Gly Lys Asp Trp Glu Lys Leu Asp Gly Glu Leu
                180                 185                 190

Thr Trp Val Ser Val Gly His His Gly Glu Val Trp Gly Val Asn Lys
                195                 200                 205

Leu His His Ile Tyr Lys Ala Thr Leu
        210                 215

<210> SEQ ID NO 50
<211> LENGTH: 261
<212> TYPE: PRT
<213> ORGANISM: Danio rerio

<400> SEQUENCE: 50

Met Tyr Cys Gly Ala Met Lys Val Tyr Gln Gly Val Leu Leu Leu Leu
1               5                   10                  15

Ser Cys Gln Ile Leu Tyr Thr Leu Ala Leu Asp Cys Thr Ile Met Asn
                20                  25                  30

Gly Asn Leu Lys Gln Ile Asp Ala Gly Ser Gly Ser Val Val Gly Val
            35                  40                  45

Asn Asp Leu Asn Gln Ala Phe Val Leu Gln Asp Val Phe Asn Pro
 50                  55                  60

Val Ser Lys Ser Leu Lys His Phe Ser Val Gly Pro Ala Gly Gln Leu
65                  70                  75                  80

Gly Val Asn Gly Thr Tyr Tyr Ile Phe Lys Leu Met Ser Gly Arg Phe
                85                  90                  95

Val Gln Phe Pro Gly Leu Leu Lys Gln Val Asp Ala Gly Gly Asp Gln
                100                 105                 110

Ile Ile Ala Gly Val Asn Met Asn Asp Asp Ile Phe Cys Leu Asn Met
            115                 120                 125

Asp Ala Asn Asn Gln Trp Pro Ser Ser Thr Thr Pro Trp Val Thr Leu
        130                 135                 140

Asn Gly Lys Leu Lys Tyr Tyr Ser Cys Gly Pro Tyr Ser Cys Cys Gly
145                 150                 155                 160

Val Asn Ser Ala Asp Arg Ile Phe Ile Met Lys Gly Val Ser Ser Asn
                165                 170                 175

Ala Cys Ser Gly Asp Gly Thr Phe Val Asn Ile Pro Gly Leu Leu Ser
                180                 185                 190

Met Ile Glu Val Gly Thr Asp Gly Ser Val Phe Gly Val Asn Tyr Glu
            195                 200                 205

Ala Lys Leu Phe Gln Arg Val Gly Val Ser Arg Ser Asn Pro Ala Gly
        210                 215                 220
```

```
Thr Asp Trp Ile Ser Met Ile Ala Cys Pro Ile Gly His Lys His Val
225                 230                 235                 240

Ser Leu Asp Leu Gly Val Leu Trp Val Val Cys Val Asp Gly Ser Ile
            245                 250                 255

Arg Lys Cys Thr Leu
            260

<210> SEQ ID NO 51
<211> LENGTH: 255
<212> TYPE: PRT
<213> ORGANISM: Carassius auratus

<400> SEQUENCE: 51

Met Lys Val Cys Arg Ser Val Leu Leu Phe Cys Cys Gln Phe Phe
1               5                   10                  15

His Thr Leu Ala Leu Asn Cys Asn Val Val Asn Gly Asn Leu Lys Gln
                20                  25                  30

Ile Asp Ala Gly Ser Gly Ser Val Val Gly Val Asn Asn Asn Asn Glu
            35                  40                  45

Ile Phe Val Leu Ile Asp Asn Ile Phe Thr Lys Ile Ser Gly Ser Leu
50                  55                  60

Lys His Phe Ser Val Gly Pro Ala Gly Gln Leu Gly Val Asn Thr Ala
65                  70                  75                  80

Asn Asn Ile Phe Arg Phe Gln Ser Gly Gly Phe Val Arg Leu Glu Gly
                85                  90                  95

Leu Leu Asn Gln Val Asp Ala Gly Gly Asp Gln Ile Ile Ala Gly Val
            100                 105                 110

Asn Met Tyr Asp Asp Ile Phe Cys Ser Asn Met Asp Ala Asn Asn Lys
        115                 120                 125

Trp Leu Ser Ser Asn Ile Pro Trp Ile Asn Ile Gly Gly Lys Leu Lys
130                 135                 140

Tyr Tyr Ser Cys Gly Pro Tyr Ser Cys Trp Gly Val Asn His Asn Asp
145                 150                 155                 160

Gln Ile Phe Ile Met Lys Asp Val Ser Ser Val Cys Ser Gly Ser
                165                 170                 175

Gly Ser Phe Val Asn Ile Pro Gly Leu Leu Ser Met Ile Glu Val Ala
            180                 185                 190

Thr Asp Gly Ser Val Tyr Gly Val Asn Ser Gln Gly Ser Leu Phe Lys
        195                 200                 205

Arg Thr Gly Val Thr Arg Cys Thr Pro Asp Gly Thr Asp Trp Ile Pro
210                 215                 220

Val Val Ala Cys Pro Asn Gly His Gln His Val Ser Phe Asp Leu Gly
225                 230                 235                 240

Val Leu Trp Val Val Cys Val Asp Gly Ser Ile Arg Lys Cys Ser
            245                 250                 255

<210> SEQ ID NO 52
<211> LENGTH: 238
<212> TYPE: PRT
<213> ORGANISM: Cyprinus carpio

<400> SEQUENCE: 52

Leu Asp Cys Thr Val Ile Asp Gly Asn Leu Lys Gln Ile Asp Ala Gly
1               5                   10                  15

Ser Gly Ser Val Val Gly Val Asn Asn Leu Asn Glu Thr Phe Val Leu
            20                  25                  30
```

```
Ile Asp Asn Val Phe Thr Lys Ile Ser Gly Ser Leu Lys His Phe Ser
         35                  40                  45

Val Gly Pro Ala Gly Gln Leu Gly Val Asn Thr Ala Asn Asn Ile Phe
 50                  55                  60

Lys Tyr Gln Ser Gly Gly Phe Val Gln Leu Ala Gly Leu Leu Lys Gln
 65                  70                  75                  80

Val Asp Ala Gly Gly Asp Gln Ile Ile Ala Gly Val Asn Met Tyr Asp
                 85                  90                  95

Asp Ile Tyr Cys Leu Asn Met Asp Ala Asn Asn Lys Trp Pro Ser Ser
                100                 105                 110

Asn Thr Pro Trp Val Gln Ile Asn Gly Lys Leu Lys Tyr Tyr Ser Cys
            115                 120                 125

Gly Pro Tyr Ser Cys Trp Gly Val Asn Ser Asn Asp Gln Ile Phe Ile
        130                 135                 140

Met Lys Asp Val Ser Ser Asn Val Cys Ser Gly Ser Gly Ser Phe Ile
145                 150                 155                 160

Asn Ile Pro Gly Leu Leu Ser Met Ile Glu Val Ala Thr Asp Gly Ser
                165                 170                 175

Val Phe Gly Val Asn Ser Gln Gly Asn Leu Tyr Gln Arg Thr Gly Val
            180                 185                 190

Thr Arg Ser Lys Pro Asp Gly Thr Asp Trp Ile Ser Met Val Ala Cys
        195                 200                 205

Pro Asn Gly His Lys His Val Ser Phe Asp Leu Gly Val Leu Trp Leu
    210                 215                 220

Val Cys Val Asp Gly Ser Ile Arg Lys Cys Ile Leu Thr Asp
225                 230                 235

<210> SEQ ID NO 53
<211> LENGTH: 36
<212> TYPE: PRT
<213> ORGANISM: Homo sapiens

<400> SEQUENCE: 53

Trp Asp Cys Gln Glu Val Val Asn Ile Lys Asn Leu Met Gln Ile Asp
 1               5                  10                  15

Ala Gly Leu Gly Gln Val Val Ala Thr Asp Thr Gly Arg Ile Pro Tyr
                20                  25                  30

Tyr Leu Val Gly
        35

<210> SEQ ID NO 54
<211> LENGTH: 34
<212> TYPE: PRT
<213> ORGANISM: Homo sapiens

<400> SEQUENCE: 54

Asp Lys Trp Ile Arg Leu Pro Gly Ser Leu Lys His Val Thr Val Gly
 1               5                  10                  15

Pro Ala Gly Ile Trp Gly Val Asn Lys Asp Tyr Ala Ile Tyr Lys Tyr
                20                  25                  30

Val Ala

<210> SEQ ID NO 55
<211> LENGTH: 35
<212> TYPE: PRT
<213> ORGANISM: Homo sapiens

<400> SEQUENCE: 55
```

```
Gly Asn Trp Val Gln Ala Ala Gly Leu Leu Lys Gln Leu Asp Ala Gly
1               5                   10                  15

Gly Glu Gln Phe Ile Val Gly Ala Asn Met Asn Asp Thr Pro Tyr Arg
            20                  25                  30

Leu Thr Ser
        35

<210> SEQ ID NO 56
<211> LENGTH: 34
<212> TYPE: PRT
<213> ORGANISM: Homo sapiens

<400> SEQUENCE: 56

Leu Pro Trp Thr Gly Leu Pro Gly Ala Val Lys Tyr Tyr Ser Cys Gly
1               5                   10                  15

Pro Phe Gly Cys Trp Ala Val Asn Lys Asn Asp Asp Ile Tyr Leu Met
            20                  25                  30

Ser Leu

<210> SEQ ID NO 57
<211> LENGTH: 35
<212> TYPE: PRT
<213> ORGANISM: Homo sapiens

<400> SEQUENCE: 57

Lys Gly Trp Ser His Ile Glu Gly Lys Leu Ser Met Ile Glu Val Ala
1               5                   10                  15

Thr Asp Gly Ser Val Phe Gly Val Asn Ser Ala Gly Ser Val Tyr Thr
            20                  25                  30

Arg Asp Gly
        35

<210> SEQ ID NO 58
<211> LENGTH: 34
<212> TYPE: PRT
<213> ORGANISM: Cyprinus carpio

<400> SEQUENCE: 58

Leu Asp Cys Thr Val Ile Asp Gly Asn Leu Lys Gln Ile Asp Ala Gly
1               5                   10                  15

Ser Gly Ser Val Val Gly Val Asn Asn Leu Asn Glu Thr Phe Val Leu
            20                  25                  30

Ile Asp

<210> SEQ ID NO 59
<211> LENGTH: 34
<212> TYPE: PRT
<213> ORGANISM: Cyprinus carpio

<400> SEQUENCE: 59

Asn Val Phe Thr Lys Ile Ser Gly Ser Leu Lys His Phe Ser Val Gly
1               5                   10                  15

Pro Ala Gly Gln Leu Gly Val Asn Thr Ala Asn Asn Ile Phe Lys Tyr
            20                  25                  30

Gln Ser

<210> SEQ ID NO 60
<211> LENGTH: 35
<212> TYPE: PRT
```

<210> SEQ ID NO 61
<211> LENGTH: 34
<212> TYPE: PRT
<213> ORGANISM: Cyprinus carpio

<400> SEQUENCE: 60

Gly Gly Phe Val Gln Leu Ala Gly Leu Leu Lys Gln Val Asp Ala Gly
1               5                   10                  15

Gly Asp Gln Ile Ile Ala Gly Val Asn Met Tyr Asp Asp Ile Tyr Cys
            20                  25                  30

Leu Asn Met
        35

<210> SEQ ID NO 61
<211> LENGTH: 34
<212> TYPE: PRT
<213> ORGANISM: Cyprinus carpio

<400> SEQUENCE: 61

Thr Pro Trp Val Gln Ile Asn Gly Lys Leu Lys Tyr Tyr Ser Cys Gly
1               5                   10                  15

Pro Tyr Ser Cys Trp Gly Val Asn Ser Asn Asp Gln Ile Phe Ile Met
            20                  25                  30

Lys Asp

<210> SEQ ID NO 62
<211> LENGTH: 35
<212> TYPE: PRT
<213> ORGANISM: Cyprinus carpio

<400> SEQUENCE: 62

Gly Ser Phe Ile Asn Ile Pro Gly Leu Leu Ser Met Ile Glu Val Ala
1               5                   10                  15

Thr Asp Gly Ser Val Phe Gly Val Asn Ser Gln Gly Asn Leu Tyr Gln
            20                  25                  30

Arg Thr Gly
        35

<210> SEQ ID NO 63
<211> LENGTH: 29
<212> TYPE: DNA
<213> ORGANISM: Danio rerio

<400> SEQUENCE: 63
aacgtatact gtagatctac atagacatc                                           29

<210> SEQ ID NO 64
<211> LENGTH: 35
<212> TYPE: PRT
<213> ORGANISM: Danio rerio

<400> SEQUENCE: 64

Met Arg Ala Thr Ala Ala Val Leu Leu Val Leu Cys Leu Leu Thr Ile
1               5                   10                  15

Ser His Ala Trp Asp Cys Gln Glu Val Val Asn Ile Lys Asn Leu Met
            20                  25                  30

Gln Ile Asp
        35

<210> SEQ ID NO 65
<211> LENGTH: 105
<212> TYPE: DNA
<213> ORGANISM: Danio rerio

```
<400> SEQUENCE: 65
atgagagcca ctgcagccgt cctattggtc ctctgtctcc tgaccatcag tcatgcatgg      60
gactgtcagg aggtagtaaa catcaagaat ctgatgcaga tcgat                    105

<210> SEQ ID NO 66
<211> LENGTH: 12
<212> TYPE: DNA
<213> ORGANISM: Danio rerio

<400> SEQUENCE: 66
tgcaaaaata aa                                                         12

<210> SEQ ID NO 67
<211> LENGTH: 12
<212> TYPE: DNA
<213> ORGANISM: Salmo salar

<400> SEQUENCE: 67
tgcaaaaata aa                                                         12
```

LEUKOLECTINS AND USES THEREOF

The present invention relates to a polypeptide, namely a lectin, its encoding nucleic acid sequence and antibodies to the polypeptide and their use in various medical applications.

The cellular immune defense system is central to surviving microbial and parasitic challenges. This system is also most relevant for managing deviant cells in carcinogenesis, after viral infections and in autoimmune diseases.

Intercellular recognition is central to such functions, but the origin of such phenomena is in itself poorly understood. After eons of diversification of the primordial sexual biota, genes must have evolved to ensure species-specific recognition of sexual cells ("fertilization"). If not, viability of sexual species would have been threatened. Several cell recognition molecules evolved. When the Cambrian era saw biota invade terrestrial biotopes, such arid biotopes increasingly favoured a restriction of sexual fertilization to sheltered environs with less chance of species confusion. Hence, genes for species-specific gamete recognition would tend to become redundant, and thus be freed to acquire novel functionality in evolution.

One obvious new function could be an ability of organisms to distinguish its own (self) cells from foreign (non-self) cells. It is proposed that this mechanism provides one rationale for the origin of the cellular immunity system, a phenomenon which is otherwise poorly explained. Such distinction by innate immunity (Medzhitov & Janeway, 1997, Cell, 91(3), p 295-298) is essential for multicellular organisms in order to prevent their cannibalization by parasites and microbes. Malfunction of systems to distinguish "self" from "non-self", may form the basis of some autoimmune diseases.

Misdirected immune responses which are referred to as autoimmunity can be demonstrated by the presence of autoantibodies or T lymphocytes reactive with host antigens. Whilst it is usually harmless and probably a universal phenomenon of vertebrate life, autoimmunity can be the cause of a broad spectrum of human illnesses, known as autoimmune diseases. This concept of autoimmunity as the cause of human illness is relatively new, and it was not accepted into the mainstream of medical thinking until the 1950s and 1960s. Autoimmune diseases are defined as diseases in which the progression from benign autoimmunity to pathogenic autoimmunity occurs. This progression is determined by both genetic influences and environmental triggers.

Autoimmune diseases are a major threat to health. There are more than eighty illnesses caused by autoimmunity. They are a special threat to women; about 75% of the patients are women. Autoimmune diseases are among the ten leading causes of death among women in all age groups up to 65.

Autoimmune diseases affect many different parts of the body including the skin (e.g. alopecia areata, bullous pemphigoid, epidermolysis bullosa acquisita, pemphigus foliaceous, pemphigus vulgaris, vitiligo, psoriasis and acne), kidney (e.g. IgA nephropathy), blood (e.g. aplastic anemia, autoimmune hemolytic anemias, idiopathic thrombocytopenic purpura and, pernicious anemia), joints (e.g. ankylosing spondilitis), muscles (e.g. polymyositis/dermatomyositis), ear (e.g. autoimmune hearing loss and Meniere's syndrome), eye (e.g. Mooren's ulcer, Reiter's syndrome and Vogt-Koyanagi-Harada disease), heart (e.g. autoimmune myocarditis, Churg-Strauss syndrome, giant cells arteritis, Kawasaki's disease, polyarteritis nodosa, Takayasu's arteritis and Wegener's granulomatosis), endocrine system (e.g. Addison's disease, autoimmune hypoparathyroidism, autoimmune hypophysitis, autoimmune oophoritis, autoimmune orchitis, Graves' disease, Hashimoto's thyroiditis, polyglandular autoimmune syndrome type 1 (PAS-1), polyglandular autoimmune syndrome type 2 (PAS-2), polyglandular autoimmune syndrome type 3 (PAS 3) and type 1 diabetes mellitus), gasteroenteric system (e.g. autoimmune hepatitis, celiac disease, inflammatory bowel disease and primary biliary cirrhosis), nervous system (e.g. chronic inflammatory demyelinating polyneuropathy, Guillan-Barre syndrome, multiple sclerosis and myasthenia gravis) or may affect the body systemically (e.g. antiphospholipid syndrome, autoimmune lymphoproliferative, autoimmune polyendocrinopathy, Bechet's disease, Goodpasture's syndrome, rheumatoid arthritis, sarcoidosis, scleroderma, Sjogren's syndrome and systemic lupus erythematosus).

Autoimmune diseases can strike any part of the body, and thus symptoms vary widely and diagnosis and treatment are often difficult. Some autoimmune diseases can be life threatening unless properly diagnosed and treated. Chronic autoimmune disorders like rheumatoid arthritis cripple the patient and also create heavy burdens on patients' families Some types of uveitis may cause blindness. Diseases such as scleroderma require skillful, lifelong treatment. Still other autoimmune diseases, including Graves' disease and chronic thyroiditis, can be successfully treated if correctly diagnosed, but they are frequently missed because of their subtle onset.

Inflammation is a normal process in which the body's white blood cells and chemicals protect the body from infection and foreign substances such as bacteria and viruses. In some diseases, however, the body's immune system inappropriately triggers an inflammatory response when there are no foreign substances to fight off. Inflammation is thus common in autoimmune diseases, but not all inflammatory disorders are autoimmune responses. Inflammatory diseases may also be caused by a wide variety of agents which directly attack the body such as microorganisms (viruses and fungii), bacterial toxins, certain pharmaceutical agents (antibiotics and anti-inflammatory steroids), and chemical agents (bile salts, toxic household chemicals). Diseases which are associated with inflammation include arthritis (which is a general term that describes inflammation in joints), inflammation of the heart (myocarditis), inflammation of the small tubes that transport air to the lungs (which may cause an asthma attack), inflammation of the kidneys (nephritis) and inflammation of the large intestine (colitis).

Gastrointestinal inflammatory disorders are of particular interest (e.g. gastric inflammatory diseases (such as gastric ulcer, duodenal ulcer and gastritis), and intestinal inflammatory diseases (including Crohn's disease, inflammatory bowel disease, tropical and non-tropical sprue, infectious enteritis, colitis, ulcerative colitis, pseudomembranous colitis, diverticulitis, and allergenic and radiological inflammatory diseases).

Gastrointestinal inflammatory diseases are characterized by inflammation, specifically by the presence of edema, characteristic inflammatory cells (i.e., leucocytes, histiocytes, and macrophages), and, in some cases, necrosis and ulceration of the surface epithelium. These inflammatory diseases are known to be caused by a wide variety of agents present in the gastrointestinal tract which are known to attack the surfaces thereof, producing the inflammatory disease response. Such agents include microorganisms (viruses and fungii), bacterial toxins, certain pharmaceutical agents (antibiotics and anti-inflammatory steroids), and chemical agents (bile salts, toxic household chemicals). Indeed, gastric acid itself is capable of attacking the stomach lining and producing the inflammatory state.

Currently used medications for treating inflammation include Non-steroidal anti-inflammatory drugs (NSAIDs—such as aspirin, ibuprofen or naproxen), corticosteroids (such as prednisone), anti-malarial medications (such as hydroxychloroquine) and other medications such as methotrexate, sulfasalazine, leflunomide, anti-TNF medications, cyclophosphamide and mycophenolate. Some gastrointestinal diseases, specifically gastric diseases, may be treated by inhibition of gastric acid secretion which causes the inflammation, such as by neutralizing the effects of the acid (e.g., antacid administration), or by administration of a pharmacological agent effective to inhibit gastric acid secretion.

Damaged skin is vulnerable to infection and may be unsightly and/or cause pain or discomfort. Some types of wounds are resistant to healing under normal physiological conditions, e.g. chronic ulcers. Any pharmaceutical solutions to repair damaged skin, particularly to repair wounds are very desirable.

There remains a need for treatments suitable for treating autoimmune and inflammatory disorders and conditions or skin damage with minimal side effects.

After many years of exploring processes potentially involved in evolution of the eukaryote the inventors identified a new protein (herein referred to as leukolectin), not only in gametes and in the zygote, but also in the early embryo (in specialised cells denoted lectocytes), and during ontogeny of blood cells, and finally, in leukocytes.

Initially the protein was identified in and purified from fish (see the Examples). The protein has 255 amino acids. This is the propeptide form of the lectin, which contains a 19 amino acid N-terminal peptide which suggests that it is targeted to the lysosome for later secretion (i.e. into the perivitelline space).

The amino acid sequence of the lectin allowed the development of epitope-specific antibodies, which in turn enabled the identification of many (2-8) seeming isoforms of the protein (FIG. 5), depending on the tissue analyzed. At least two mRNAs have been isolated from salmon (see Example 11), which contain minor sequence differences that result in only 7 changes at the polypeptide level (FIG. 17). Truncated forms of the protein have also been identified from salmon leukocytes (see SEQ ID NO: 2) and zebrafish, in which a secreted form (as described above, denoted sLL) and a truncated form which is missing the first 32 amino acids from the N-terminus, denoted tLL (see Example 9) have been identified.

The protein bears little resemblance to any known proteins, showing overall similarity of less than 50% to any known protein. Some similarity was observed in small domains to tachylolectins.

Related proteins have been identified in various animals, including zebrafish, cod, rainbow trout, *Oikopleura dioica* and also chicken and humans. Their cDNAs were identified (see the Examples) and were found to be extremely well conserved. The encoded proteins in the species that have been examined show less than 4% variance. This points to an essential function for these proteins.

No genes with a similar sequence have been reported in any organisms to date. Using probes to individual exons or introns, it has been established that there is only rare similarity of one exon to parts of two other reported proteins, both of which are totally unlike the molecular entity described herein.

Importantly, this novel gene is specifically expressed in human leukocytes, despite the fact that this gene cannot be found in published sequences of the human genome. Only very short segments of this gene may be detected but spread over multiple human chromosomes (see the Examples). The resolution of this conundrum is as yet not at hand.

Finally, it has been discovered that the molecular entity is secreted by cells, which is consistent with the pro-peptide form of the protein. Both the native and the recombinant form of the gene product have been isolated.

These proteins have surprisingly been found to have pronounced effects on autoimmune and inflammatory disorders, particularly of the skin, and other skin conditions. Whilst not wishing to be bound by theory it is believed that leukolectin binds to specific receptors which set in motion the normal and inherent healing processes of the human body. From the observed effects we propose that leukolectin participates in the normal process of cellular immunity. Leukolectin seem to be missing in many disease states, so that its pharmaceutical introduction triggers other defensive responses of the immune system to perform normally in the face of various challenges: the presence of foreign cells (microbes, parasites) and of altered cells of the "self" which may tie leukolectin to the etiology of auto-immune diseases, i.e., such conditions may be caused by the absence of sufficient leukolectin.

Human leukocytes contain and express extremely conserved leukolectin proteins. Until now, these proteins were unknown proteins in blood cells. Leukolectin appear to be a new member of the tachylolectin family of proteins.

In a first aspect the present invention provides a polypeptide comprising an amino acid sequence as set forth in any one of Sequences Nos. 1-8 or a sequence which is at least 50% identical to said sequence, or a portion of any of said sequences.

"Polypeptides" as referred to herein are molecules with preferably more than 50, 100, 150, 200 or 250 residues and/or less than 500, 400, 300, 200 or 100 residues or a range selected therefrom. As referred to herein a "portion" preferably comprises at least 30, 40, 50, 60, 70, 80, 90, 100, 150, 200 or more amino acids of the sequence from which it is derived. Said portion may be obtained from a central or N-terminal or C-terminal portions of the sequence. Preferably said portion is obtained from the N-terminal end, e.g. from the first 50, 100 or 150 residues of the polypeptide. Preferred aspects include truncations of said polypeptides, e.g. to remove a signal peptide or portion absent in naturally occurring variants. Preferred truncations occur at the N-terminal end and are from 1 to 50, e.g. 1 to 10, 20, 30 or 40, or 5 to 40, e.g. 10 to 35 residues in length.

Preferably said sequence is at least 55, 60, 65, 70, 75, 80, 85, 90, 95, 96, 97, 98 or 99% identical to the sequence to which it is compared.

Sequence identity may be determined by, e.g. using the SWISS-PROT protein sequence databank using FASTA pepcmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 200, 100 or 50 contiguous amino acids.

Preferably such sequence identity related polypeptides are functionally equivalent to the polypeptides which are set forth in the recited Sequence Nos. Such functionally equivalent polypeptides may take the form of derivatives as set forth below. Similarly, the polypeptides with sequences as set forth in the Sequence Nos. may be modified without affecting the sequence of the polypeptide as described below.

Furthermore, "portions" as described herein may be functional equivalents. Preferably these portions satisfy the identity (relative to a comparable region) conditions mentioned herein.

As referred to herein, to achieve "functional equivalence" the polypeptide may show some reduced efficacy in performing the medical function relative to the parent molecule (i.e. the molecule from which it was derived, e.g. by amino acid substitution), but preferably is as efficient or is more efficient. Thus, functional equivalence relates to a polypeptide which is effective to treat a disease as referred to herein, i.e. to reduce one or more symptoms of the patient, e.g. inflammation or the appearance of the skin as described hereinafter. This may be tested by comparison of the effects of the derivative polypeptide relative to the polypeptide from which it is derived in a qualitative or quantitative manner, e.g. by performing the in vivo analyses referred to in the Examples. Where quantitative results are possible, the derivative is at least 30, 50, 70 or 90% as effective as the parent polypeptide. Alternatively, in vitro testing may be performed, e.g. by analysis of binding to dendritic cells or effects on in vitro cell cultures.

Functionally-equivalent proteins which are related to or derived from the naturally-occurring protein, may be obtained by modifying the native amino acid sequence by single or multiple amino acid substitution, addition and/or deletion (providing they satisfy the above-mentioned sequence identity requirements), but without destroying the molecule's function. Preferably the native sequence has less than 20 substitutions, additions or deletions, e.g. less than 10, 5, 4, 3, 2, or 1 such modifications. Such proteins are encoded by "functionally-equivalent nucleic acid molecules" which are generated by appropriate substitution, addition and/or deletion of one or more bases.

Preferred functional equivalents are "addition" variants in which amino and/or carboxy terminal fusion proteins or polypeptides are generated, comprising an additional protein or polypeptide fused to the parent polypeptide.

Particularly preferred functionally-equivalent variants are natural biological variations (e.g. allelic variants or geographical variations within a species or alternatively in different genera, e.g. plants, animals or bacteria) and derivatives prepared using known techniques. For example, nucleic acid molecules encoding functionally-equivalent proteins may be produced by chemical synthesis or in recombinant form using the known techniques of site-directed mutagenesis including deletion, random mutagenesis, or enzymatic cleavage and/or ligation of nucleic acids.

The present invention also provides nucleotide sequences encoding said polypeptides.

In a preferred aspect, the present invention thus provides a nucleic acid molecule comprising a nucleotide sequence as set forth in any one of Sequence Nos. 9-15, a sequence which is at least 50% identical to said sequence, or a sequence which hybridizes to said sequence under non-stringent binding conditions of 6×SSC/50% formamide at room temperature and washing under conditions of high stringency, e.g. 2×SSC, 65° C., where SSC=0.15 M NaCl, 0.015M sodium citrate, pH 7.2, or a sequence complementary to any of the aforesaid sequences, or a portion thereof. Preferably said nucleic acid molecule encodes a polypeptide as set forth hereinbefore.

"Nucleic acid molecules" as referred to herein are molecules with preferably more than 150, 300, 450, 600 or 750 bases and/or less than 1500, 1200, 900, 600 or 300 bases or a range selected therefrom. "Portions" as referred to above, preferably comprise at least 90, 120, 150, 180, 210, 240, 270, 300, 450 or 600 nucleotide bases of the sequence from which it is derived. Preferably said portions encode N-terminal, central or C-terminal peptides as described hereinbefore. As discussed above in relation to polypeptides, in a preferred aspect truncations resulting in removal of residues from the N-terminal end of the recited polypeptides is contemplated. In the encoding nucleotide sequences, relative to the sequences presented herein, said truncation is preferably from 1 to 150, e.g. 1 to 30, 60, 90 or 120, or 13 to 120, e.g. 28 to 105 bases in length.

Preferably said sequence is at least 55, 60, 65, 70, 75, 80, 85, 90, 95, 96, 97, 98 or 99% identical to the sequence to which it is compared.

Sequence identity may be determined by, e.g. FASTA Search using GCG packages, with default values and a variable pamfactor, and gap creation penalty set at 12.0 and gap extension penalty set at 4.0 with a window of 6 nucleotides.

Preferably such sequence identity related or hybridizing nucleic acid molecules are functionally equivalent to the nucleic acid molecules which are set forth in the recited Sequence Nos. Such functionally equivalent nucleic acid molecules may take the form of derivatives as set forth below and are considered functionally equivalent if they encode polypeptides which would be considered functional equivalents according to the tests described hereinbefore. Preferred functional equivalents are those which encode the preferred polypeptides as set out above, e.g. nucleic acid molecules which encode polypeptides found in different genera or species than the specific molecules mentioned herein.

Furthermore, "portions" as described herein may be functional equivalents. Preferably these portions satisfy the identity (relative to a comparable region) or hybridizing conditions mentioned herein.

Nucleic acid molecules according to the invention may be single or double stranded DNA, cDNA or RNA, preferably DNA and include degenerate, substantially identical and hybridizing sequences as described above. Ideally however the molecules are DNA or cDNA.

The polypeptides as described above, include those which are modified without affecting the sequence of the polypeptide, e.g. by chemical modification, including by deglycosylation or glycosylation. Such polypeptides may be prepared by post-synthesis/isolation modification of the polypeptide without affecting functionality, e.g. certain glycosylation, methylation etc. of particular residues.

The polypeptides of the invention may also take the form of peptidomimetics which may be considered derivatives in which the functional features of the polypeptide are retained but are presented in the context of a different, e.g. non-peptide structure. Such peptidomimetics have successfully been developed and used for other particularly medical applications.

Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudopeptides and cyclic peptides. Structural elements considered redundant for the function of the peptide may be minimized to retain a scaffold function only or removed where appropriate.

When peptidomimetics retain one or more peptide elements, i.e. more than one amino acid, such amino acids may be replaced with a non-standard or structural analogue thereof. Amino acids retained in the sequences may also be derivatised or modified (e.g. labelled, glycosylated or methylated) as long as the functional properties of the polypeptides of the invention are retained. The peptidomimetics are referred to as being "derivable from" a certain polypeptide sequence. By this it is meant that the peptidomimetic is designed with reference to a defined polypeptide sequence, such that it retains the structural features of the peptide which are essential for its function. This may be the particular side chains of the polypeptide, or hydrogen bonding potential of the structure. Such features may be provided by non-peptide components or one or more of the amino acid residues or the bonds linking said amino acid residues of the polypeptide may be modified so as to improve certain functions of the polypeptide such as stability or protease resistance, while retaining the structural features of the polypeptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional amino acids are listed in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |

TABLE 1-continued

| Non-conventional amino acid | Code | Non-conventional amino acid | Code |
|---|---|---|---|
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Omser |
|  |  | L-O-methyl homoserine | Omhser |

Non-standard amino acids which may be used include conformationally restricted analogs, e.g. such as Tic (to replace F), Aib (to replace A) or pipecolic acid (to replace Pro).

The polypeptides and nucleic acid molecules discussed above also include derivatives which have been modified, e.g. to facilitate their use in pharmaceutical applications (discussed below), e.g. by the addition of targeting or functional groups, e.g. to improve lipophilicity, aid cellular transport, solubility and/or stability. Thus oligosaccharides, fatty acids, fatty alcohols, amino acids, peptides or polypeptides may be conjugated to the aforementioned polypeptides or nucleic acid molecules. Nucleic acid molecules may be present in a viral carrier as described hereinafter.

The polypeptides also encompass derivatives in the form of "pro-drugs" or "pro-peptides" such that the added component may be removed by cleavage once administered, e.g. by cleavage of a substituent added through esterification which may be removed by the action of esterases. Such pro-drugs include native precursors of the naturally occurring proteins which are cleaved e.g. by proteolysis to yield the polypeptide of interest. Such precursors may be inactive in the precursor form but may be activated by proteolytic cleavage. The nucleic acid molecules of the invention thus similarly encompass molecules which encode such pro-drugs or precursors. Modified polypeptides or nucleic acid molecules as described above may be tested to ensure that they retain functional activity relative to the unmodified molecule by determining if they have the same or similar medical effects.

The nucleic acid molecules described above may be operatively linked to an expression control sequence, or a recombinant DNA cloning vehicle or vector containing such a recombinant DNA molecule. This allows intracellular expression of the polypeptide of the invention as a gene product, the expression of which is directed by the gene(s) introduced into cells of interest. Gene expression is directed from a promoter active in the cells of interest and may be inserted in any form of linear or circular DNA vector for incorporation in the genome or for independent replication or transient transfection/expression. Suitable transformation or transfection techniques are well described in the literature. Alternatively, the naked DNA molecule may be introduced directly into the cell for the uses described herein.

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules required for performance of the method of the invention as described hereinafter. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art. Preferred vectors include bacterial and mammalian expression vectors pGEX-KG, pEF-neo and pEF-HA. The nucleic acid molecule may conveniently be fused with DNA encoding an additional polypeptide, e.g. glutathione-S-transferase, to produce a fusion protein on expression.

Thus viewed from a further aspect, the present invention provides a vector, preferably an expression vector, comprising a nucleic acid molecule as defined above.

Other aspects of the invention include methods for preparing recombinant nucleic acid molecules according to the invention, comprising inserting nucleotide sequences encoding the polypeptides of the invention into vector nucleic acid.

In methods as described hereinafter, the polypeptides may be administered to a cell by transfection of a cell with a nucleic acid molecule of the invention. As mentioned above, the present invention thus extends to nucleic acid molecules comprising a sequence which encodes the polypeptides of the invention as described herein and their use in methods described herein. Preferably said nucleic acid molecules are contained in a vector, e.g. an expression vector.

Nucleic acid molecules of the invention, preferably contained in a vector, may be introduced into a cell by any appropriate means. Suitable transformation or transfection techniques are well described in the literature. A variety of techniques are known and may be used to introduce such vectors into prokaryotic or eukaryotic cells for expression. Preferred host cells for this purpose include insect cell lines, eukaryotic cell lines or *E. coli*, such as strain BL21/DE3. The invention also extends to transformed or transfected prokaryotic or eukaryotic host cells containing a nucleic acid molecule, particularly a vector as defined above.

A further aspect of the invention provides a method of preparing a polypeptide of the invention as hereinbefore defined, which comprises culturing a host cell containing a nucleic acid molecule as defined above, under conditions whereby said polypeptide is expressed and recovering said molecule thus produced. The expressed polypeptide forms a further aspect of the invention.

The invention also extends to a polypeptide encoded by a nucleic acid molecule as hereinbefore described. This may be produced by expression of a host cell as described above.

Cells containing polypeptides of the invention, but which have been modified relative to native cells by direct introduction of said polypeptides or by expression of encoding nucleic acid material form further aspects of the invention. Preferably said polypeptides or nucleic acids molecules do not appear in said cells endogenously, i.e. said cell is modified to contain exogenous polypeptides or nucleic acid material.

The present invention also extends to antibodies (monoclonal or polyclonal) and their antigen-binding fragments (e.g. $F(ab)_2$, Fab and Fv fragments, i.e. fragments of the "variable" region of the antibody, which comprises the antigen binding site) directed specifically to the polypeptides as defined hereinbefore.

Such antibodies may be used in the methods described hereinafter, in particular the therapeutic methods which are described.

The antibodies described herein may be used in vitro to identify the presence or amount of the polypeptide of the invention and may be used diagnostically to identify disorders or skin damage as described herein associated with aberrant levels of said polypeptide, i.e. variation relative to normal levels, e.g. elevated or reduced levels of said polypeptide.

Thus, in a further aspect the present invention provides a method of determining the presence or amount of a polypeptide of the invention or a portion thereof in a sample, wherein an antibody as herein described is brought into contact with said sample and the extent of antibody binding is indicative of the present or amount of said polypeptide or portion thereof.

The sample which is assessed may be any convenient sample, e.g. blood or a tissue sample or non-biological sample. Preferably the sample is derived from an animal as described herein, preferably a human.

The present invention further provides a method of diagnosing a disorder or skin damage as described herein in an animal, comprising at least the steps of determining the presence or amount of a polypeptide as described herein in a sample from said animal, wherein said presence or amount is diagnostic of said disorder or skin damage. The polypeptide may be detected by, for example, using the antibodies described hereinbefore. The sample and animal is preferably as described herein. The amount is preferably a reduction in the level of said polypeptide compared to normal levels. Diagnosis may be achieved by comparison to standard tables of normal subjects compared to those with the disorder or skin damage under investigation.

The polypeptides or nucleic acid molecules used in compositions and uses of the invention as described hereinbelow may be obtained or derived from naturally occurring sources or may be generated entirely or partially synthetically.

Conveniently the polypeptides and nucleic acid molecules are isolated in accordance with the protocols described in the Examples. Such methods and the products of such methods form further aspects of the invention.

Thus in a further aspect the present invention provides a method of isolating a polypeptide as described herein from hatching fluid (e.g. of salmon) comprising at least the steps of:

a) suspending eggs in a minimal volume of water (e.g. equivalent to the volume of the eggs or less);

b) inducing synchronized, rapid hatching of said eggs (preferably such that hatching is complete within less than 2 hours for more than 95% of the embryos);

c) filtering the hatched eggs to obtain hatching fluid;

d) optionally adding solid urea to said hatching fluid to allow dissociation of eggshell fragments and subjecting said fluid to low speed centrifugation;

e) performing a first exclusion chromatography step, e.g. using a Superdex 16/60 column or a Biotex 100 ultra filter;

f) optionally performing a second exclusion chromatography step, e.g. using a Superdex 16/60 column, and g) optionally removing contaminating proteins, such as zonase by affinity chromatography, e.g. on a Benzamidine-Sepharose column.

The invention further extends to polypeptides prepared by the above described method.

When the polypeptide of the invention is obtained from leukocytes it is obtained in unmodified form. Polypeptides obtained from salmon hatching fluid are modified (by glycosylation and/or phosphorylation), but both forms are equally effective in the methods described herein.

The polypeptides or nucleic acid molecules described herein are preferably substantially free of any contaminating components derived from the source material or materials used in the isolation procedure or in their synthetic preparation. Especially preferably the compound is purified to a degree of purity of more than 50 or 60%, e.g. >70, 80 or 90%, preferably more than 95 or 99% purity as assessed w/w (dry weight). Such purity levels correspond to the specific molecule of interest, but includes its degradation products. Where appropriate, enriched preparations may be used which have lower purity, e.g. contain more than 1, 2, 5 or 10% of the molecule of interest, e.g. more than 20 or 30%. The polypeptides of the invention may be purified by, for example, chromatography (e.g. HPLC, size-exclusion, ion-exchange, affinity, hydrophobic interaction, reverse-phase) or capillary electrophoresis.

Polypeptides of the invention may be generated synthetically, e.g. by ligation of smaller synthetically generated peptides or more conveniently by recombinant expression of a nucleic acid molecule encoding said polypeptide as described hereinbefore.

Nucleic acid molecules of the invention may be generated synthetically, e.g. by amplification of a nucleic acid sequence as described herein such as from an appropriate cDNA library.

The polypeptides, nucleic acid molecules or antibodies as described herein may be used in vitro, for example in cell or organ culture, to affect immune functions in cells.

Alternatively the polypeptides, nucleic acid molecules or antibodies may be used ex vivo, on animal parts or products, for example organs or collected blood, cells or tissues, particularly when it is contemplated that these will be reintroduced into the body from which they are derived.

However, the polypeptides, nucleic acid molecules and antibodies are preferred for use in vivo as discussed in more detail below.

Polypeptides, nucleic acid molecules and antibodies as described herein have applications for the treatment of various disorders or conditions as described hereinafter. The present invention thus extends to a pharmaceutical composition comprising a polypeptide, nucleic acid molecule or antibody as described hereinbefore and one or more pharmaceutically acceptable excipients and/or diluents.

By "pharmaceutically acceptable" or "physiologically acceptable" is meant that the ingredient must be compatible with other ingredients in the composition as well as physiologically acceptable to the recipient.

The active ingredient for administration may be appropriately modified for use in a pharmaceutical composition. For example the compounds used in accordance with the invention may be stabilized against degradation by the use of derivatives as described above.

The active ingredient may also be stabilized in the compositions for example by the use of appropriate additives such as salts or non-electrolytes, acetate, SDS, EDTA, citrate or acetate buffers, mannitol, glycine, HSA or polysorbate.

The nucleic acid molecule, polypeptide or antibody of the invention may be present in said compositions as the sole active ingredient or may be combined with other ingredients, particularly other active ingredients, e.g. to augment the therapeutic effect or to make the composition more appealing to the consumer.

The composition comprising the polypeptide of the invention may also comprise zonase or a related enzyme. As referred to herein zonase is a preparation containing an enzyme, wherein said preparation exhibits one protein band on SDS-PAGE analysis, with a molecular weight of around 28 kDa, obtainable by a method comprising the steps of:
 a) suspending salmon eggs in a minimal volume of water;
 b) inducing synchronized, rapid hatching of said salmon eggs;
 c) filtering the hatched salmon eggs to obtain hatching fluid;
 d) adding solid urea to said hatching fluid to allow dissociation of salmon eggshell fragments and subjecting said fluid to low speed centrifugation;
 e) further purifying said zonase by subjecting the centrifugation supernatant to gel filtration; and
 f) further purifying said zonase by affinity chromatography on a Benzamidine-modified Superose 6B® column, wherein said affinity chromatography is performed by performing concentrated salt washes followed by elution with dioxane, in concentrated salt solution, to extract zonases bound to the chromatography matrix or to macromolecular structures;
wherein said zonase has the following properties:
 a) cleaves chromozym X;
 b) is inhibited by benzamidine;
 c) cleaves peptide bonds with arginine;
 d) remains active in the presence of 8M urea, molar concentrations of salt, distilled water and organic solvents, preferably dioxane or propanol; and
 e) retains enzymatic activity in solution at room temperature for 50 days.

Zonase may be prepared as described in the examples and added to the composition or may represent an "impurity" after the preparation of the polypeptide of the invention from natural sources. In compositions comprising both the polypeptide of the invention and zonase, the polypeptide may be present in the range 1-100% of their total combined weight and zonase may make up 0 to 99%. Preferably the polypeptide is present at a range of 50-100%, e.g. >80, 90, 95, 96, 97, 98 or 99% and zonase is present at 0 to 50%, e.g. <20, 10, 5, 4, 3, 2 or 1% of the combined weight.

In a further aspect of the invention, the compositions as described herein are for use in therapy.

As mentioned above, the polypeptides, nucleic acid molecules and antibodies of the invention exhibit therapeutic properties in the treatment of various autoimmune and inflammatory disorders, particularly of the skin as well as treatment of damaged skin, e.g. by sun, cold, irradiation (e.g. X-ray, such as when used to treat cancers) or as a result of a wound.

As referred to herein a "disorder" refers to an underlying pathological disturbance in a symptomatic or asymptomatic organism relative to a normal organism, which may result, for example, from infection or an acquired or congenital genetic imperfection.

As set forth in the Examples, the utility of leukolectin for treating a variety of inflammatory, autoimmune and other skin conditions has been illustrated. Similar efficacy may be expected for treating other conditions. For example, chronic gastrointestinal inflammation may be explained by an excessive reaction to (or perhaps in some instances as) failure of reaction by dendritic cells to noxious agents. The introduction of leukolectin, e.g. orally, would therefore be expected to treat the chronic GIT inflammation in much the same way that inflamed skin responds favourably to the introduction of leukolectin.

Autoimmune diseases may stem from specific somatic expression of mutated versions of normal cell-surface antigens. Without wishing to be bound by theory, leukolectins may serve to protect target cells from attack.

As referred to herein an "inflammatory disorder" is a disorder in which inflammation is observed at some point during the disorder's progression and may be the sole symptom or one of several symptoms. The inflammatory disorder may be acute or chronic and may be as described hereinbefore or hereinafter. Inflammatory disorders include cardiovascular inflammation (e.g. atherosclerosis, stroke), gastrointestinal inflammation (including ulcers such as gastric or duodenal ulcers), hepatic inflammatory disorders, pulmonary inflammation (e.g. asthma, ventilator induced lung injury), kidney inflammation, ocular inflammation (e.g., uveitis), pancreatic inflammation, genitourinary inflammation, neuroinflammatory disorders (e.g., multiple sclerosis, Alzheimer's disease), allergy (e.g., allergic rhinitis/sinusitis, skin allergies and disorders (e.g., urticaria/hives, angioedema, atopic dermatitis, contact dermatitis, psoriasis), food allergies, drug allergies, insect allergies, mastocytosis), skeletal inflammation (e.g., arthritis, osteoarthritis, rheumatoid arthritis, spondyloarthropathies), infection (e.g., bacterial or viral infections; oral inflammatory disorders (i.e. perodontis, gingivitis or somatitis); sores on mucosal membranes; and transplantation (e.g., allograft or xenograft rejection or maternal-fetal tolerance).

Preferred inflammatory disorders for treatment according to the present invention are inflammatory skin disorders such as Eczema, Acne, Rosacea, psoriasis and contact dermatitis, gastrointestinal inflammation and conditions of the mucous membranes such as ulcers or sores.

As referred to herein an "autoimmune disorder" is one in which benign autoimmunity has progressed to pathogenic autoimmunity and may be as described hereinbefore or hereinafter. Autoimmune diseases include, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatoniyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

"Damaged skin" as referred to herein includes skin which has been damaged by external influences such as heat, irradiation (by light of various wavelengths such as X-ray or UV), cold, friction, tearing or a wound, e.g. resulting from an accident or surgery. Alternatively damaged skin may result from an infection, or disease or underlying genetic abnormality. The damage may be exhibited as cracks, redness, itching, inflammation, horny skin, flakes, etc.

The invention thus provides a method of treating or preventing an autoimmune disorder, an inflammatory disorder or damaged skin in an animal, wherein a polypeptide, nucleic acid molecule, antibody or pharmaceutical composition as described hereinbefore is administered to said animal.

Alternatively stated, the present invention provides the use of a polypeptide, nucleic acid molecule, antibody or pharmaceutical composition as described herein in the preparation of a medicament for treating or preventing an autoimmune disorder, an inflammatory disorder or damaged skin in an animal.

In a further alternative statement, the invention provides a polypeptide, nucleic acid molecule, antibody or pharmaceutical composition as described herein for treating or preventing an autoimmune disorder, an inflammatory disorder or damaged skin in an animal.

In a preferred aspect the invention provides such methods, uses, polypeptides, nucleic acid molecules, antibodies or pharmaceutical compositions for treating or preventing an autoimmune disorder of the skin, an inflammatory disorder of the skin or damaged skin wherein a polypeptide, nucleic acid molecule, antibody or pharmaceutical or composition as described hereinbefore is preferably topically administered to the skin.

Preferably said disorder is eczema, acne, psoriasis, gastrointestinal inflammation (such as in Crohn's disease, ulcerous colitis and other chronic inflammation), gingivitis and inflammation of the oral cavity and oesophagus and said damaged skin is irritated or inflamed, cracked by cold, sunburned, heat or irradiation damaged or as the result of a wound.

As used herein, "treating" refers to the reduction, alleviation or elimination, preferably to normal levels, of one or more of the symptoms or effects of said skin disorder or damage e.g. presence or extent of damaged skin, e.g. relative size of the wound, inflammation, redness, itching, pain etc. relative to the symptoms or effects present on a different part of the body of said individual not subject to said treatment or in a corresponding individual not subject to said treatment.

"Preventing" refers to absolute prevention, or reduction or alleviation of the extent or timing (e.g. delaying) of the onset of that symptom or effect. This may be achieved, for example, by gene therapy methods, e.g. use of anti-RNA or non-sense sequences.

The method of treatment or prevention according to the invention may advantageously be combined with administration of one or more active ingredients which are effective in treating or preventing the disorders or skin damage. Thus, pharmaceutical compositions of the invention may additionally contain one or more of such active ingredients.

According to a yet further aspect of the invention we provide products containing one or more polypeptides, nucleic acid molecules or antibodies as herein defined and one or more additional active ingredients as a combined preparation for simultaneous, separate or sequential use in human or animal therapy.

The compositions of the invention may be formulated in conventional manner with one or more physiologically acceptable carriers, excipients and/or diluents, according to techniques well known in the art using readily available ingredients.

Thus, the active ingredient may be incorporated, optionally together with other active substances as a combined preparation, with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents or for nasal delivery, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like.

The compositions of the invention may be formulated so as to provide quick, sustained or delayed release of the active ingredient after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

These particles may carry appropriate surface molecules to improve circulation time (e.g. serum components, surfactants, polyoxamine908, PEG etc.) or moieties for site-specific targeting, such as ligands to particular cell borne receptors. Appropriate techniques for drug delivery and for targeting are well known in the art and are described in WO99/62315.

The use of solutions, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

Compositions may be for topical (e.g. to the skin), oral or parenteral administration, e.g. by injection. As mentioned hereinbefore, leukolectin shows very little variation between different species. Indeed, it has been found to be invariant in a healthy human population and this would hence allow the use of leukolectin, e.g. by administration by injection into subjects, without triggering a humoral antibody response, in a similar manner to the protein insulin which is also invariant in the human population. Therefore, systemic therapy by injection of leukolectin may be used to treat the conditions described herein, particularly auto-immune disorders.

Topical compositions and administration are however preferred, and include gels, creams, ointments, sprays, lotions, salves, sticks, soaps, powders, films, aerosols, drops, foams, solutions, emulsions, suspensions, dispersions e.g. non-ionic vesicle dispersions, milks and any other conventional pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

The concentration of active ingredient in compositions of the invention, depends upon the nature of the compound used (i.e. the polypeptide, nucleic acid molecule or antibody), the mode of administration, the course of treatment, the age and weight of the patient, the medical indication, the body or body area to be treated and may be varied or adjusted according to choice. Generally however, concentration ranges for the compound described herein is 0.0001, 0.0005, 0.001 or 0.01 to 25%, e.g. 0.0005-15%, e.g. 0.01 to 10%, such as 0.1 to 5, e.g. 1-5% (w/w of the final preparation for administration, particularly for topical administration). Said concentrations are determined by reference to the amount of the compound itself and thus appropriate allowances should be made to take into account the purity of the composition. Effective single doses may lie in the range of from 0.1-100 mg/day, preferably 2-10 mg/day, depending on the animal being treated, taken as a single dose.

The administration may be by any suitable method known in the medicinal arts, including for example oral, parenteral (e.g. intramuscular, subcutaneous, intraperitoneal or intravenous) percutaneous, buccal, rectal or topical administration or administration by inhalation. The preferred administration forms will be administered orally, or most preferably topically. As will be appreciated oral administration has its limitations if the active ingredient is digestible.

To overcome such problems, ingredients may be stabilized as mentioned previously.

It will be appreciated that since the active ingredient for performance of the invention takes a variety of forms, e.g. nucleic acid molecule (which may be in a vector) or polypeptide, the form of the composition and route of delivery will vary. Preferably however liquid solutions, creams or suspensions would be employed, particularly e.g. for oral delivery or topical administration.

Either the polypeptide or nucleic acid molecules of the invention may be used for the above mentioned medical indications. In the later gene therapy methods, the nucleic acid molecules are preferably provided in vectors which are suitable for transfection/transformation as described above, e.g. viral vectors such as adenovirus using gene therapy methods known in the art for medical applications.

Animals to which the compositions may be applied or administered include mammals, reptiles, birds, insects and fish (e.g. salmon or cod). Preferably the animals to which the compositions of the invention are applied are mammals, particularly primates, domestic animals, livestock and laboratory animals. Thus preferred animals include mice, rats, rabbits, guinea pigs, cats, dogs, monkeys, pigs, cows, goats, sheep and horses. Especially preferably the compositions are applied, or administered, to humans.

The following Examples are given by way of illustration only in which the Figures referred to are as follows:

FIG. 1 shows (A) gel filtration of partially purified salmon zonase to yield leukolectin. A Superdex 16/60 column (GE Healthcare) was connected to an FPLC system and used with a buffer flow of 1 ml/min for 120 ml. The elution of proteins from the column was monitored by UV 280 nm (right y-axis) and collected in 1 ml fractions. Zonase activity was measured by cleavage of Chromozym X at OD406. Native molecular weight of zonase spans a wide range with a peak of around 50 kDa. Lectin MW=30 kDa, and (B) Identification of salmon (leuko-) lectin by immunoblotting. Protein immunoblot analyses of selected fractions obtained from the above gel filtration using an epitope-based anti-(leuko-) lectin (see FIG. 3) antibody. The fraction-numbers are shown above the immunoblots.

Molecular weight markers (kDa) are indicated on the left. The estimated molecular weight of the lectin corresponds to the one obtained by other methods (see FIG. 3).

FIG. 2 shows the identification of lectin-producing cells (lectocytes) in Atlantic salmon embryos in which panels A, B & C represent transverse sections through the body of embryos of Atlantic salmon that had been formalin-fixed and paraffin-embedded. The presence of leukolectin was determined by means of a rabbit polyclonal anti-LL antibody using immunoperoxidase staining method (A) or indirect immunofluorescence (B and C). Cells reacting to antilectin-antibody can be seen as dark (A), or light (B and C) relative to the background, respectively. Numerous immunoreactive single cells with specific cytological features are seen in the epidermis with no spatial restrictions along the anterior-posterior embryonic axis. Arrows in A&B point to relatively large cells (lectocytes), easily distinguishable from surrounding epidermal cells. Their nuclei are basal, while cytoplasm is filled with leukolectin so that the cells protrude like mushrooms in the periviteline space. Panel 2C shows their granular contents.

FIG. 3 shows alignment of Leukolectins, in order from top to bottom, from Human (SEQ ID NO:5), Salmon (SEQ ID NOs:1 and 2), Chicken (SEQ ID NO:4), Cod (SEQ ID NO:3) and two translations (SEQ ID NOs: 39 and 40) from the two contigs that make up the UniGene Family Ssa.23163, a salmon EST collection. Of the two contigs, contig 1 is the one that resembles the primary structure of the leukolectins the most. However, the difference between the two contigs is not large, only about 80%.

FIG. 4 shows (A) SMART domains of sequences similar to human Leukolectin. The highest scoring sequences from a BLASTP search using WU-BLAST 2 are presented. The sequences are listed from the more to the less similar ones. a—human leukolectin (SEQ ID NO:5), b—salmon embryonic leukolectin (SEQ ID NO:1), c—salmon leukocytic leukolectin (fragment) (SEQ ID NO:2), d—chicken leukolectin (fragment) (SEQ ID NO:4), e—cod leukolectin (fragment) (SEQ ID NO:5), f—common carp fish-egg lectin (Ac#-P68512) (SEQ ID NO:41), g—tungara frog ranaspumin-6 (Ac#:B5DCK6) (SEQ ID NO:42), h—zebrafish Zgc: 173443 protein (Ac#: A8E4Z1) (SEQ ID NO:43). Note that sequences from salmon leukocytic, chicken leukocytic and cod leukocytic Leukolectins are only partial, and not full length sequences. The full length version of these sequences will probably resemble the overall structure found in leukolectin from human leukocytes (a) and salmon embryos (b). Further, the Leukolectin pattern, with 5 consecutive TECPR-domains, still holds for the Tungara frog sequence, but not for the Zebrafish sequence where only 4 TECPR domains are found, and (B) a graphic representation of leukolectin with 5 TECPR-domains. TECPR domains are most likely composed of 4 beta-strands generating 2 beta-sheets. There are THREE disulfide bonds: one is internal in TECPR #4, the other two are in connecting loops, as indicated. In general the sugar-recognition sites are found in such lectins in the areas between TECPR-domains. The lectin most closely related to Leukolectin has a known sugar specificity for primarily N-Acetylglucosamine. The putative sugar recognition specificity for Leukolectin remains to be established.

FIG. 5 shows the presence of perivitelline Lectin in Leukocytes. An IPG-strip spanning the pH-range of 4-7 was used in the first dimension, while a 12.5% polyacrylamide gel was utilized during the second dimension electrophoresis.

A: In salmon leukocytes, only two spots were found to react positively to the anti-Lectin polyclonal antibody. Their molecular weight was around 26 kDa, with a pI around 6.5. Leukolectin can also be identified in leukocyte-preparations in other species.

B: In a preparation from salmon, we found a number of immunoreactive spots (numbered 1-8), with a molecular weight around 30 kDa, which spanned a pH-range of pI from 4.9 to 6.5.

FIG. 6 shows co-expression of leukolectin in the myeloid lineage, specifically in the monocyte-macrophage lineage in zebrafish. (A) Lectin and L-plastin gene expression profile. Zebrafish was found to express the same lectin as we found in salmon. A fluorescein-labelled lectin mRNA probe was used together with a DIG-labelled probe for L-Plastin mRNA probe, which is a specific marker of the monocyte-macrophage lineage. Double-labelled in situ hybridisation reveals co-expression of lectin and L-plastin mRNA in the same cells during zebrafish embryogenesis. Age of embryos in hours post-fertilisation (pf) in the lower-left corners. Lighter signals indicate the expression of L-plastin gene; darker signals indicate Lectin-expression.

Panel A (lateral view) shows co-expression of Lectin and L-plastin mRNA in the same cells, which form a dispersed axial and paraxial population on the anterior and lateral yolk. Higher magnification (A2) reveals typical leukocyte morphology of these cells. Data in A1 demonstrates expression of these two genes in bilateral bands of cells in the anterior lateral plate mesoderm (arrows). Panel B reveals the same findings at 21 h.

Panel C (24 h pf) demonstrates co-expression of the L-plastin and Lectin genes in the posterior intermediate cell mass (upper two arrows), in the ventral vein region (lower arrow), in significant number of cells dispersed along the embryonic body and head. By 24 h pf (C2) a majority of cells co-express these two genes (see arrows), but many cells appear to express only one or the other gene. Arrows in C3 indicate cells expressing only L-plastin mRNA, and (B) cellular co-localization of Lectin protein and L-plastin mRNA. Zebrafish embryos (22 h pf) were analysed by combined immuno-histochemistry with in situ hybridisation assay for lectin protein (darker signal) and L-plastin mRNA (lighter signal). In situ hybridisation used DIG-labelled cRNA specific for L-plastin gene, combined with immuno-histochemistry with rabbit antilectin polyclonal antibody.

Panel A: frontal view of the embryo. Arrows point to a cluster of cells marked by common expression of Lectin protein and L-plastin mRNA. A1: higher magnification of cluster demonstrating co-expression of L-plastin gene and lectin protein in the same cell (black arrows). Notice a few cells, small in size with rounded shape resembling mature lymphocytes next to another cell with a segmented nucleus, a typical morphological feature of mature neutrophilic leukocytes. Panels B, C, D, E illustrate dispersed cell-populations throughout the zebrafish embryo which co-express Lectin protein and L-plastin mRNA (arrow).

FIG. 7 shows the leukolectin family. Available Leukolectin proteins from Human (SEQ ID NO:5), Salmon (SEQ ID NO:1), Chicken (SEQ ID NO:4) and Cod (SEQ ID NO:3) were assembled (weblogo alignment). Total correspondence of AA residues in one position are represented by large letters, with decreasing size indicating lesser degree of correspondence. Multiple letters indicate variations.

Panel A illustrates two positive duplicate spots identified in filter nr 6, panels #5 and 2, which correspond to exact plate number 257 and 176, and well-coordinates of the clone L-7 and F-7, respectively.

Panel B demonstrates one positive duplicate spot identified in filter nr 3, panel #6, which corresponds to exact plate number 144 (based on the plate locator sheet), and well-coordinates of the clone A-12, and (B) shows the deduced genomic sequence of the leukolectin gene (2323 bp) (SEQ ID NO:10). The site of the 5 exons are indicated, and as a consequence, also the introns. The location of the Transcription start for this gene (promoter prediction, based on BDGP Neural Network Promoter Prediction, "P", predicted transcription start "ST", TATA box "T") and the sequences specifying polyAdenylation ("PA") in the gene product are indicated.

Figure 10A:
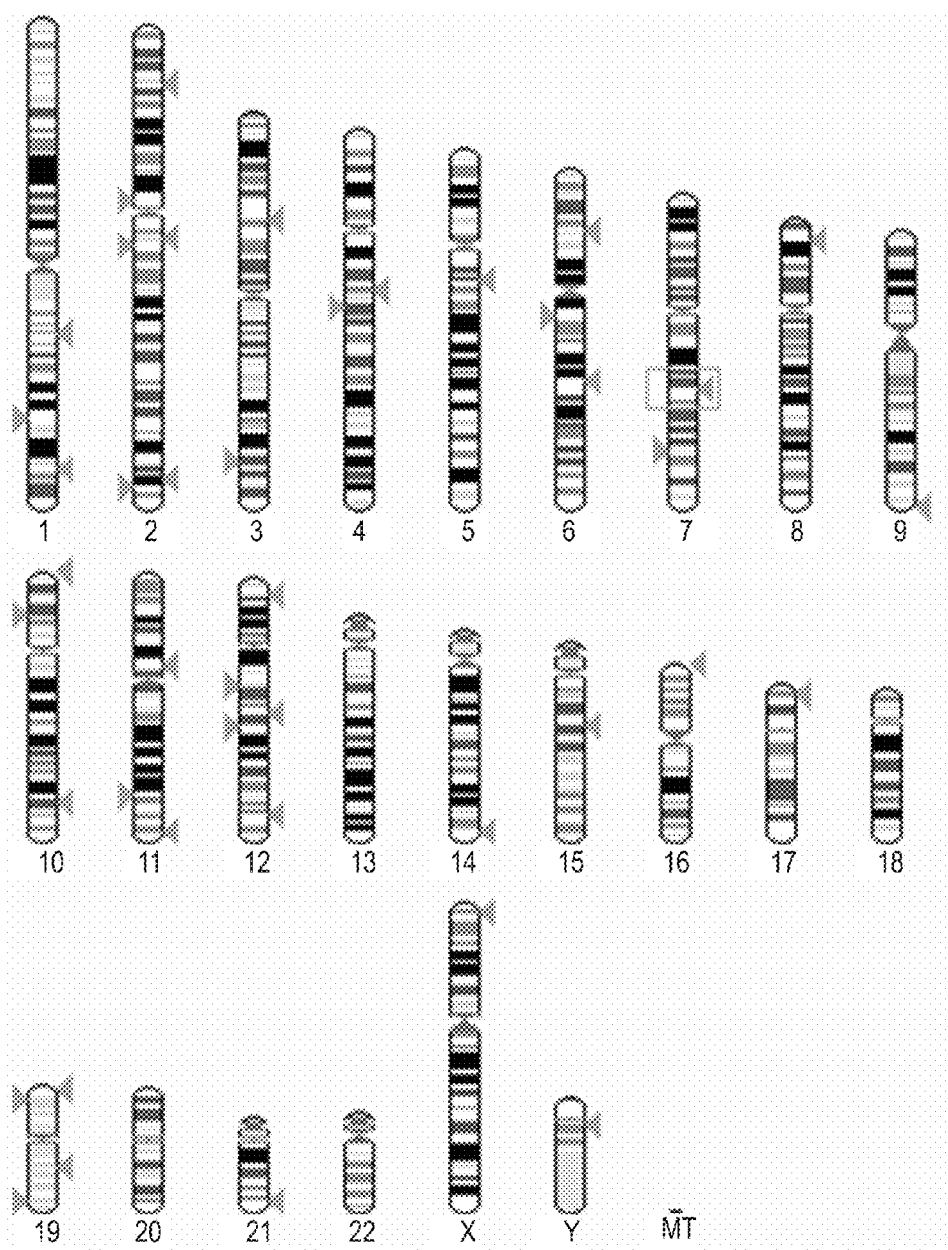
Figure 10B:
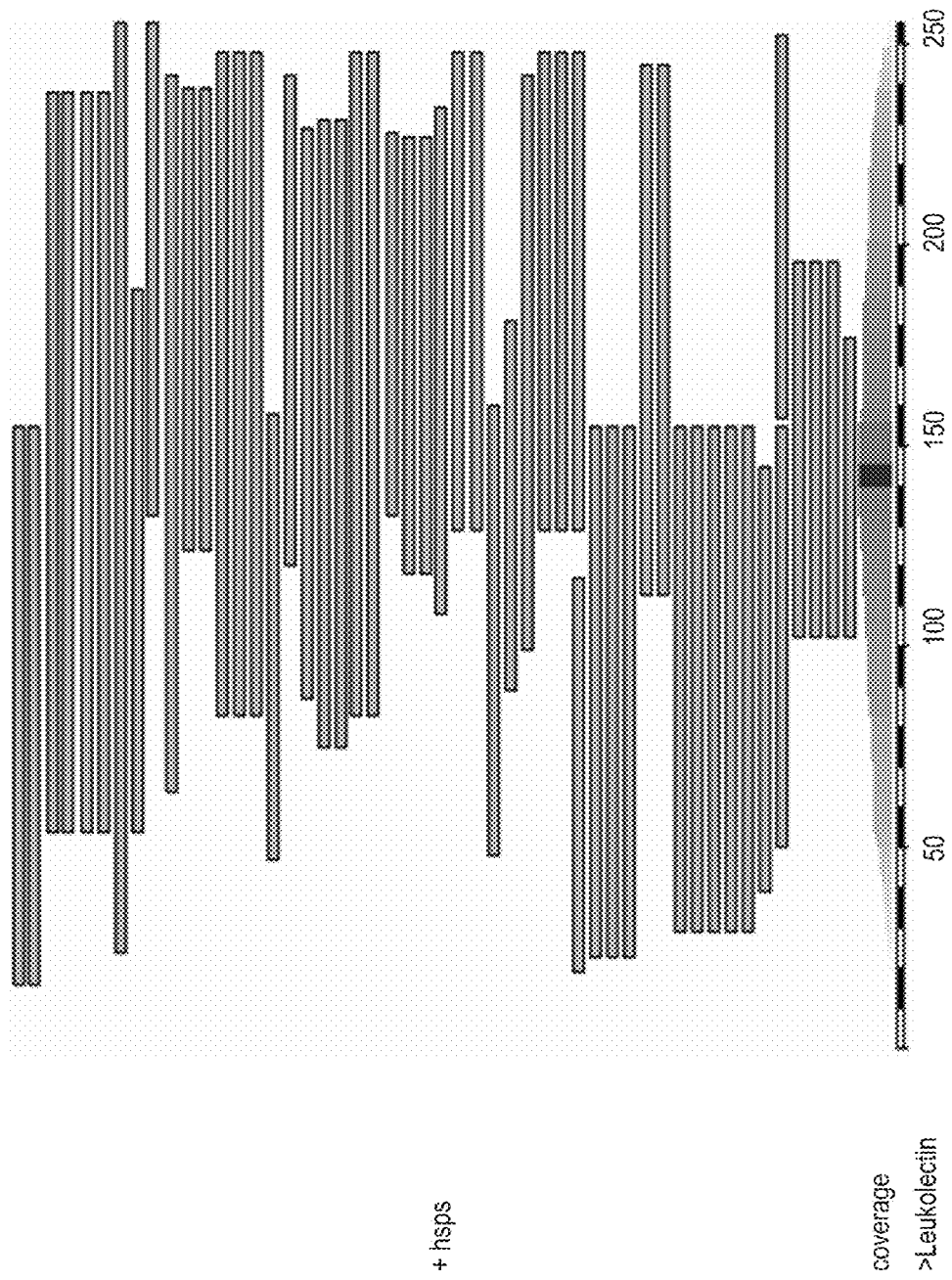

FIG. 10 shows (A) a map displaying the human chromosomes, the positions of BLASTP-hits (see table) are indicated by arrows, (B) legend coverage map:

A visualization of the position of the BLASTP hits (bars) in, and the total coverage of the query sequence (Human Leukolectin). Apparently the sum of sequences found cover the entire Leukolectin sequence, but the data clearly do not imply that this is the leukolectin gene, C) table displaying BLASTP hits and their position in the Human genome using Human Leukolectin as the query sequence.

Figure 11A:
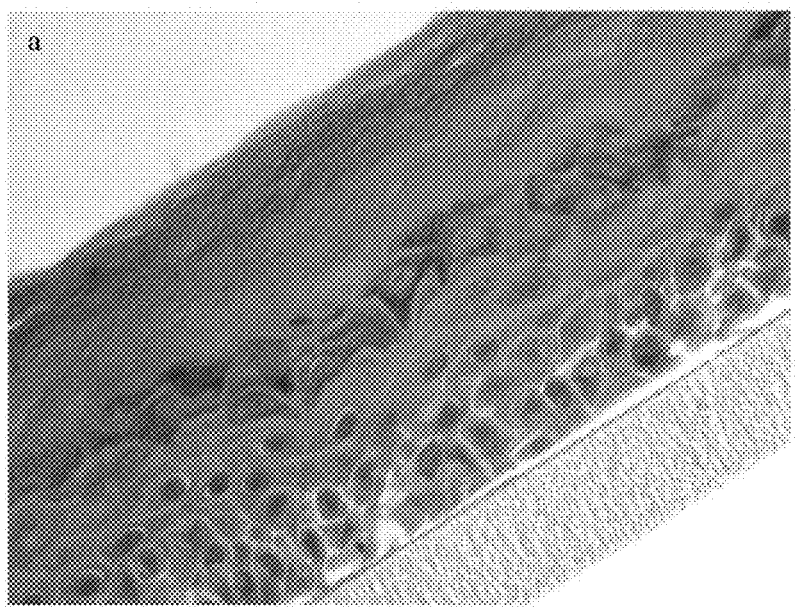
Figure 11B:
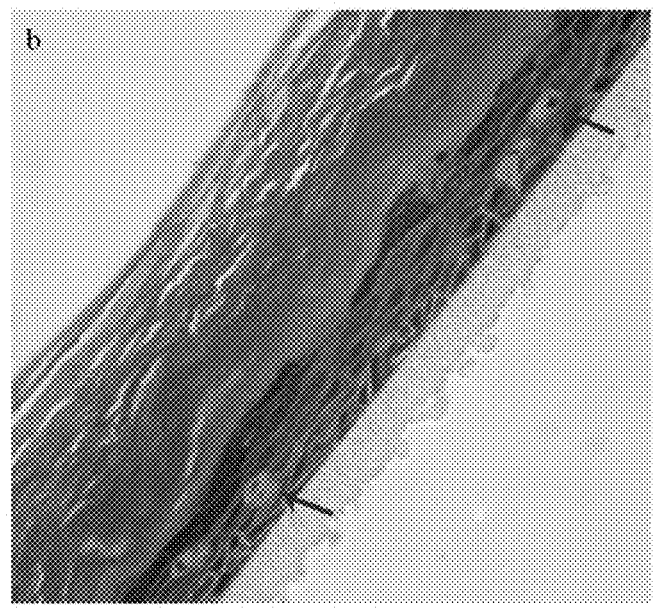

FIG. 11 shows the effects of salmon leukolectin in human epithelium. Control culture=A; Culture exposed to Leukolectin=B. Arrows point to large cells appearing in the basal layer only after exposure to leukolectin.

Figure 12A:
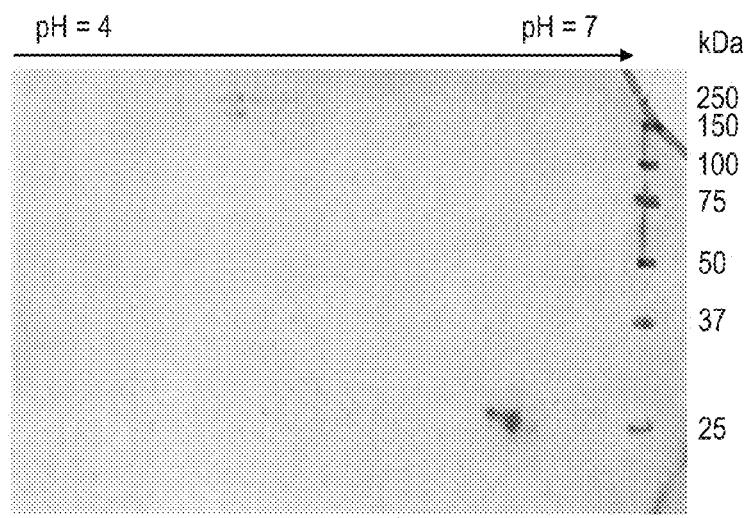
Figure 12B:
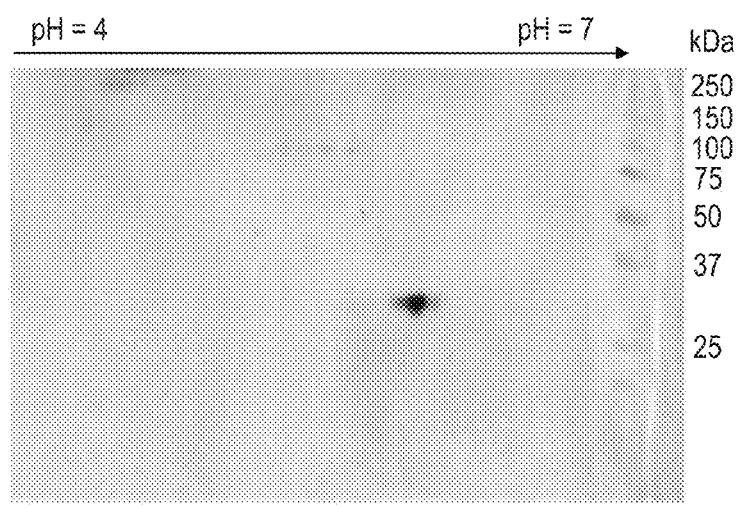

FIG. 12 shows leukolectin protein expression in leukocytes. Panel A shows 12% 2D PAGE of protein purified, ~2 μg, from salmon leukocytes. Panel B shows 15% 2D PAGE of protein purified, 0.8 μg, from human leukocytes from Lymphoprep™. Membranes were treated with polyclonal primary antibody to salmon LL, before being treated with goat anti-rabbit antibody, and visualized by ECL-enhanced detection system.

Figure 13A:
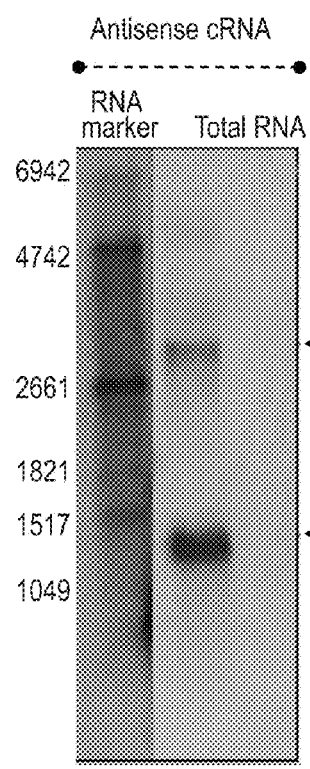

FIG. 13 shows salmon leukolectin transcripts identified in Northern blots. Panel A shows total RNA from Atlantic salmon embryos (370 dd) fractionated in 1.2% agarose in the presence of formaldehyde, and probed with antisense DIG-labelled riboprobe specific for LL (720 bp). Panel B shows Northern blot analysis of mRNA (purified by magnetic polyT-beads). Hybridisation used DIG-labelled riboprobes generated from LL partial coding sequence. Panel C shows the nitrocellulose membrane (B) was probed with sense DIG-labelled riboprobe. Grey arrows signify transcript present; the black arrow points to its absence. DIG-RNA marker I, 0.3-6.9 kb (Roche) was used.

Figure 14A:
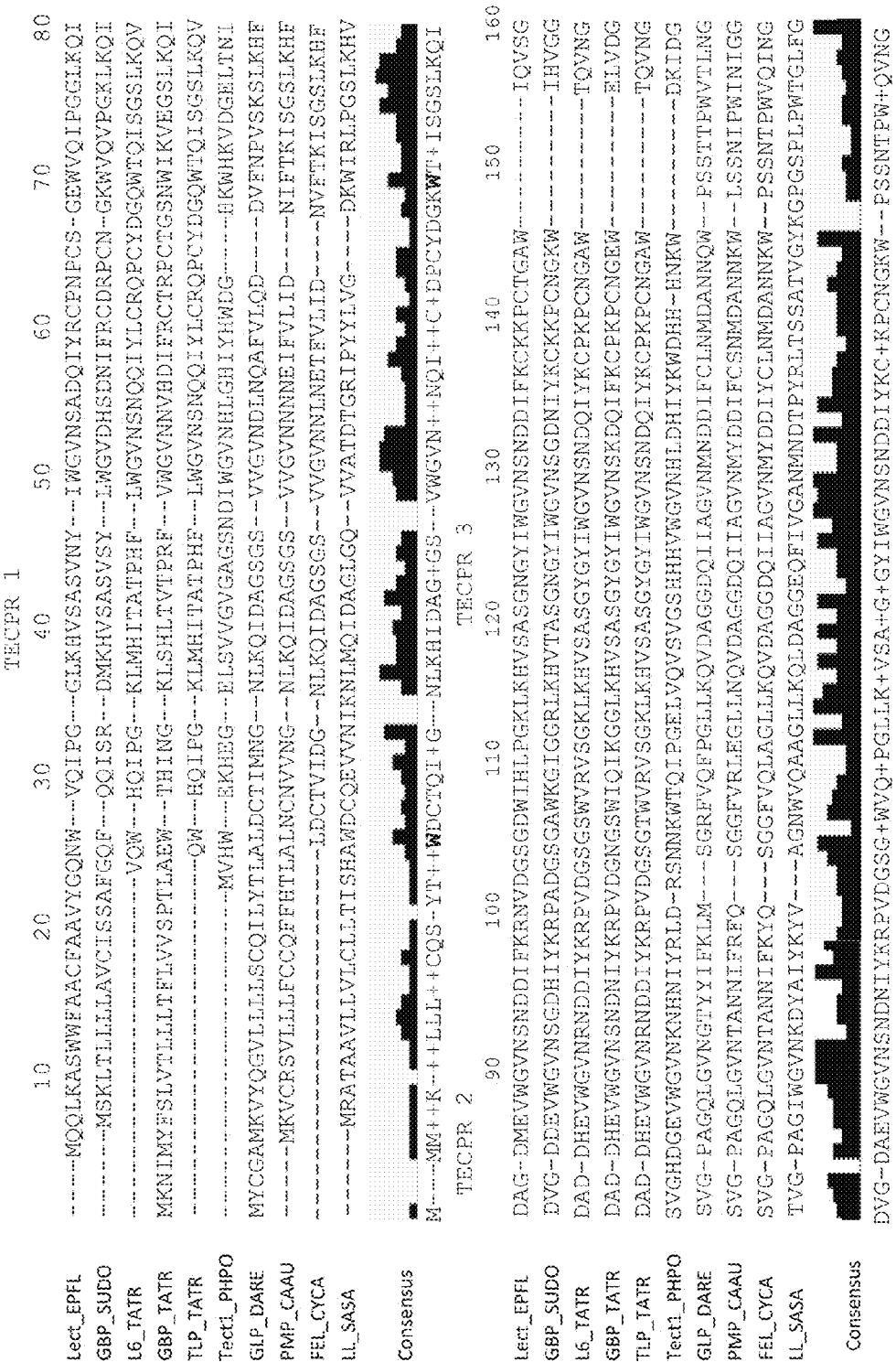

FIG. 14 show a Clustal W alignment of LL (SEQ ID NO:5) with related β-propeller proteins, in order from top to bottom, SEQ ID NOs:44-52 and 5.

FIG. 15 shows a 3-D model of LL. The left panel shows two views of a 3D-representation of a 5 bladed β-propeller 3D-model of Leukolectin based on the structure of Tachylectin 1 from *Tachypleus tridentatus* (Biesel et al., 1999, EMBO J. 18, pp 2313-2322). The model is generated using PyMol v 0.99 software. The residues of the epitope peptides are drawn in thin black lines in the protein body. Also, the positions of the 5 carbohydrate binding sites predicted by Biesel et al. (1999) are indicated as faint but solid tanned hexose structures. The right panel shows representations of the predicted propeller domains in LL (SEQ ID NO:5) (top), R1-R5 are SEQ ID NOs:53-57, respectively and in FEL (SEQ ID NO:52) (bottom), R1-R5 are SEQ ID NOs:58-62, respectively, compared to the consensus propeller domain.

FIG. 16 shows the amplification of the full length zebrafish leukolectin (LL) cDNA sequence. Panel A shows amplicons that were obtained using several primer pairs, and cloned by RT-PCR. mRNA used for reverse transcription was extracted from embryos at 24 hpf. DNA marker: 100 bp ladder (New England Biolabs). Panel B shows that 5'RACE PCR resulted in amplification of two distinct products, respectively ~500 bp and ~400 bp (generated after a second round of PCR amplification using gene specific reverse primer and GeneRacer forward nested primer). mRNAs were collected from developmental stages indicated. Panel C shows that the zebrafish LL full length cDNA sequence is 1240 nt including an open reading frame (ORF) of 765 nt. The ORF comprises five exons which are drawn to scale and shown as black boxes. 5'UTR region is presented as solid line. The 5'UTR nucleotide sequence is shown (SEQ ID NO:63). Translation start sites ATG at position +1 and potential second ATG at position +94, are highlighted in the nucleotide sequence (SEQ ID NO:65). The protein translation is shown (SEQ ID NO:64). Panel D shows the expression of the truncated LL at various developmental stages. Panel E shows that the salmon (SEQ ID NO:67) and zebrafish (SEQ ID NO:66) sequences are highly conserved even at in the 3'UTR.

Figure 17:
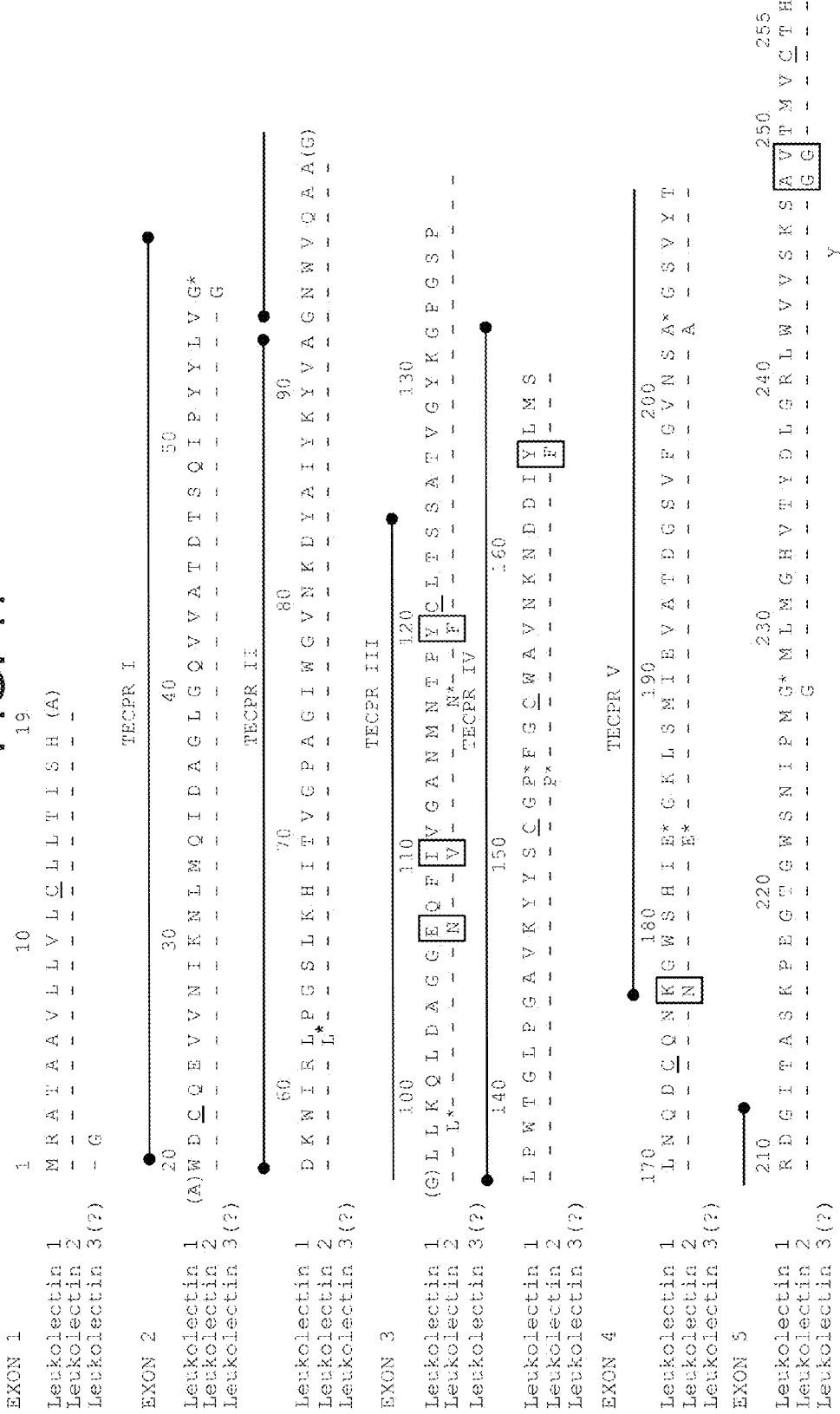

FIG. 17 provides a summary of the exons, domains and sequence variability of Leukolectins from salmon. Sequence data for different leukolectins is shown in relation to positions of variable AA residues, Cysteine-residues (C) and TECPR-domains (from the SMART database). Leukolectin sequences differ in only seven positions, marked in boxes. Five such variable residues occur within TECPR-domains, while two are found close to the C-terminal end. Variations incompatible with either leukolectin-1 (SEQ ID NO:1) or leukolectin-2 (SEQ ID NO:7) are shown under as leukolectin-3 (SEQ ID NO:8), where only two positions are defined here (#2 and #245). While the other positions are not marked, the data indicate that most of these positions are nearly identical to the other leukolectins.

As is the case with the fish egg lectin (FEL), the 3 disulfide-bridges in LL are predicted to connect, respectively, the first and the last cysteines, while the second and second last cysteines form a second bridge, and the two (middle) cysteines within exon 3 form the last disulfide bridge. These cysteines are marked in grey and underlined. The one cysteine in the propeptide not involved in disulfide bridges is in exon 1. Note lack of interconnecting loops between the first three domains, and the lack of variation in two loops which interconnect the last two TECPR-domains. Three TECPR-domains are coded for by a single exon (2 and 3), while two domains span two exons. The sharp correlation of ends of exons and domains is noteworthy. In four of five domains, a Trp residue occupies the third AA of the domain, while in the first predicted TECPR domain, W is the initial residue. Finally, asterisks mark residues where variant AAs have been found in either or both leukolectin-1 or leukolectin-2.

Figure 18:
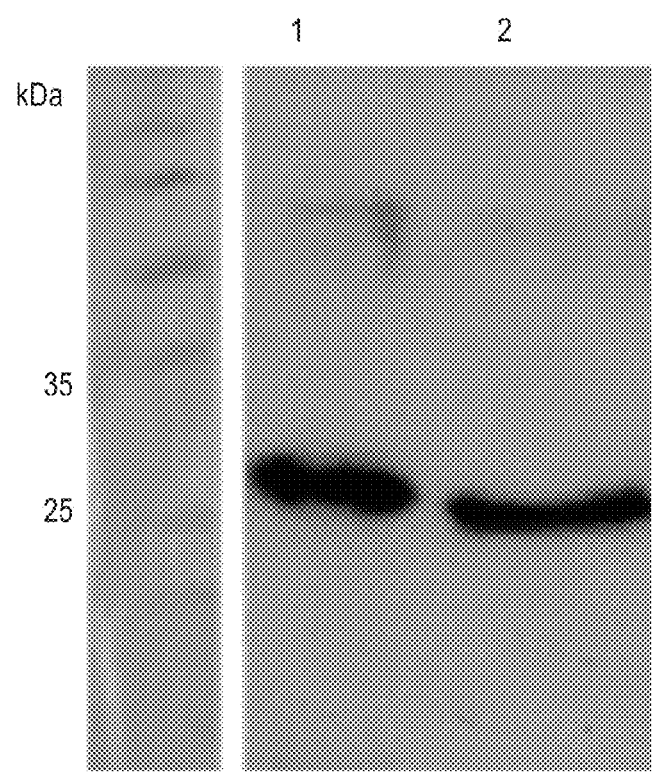

FIG. 18 shows LL protein in the hatching fluid of Rainbow trout (*Oncorhyncus mykiss*) embryos, detected in Western blots. MW standards are shown on the left (BioRad 161-0373). Hatching fluid proteins from Rainbow trout (Lane 1) and salmon leukolectin protein prepared by affinity chromatography (Lane 2) probed with antileukolectin antibody. A protein of ~26 kDa is found in both cases, corresponding to the Mw of LL.

Figure 19A:
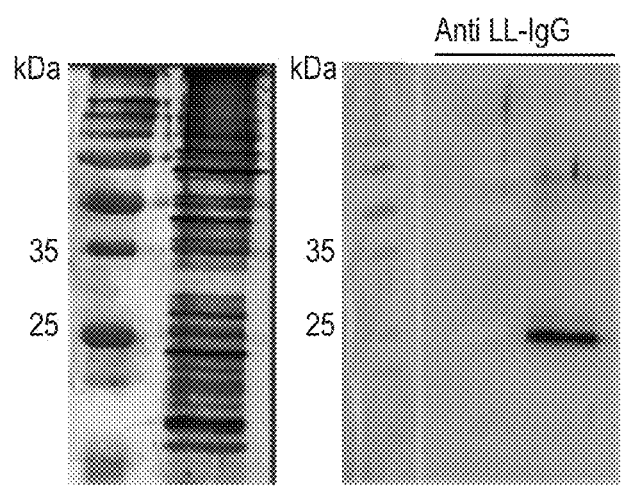
Figure 19B:
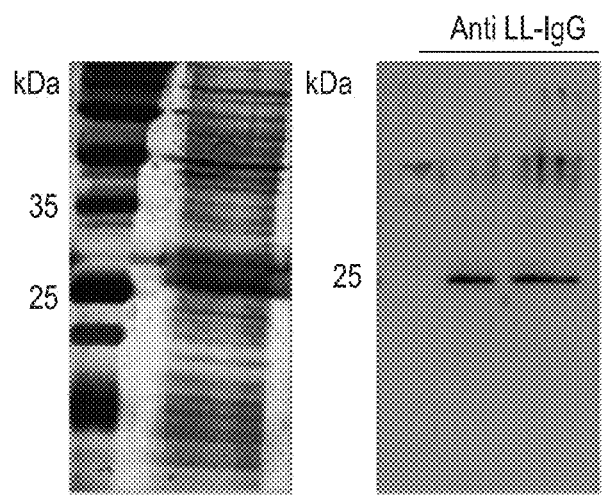

FIG. 19 A, left panel, shows Cod leukolectin among proteins found in cod hatching fluid. Cod hatching fluid was analyzed by 15% SDS PAGE, and its constituent proteins visualized by silver staining. Lane 1: Protein marker (BioRad's Dual color 161-0374). Lane 2: Hatching fluid proteins.

The right panel shows cod hatching fluid, separated by 15% SDS PAGE analysis, blotted onto a nitrocellulose membrane, and probed with appropriate dilutions of affinity-purified rabbit polyclonal anti-leukolectin IgG antibody. Lane 1: Protein marker (BioRad's Dual color 161-0374). Lane 2:

Hatching fluid aliquot. Leukolectin location was pinpointed using horseradish peroxidase (HRP) labelled goat anti-rabbit secondary antibody, enhanced by the ECL detection system. A main immuno-reactive protein of around 26 kDa was detected. B, shows the equivalent SDS PAGE and membrane for hatching fluid proteins from Oikopleura dioica.

EXAMPLE 1

Identification and Characterization of Leukolectin

Protein Isolation

During the course of analyzing hatching fluid components of salmon a new protein present in embryos was identified.

A method for preparing partially purified zonase which may be used as the starting material for isolating the polypeptide of the invention is provided in WO99/29836 which is hereby incorporated by reference (particularly Example 1 of the described method, but optionally without the urea step).

Both zonase and leukolectin were purified from salmon hatching fluid. To improve the protein concentration of hatching fluid, salmon eggs were transferred to minimal volumes of water prior to hatching. Highly synchronous hatching can be induced by elevated (room) temperatures, or by deoxygenation (Oppen-Berntsen et al. 1990, Aquaculture, 86, pp. 417-430), which yields a small volume of highly concentrated preparation of crude zonase and associated proteins.

The initial purification of zonase involved filtration of hatched salmon eggs through cheese cloth. This filtrate may be frozen for years without significant zonase degradation, before being thawed and employed for further protein purification. This fact greatly simplifies production of a starting material for purifying salmon zonase and associated proteins, including leukolectin.

The next, optional, step involved adjusting the protein filtrate to 4M urea, to dissociate fragments of the salmon eggshell, which allowed their removal along with extraneous debris by low speed centrifugation (15,000 g; 2×15 min). This material showed no sign of clogging columns, which is characteristic of crude materials prepared differently from what is described above. This crude protein preparation was suitable for purification by conventional chromatographic techniques and zonase may be purified further as described in Example 7.

Leukolectin from hatching fluid may be isolated together with zonase. From partially purified zonase preparations (as described above), leukolectin may be isolated by exclusion chromatography as zonase in its native form is substantially larger than Leukolectin. For a first separation, Superdex 16/60 columns with the conditions described in the FIG. 1 Legend suffices, whereafter zonase may be removed by affinity chromatography on Benzamidine-Sepharose columns For large scale preparations the use of ultrafiltration is also suitable as zonase in its native form does not significantly penetrate ultra filters with size exclusion of 100 kDa unlike leukolectin.

Buffers used are millimolar Tris (e.g. 10 mM) at pH around neutrality or slightly alkaline (pH 7.5-8.5), containing 5 mM NaCl.

Large scale extraction of human leukocytes from products that are out of date in blood banks are also envisioned, by use of extraction in organic solvents (e.g. 80% acetone) because leukolectin remains in solution during this procedure which precipitates most other proteins. Final purification by chromatographic and filtration methods are as above.

The isolated protein was also found to be expressed in gametes and in the zygote, and furthermore, also in the early embryo (during ontogeny of the hemopoietic system), and finally, in leukocytes.

Figures 1, 9A:
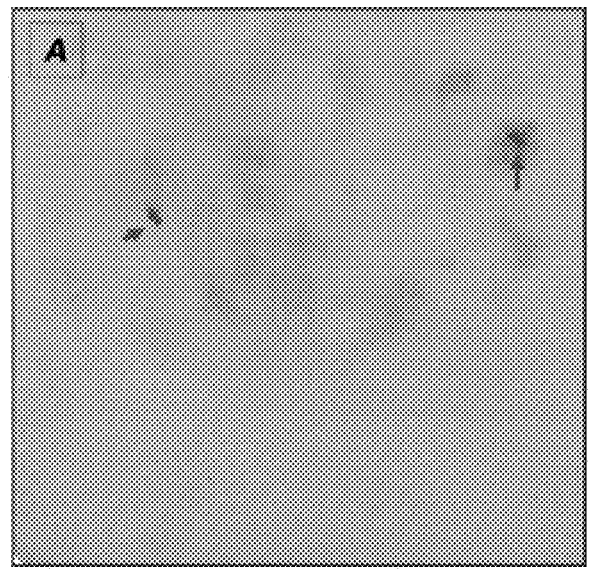
FIG. 9 shows (A) experiments to identify and establish a gene sequence for salmon Leukolectin.

The previously unidentified protein was found to co-purify with zonase. The size of this new protein, estimated by chromatography under native conditions, was just shy of 30 kDa. (FIG. 1).

Protein Expression

Figures 2, 9A:
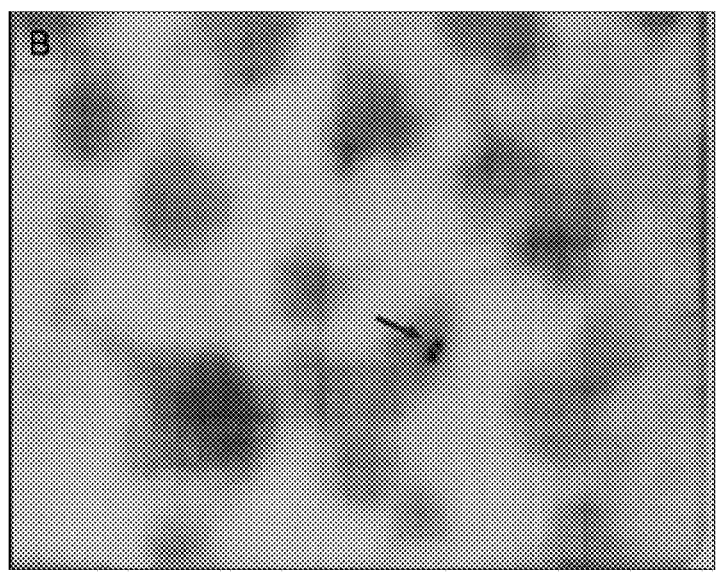

The isolated protein was used to generate a polyclonal antibody. Cells were analysed for the presence of the protein by means of a rabbit polyclonal anti-LL antibody using an immunoperoxidase staining method or indirect immunofluorescence. The results are shown in FIG. 2.

By use of the antibody, we found that the new protein originated in a cell type different from the cells that produce choriolysins (hatching enzymes). The morphology of these individual cells (termed lectocyte) is shown in the Figure and is clearly distinct from (individual) hatching gland cells expressing choriolysins.

Sequence Analysis

The new protein was subjected to standard characterization such as determination of its tryptic peptides, followed by partial direct Edman sequencing. From the puzzle of peptides, trial and error constructions of degenerate primers for detecting an mRNA in fish embryos to produce a cDNA, were at first unsuccessful until the reverse primer was set simply to match a polyA-tail. In this manner, and with the use of multiple new primer sets as they became identified, we were able to find at least two cDNAs of approximately 1200 NT. These proved to be very similar in sequence, with only a handful of variant AA residues. For both, some of the N-terminal sequence was missing.

Using N-RACE methodology we subsequently established that the above sequences belonged to a protein of 255 amino acids, with a 19 AA propeptide and with an unusual N-terminal tryptophan residue in the processed protein. This latter result would explain the great difficulties in obtaining an N-terminal sequence by direct analysis. However, this was eventually achieved to confirm the virtual N-terminal residues.

Figure 1A:
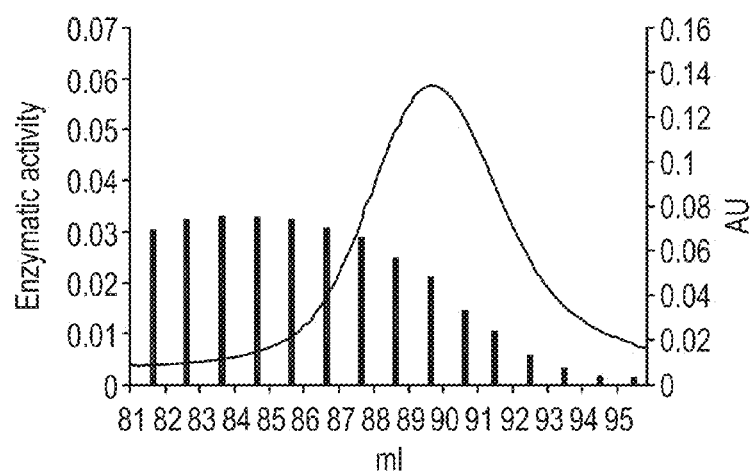
Figure 1B:
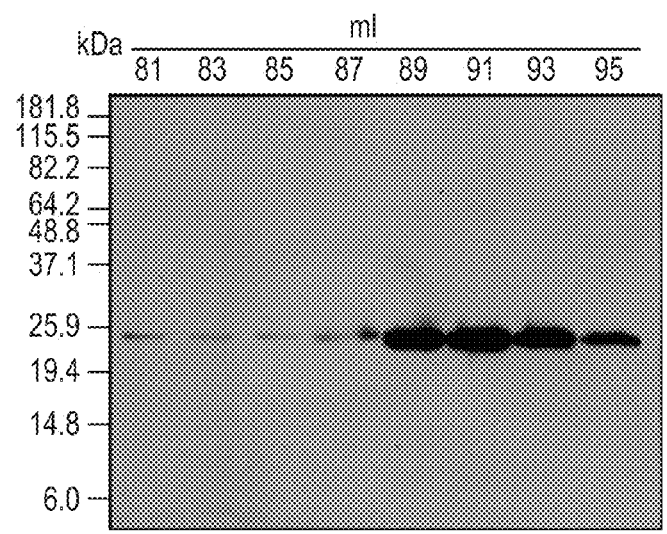
Figure 2A:
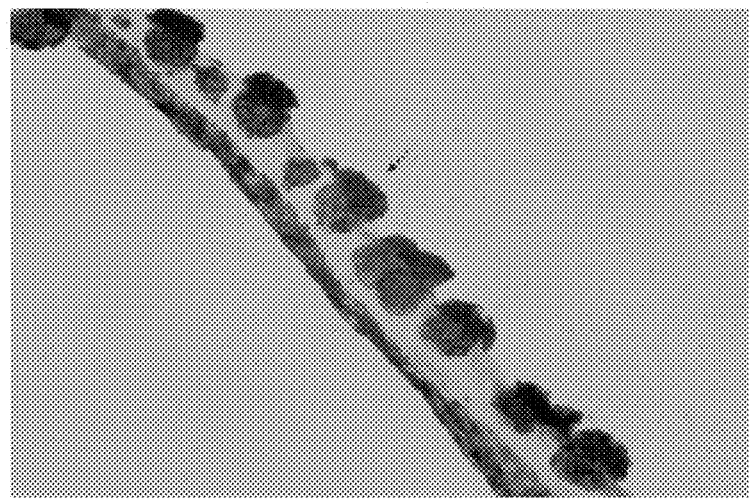
Figure 2B:
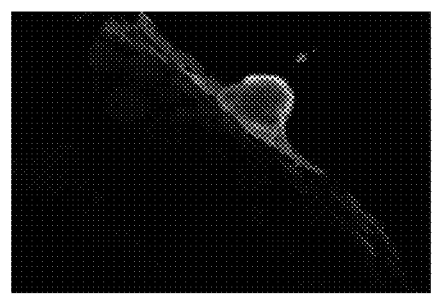
Figure 2C:
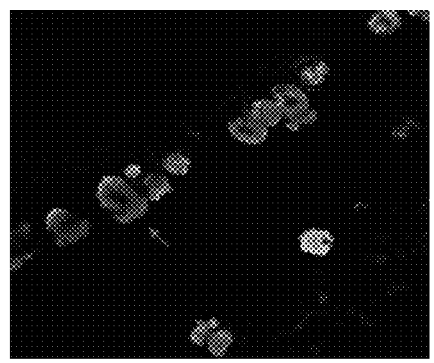
Figure 3A:
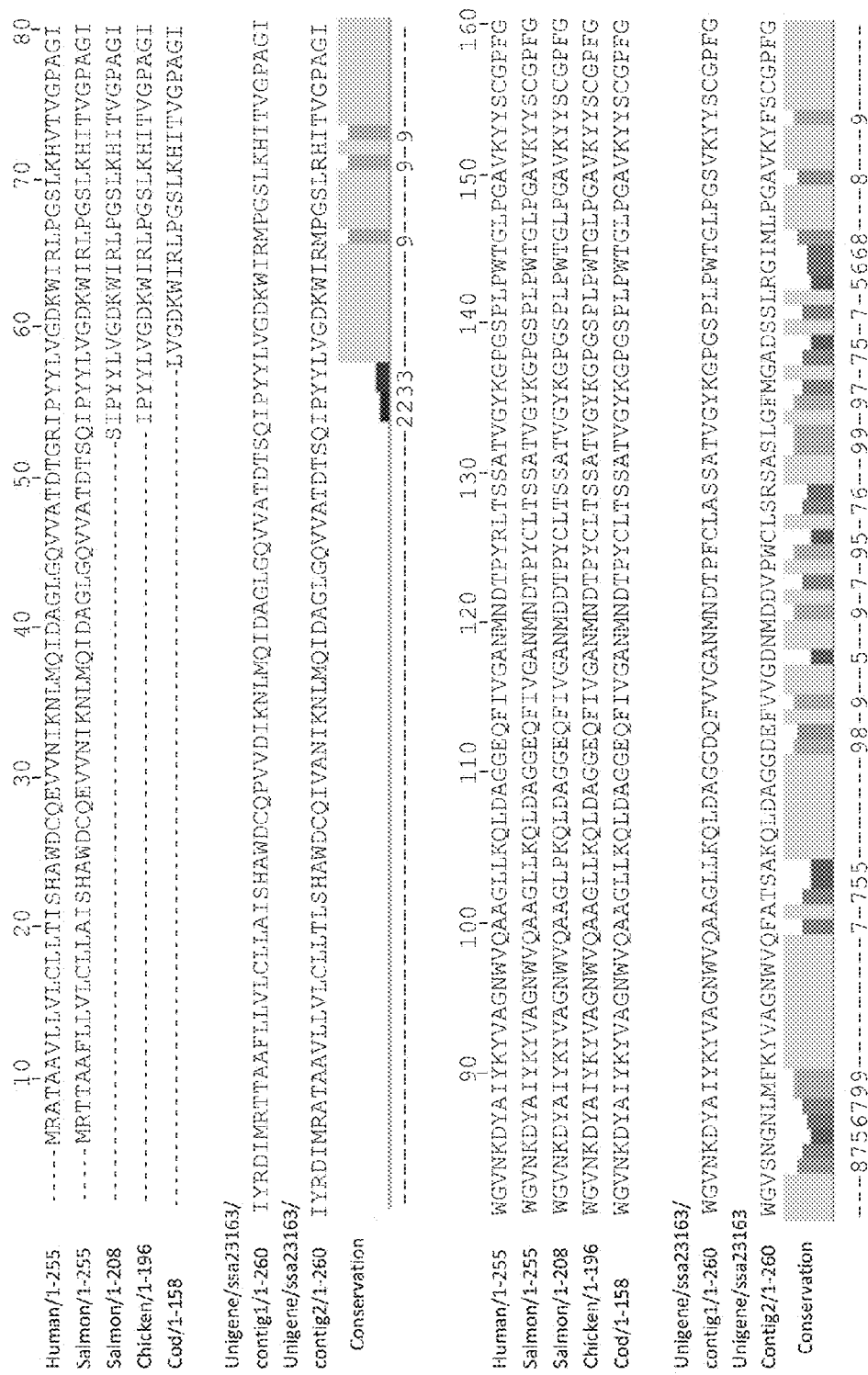

Using the N-terminal sequence of the protein to search EST data bases, we identified a protein sequence clearly representing the new protein (FIG. 3).

Searching the databases for proteins with resemblance to the new protein identified only one somewhat similar candidate (Leren, unpublished). This is a fish egg lectin isolated from carp (Galliano et al., 2003, Biochem., J., 376, p 433-440), with an overall similarity of at most 48% found by a manual alignment of sequences.

Figure 4B:
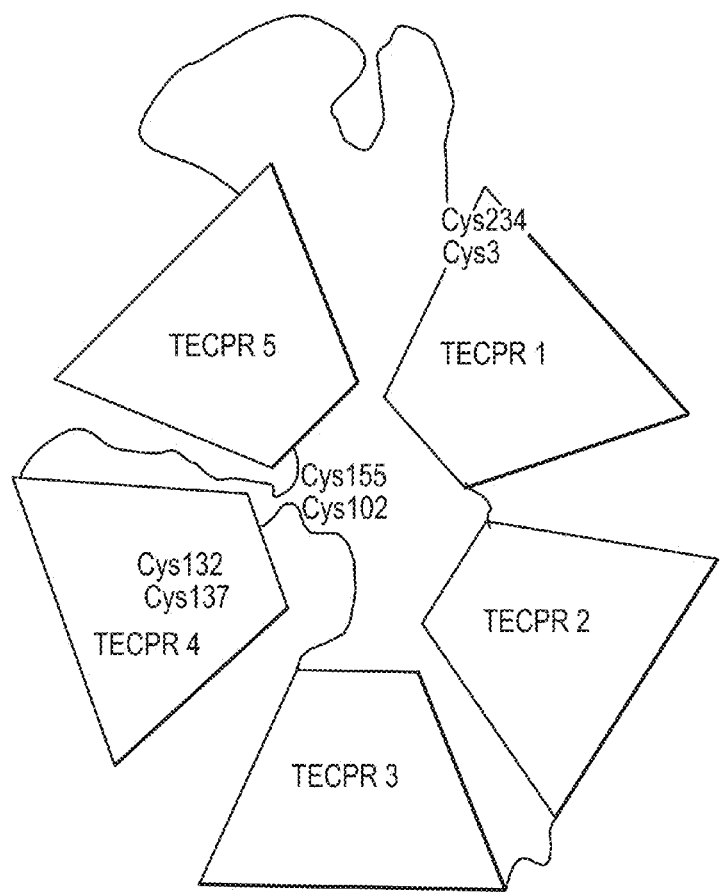

Bioinformatic analysis suggested that the new protein was a lectin related to the tectonins (Leren, unpublished). In compiling a list of all proteins with similar TECPR-domain structure, our new lectin appears to represent a new type of lectin (FIGS. 4A & B). The virtual AA-sequence of the new lectin contained five TECPR-domains which showed some similarity with tachylolectins in lower invertebrates (Shigenaga et al., 1993, J. Biochem (Tokyo), 114, p 307-316).

The propeptide form of the new lectin contains a 19 AA peptide which suggested its targeting to lysosomes and for later potential secretion (i.e. into the perivitelline space).

The virtual AA-sequence of the new lectin allowed the development of epitope-specific antibodies, which in turn allowed us to identify many (2-8) seeming isoforms of the protein (FIG. 5), depending on tissue analyzed.

One possibility is that the Lectin found in the hatching gland cells (FIG. 6B) is secreted into the perivitelline space along with the choriolysins, and that these possess posttranslational modifications which increase their apparent size and which lower their apparent pf As salmon is a tetraploid fish, and as our data indicate more than one gene for Leukolectin in salmon, the array of 8 Leukolectin moieties in partially purified zonase preparations may stem from three increasing modifications of two slightly different Leukolectin proteins, for a total of 4×2, or 8 differing leukolectins. The causes of variation need to be empirically verified.

The estimated MW of the lectin is around 25-30 kDa. Estimated pI for the corresponding salmon lectin is about pH=6.5. Observed pIs (Riste, unpublished) were from pH 6.5 to 4.9 in salmon perivitelline lectins, and from pH 6.4 to 6.6 in salmon leukocytic lectins (the lectin was identified by Western blotting techniques).

Expression During Embryonic Development

Figure 6A:
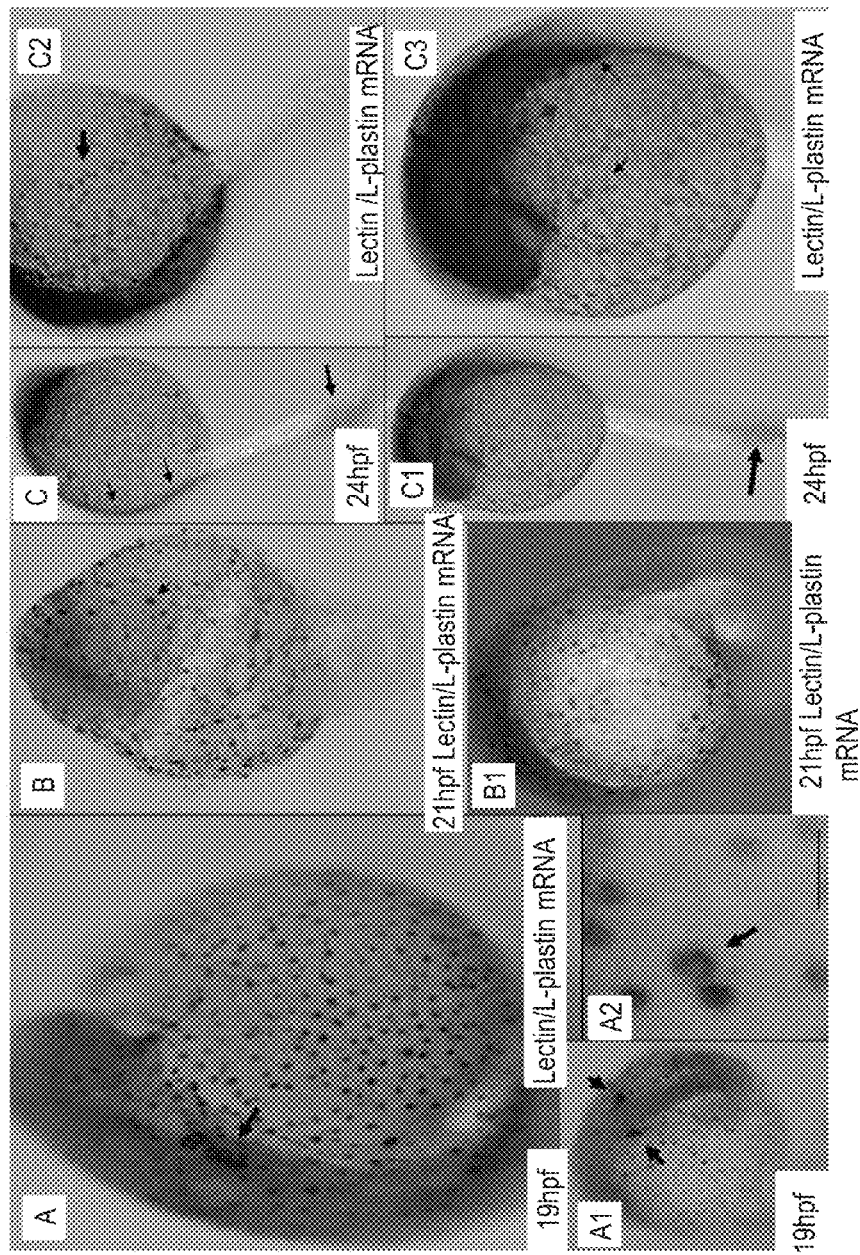
Figure 6B:
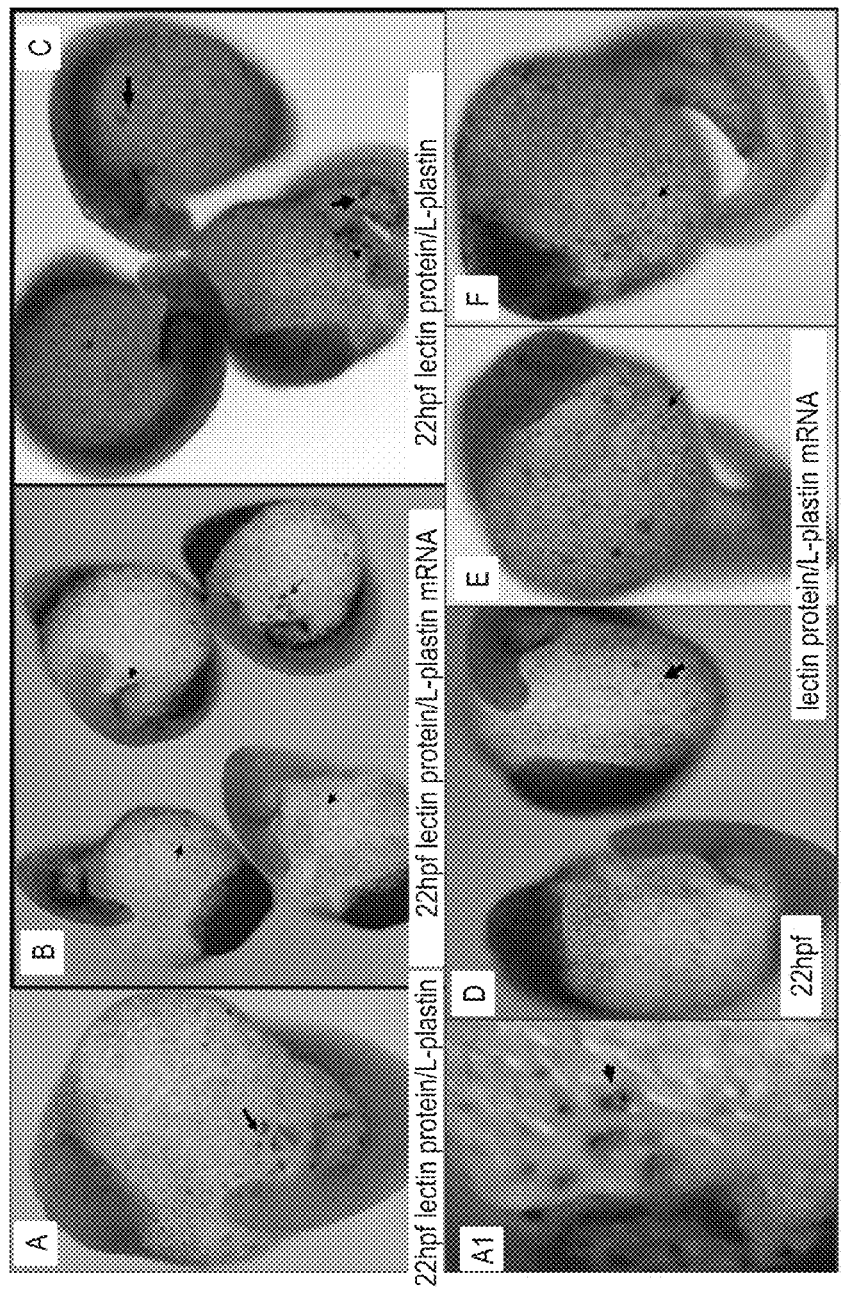

Using nucleotide probes to locate the expression of the new protein during fish embryonic development, we found the protein present in specific types of epidermal cells of fish embryos. Additionally, we found expression of the protein in both gametes as well as in the zygote. Furthermore, the protein was shown to be absent in most cells of the organisms, but expressed in a few embryonic cells which suggested that the protein could be tied to myelopoiesis (FIGS. 5 and 6). Such an expression pattern is unique. Thus, we chose the name "leukolectin" (abbreviated LL) for the protein.

Expression in Different Species

A survey of blood from fish to chicken to humans revealed that leukolectins are present in leukocytes throughout this vertebrate lineage. Its presence could also be detected in whole invertebrates using our polyclonal antibody. Finding leukolectins in (human) leukocytes immediately suggested possible functions for leukolectins. Leukolectin occurs in cells carrying out immune functions.

Figure 7:
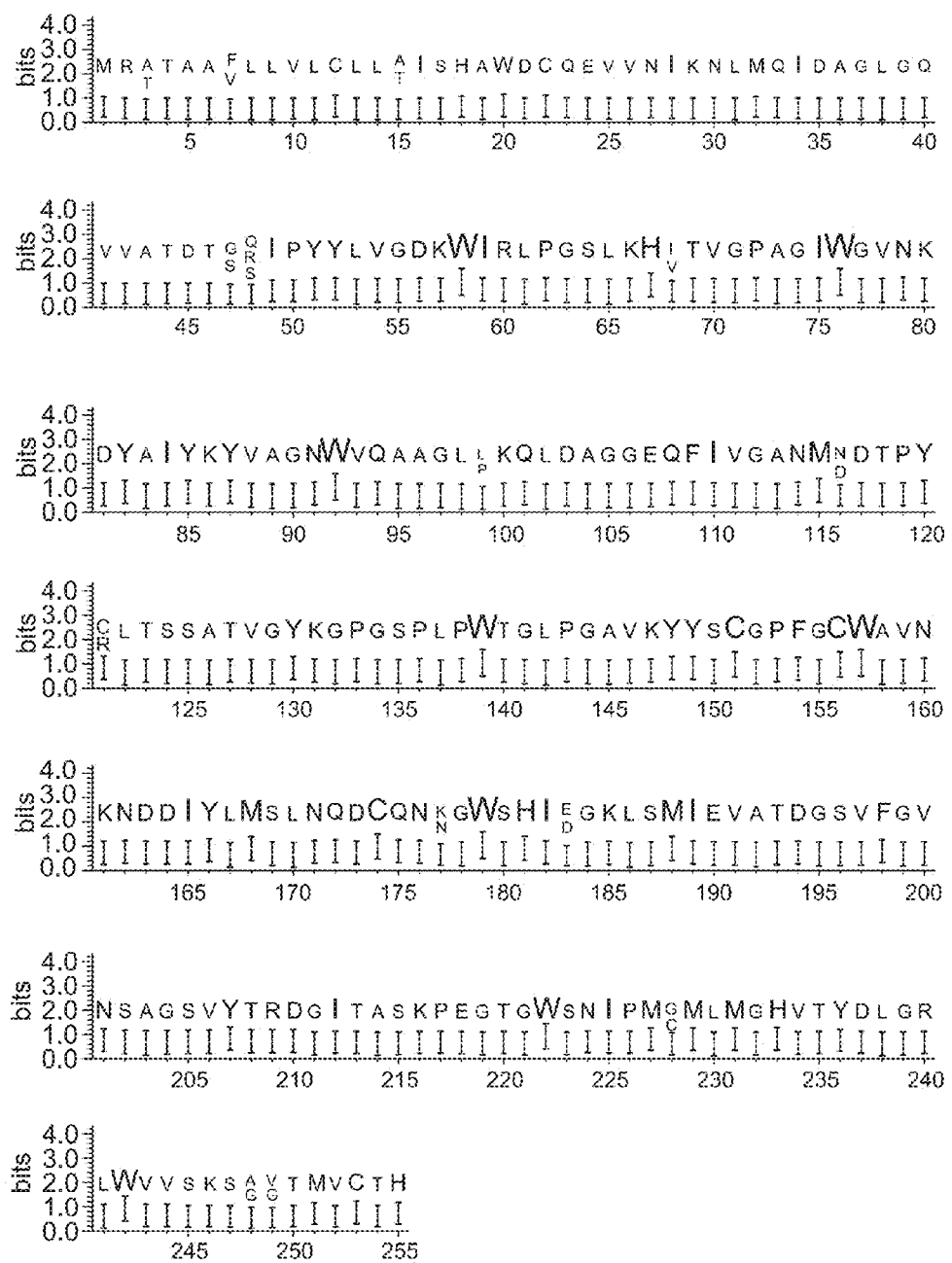

Most surprising was the extreme sequence invariance of leukolectins during evolution (FIG. 7). Using standard primer-pair technology we could detect cDNAs throughout the vertebrate lineage. Analysis revealed an extremely conserved sequence from fish to chicken to humans, which would point to essential functions for such genes. The variance between fish and human sequence is around 4% (10 variant AAs), or 96% similarity, where half of the observed variances were conservative AA substitutions. By comparison, the one fairly similar known protein is a fish egg lectin (FEL) from the common carp (less than 48% similarity).

The summary of variant LL structure (FIG. 7) defines the new LL-family of proteins. We see about 2% non-conservative changes in AA from fish to humans. Clearly, LL-genes code for proteins which are subjected to extreme evolutionary selection in order to maintain sequence invariability. This in turn points to important, but as yet unknown functions that prevent most random variation in the gene products from arising and taking hold during species evolution.

Recombinant Leukolectin Preparation cDNA of salmon Leukolectin was cloned from embryos. The PCR primers were designed to contain the NcoI restriction site (forward) and ACC65 I (reverse). Vector pETM-60 were digested with NcoI/ACC65I and digested PCR products were ligated by overnight-ligation. After plasmid amplification and sequencing, the pETM-60 expression vectors containing the sequence-verified Leukolectin insert were transformed in BL21 (DE3)p Lys competent cells and the colonies used to inoculate 5 mL of LB (=Luria Broth) for preparing bacterial glycerol stocks.

Bacterial culture and protein purification: The new bacterial vector pETM60-Leukolectin enabled the expression of His-tagged recombinant proteins fused to the C-terminus of NusA through a TEV protease recognition sequence. They were efficiently purified by metal affinity and recovered in soluble form after the removal of the fusion partner.

Materials and Methods:

PCR Upper and Lower Primers:

```
NWA15dPET(#23): NcoI
                                            (SEQ ID NO: 16)
5'-GCA.CCA.TGG.CCA.TGG.GCT.GGG.ACT.GTC.AGG.AGG.
TAG.TA

CH.A15dPET(#13): ACC65I
                                            (SEQ ID NO: 17)
5'-CCG.AAG.CTT.GGT.ACC.ATG.TGT.GCA.CAC.CAT.GGT.
GAC
```

PCR Mix:

| | |
|---|---|
| dNTP | 4 µl |
| Primer#23/#13 | 0.5 µl (10 µM) |
| cDNA | 2 µl |
| DNA polymerase buf. | 10 µl |
| DNA polymerase | 0.5 µl |
| dH$_2$O | to 50 µl |

PCR Reaction:

| | |
|---|---|
| 98° C. | 10 sec. |
| 55° C. | 15 sec. |
| 72° C. | 1 min. |
| 30 cycles | |
| 70° C. | 10 min. |

Both PCR product and pETM-60 plasmid were digested with NcoI and ACC65I restriction enzymes; and purified from 1% agarose gel for ligation.

Ligation of Insert DNA to the Vector by T4 DNA Ligase:

T4 ligase was used to join the 5' phosphate and the 3'-hydroxyl groups of double stranded DNA molecules using the following mix:

200 ng of vector DNA
500 ng of insert DNA
10× Ligase buffer
1 µl T4 Ligase
Volume to 10 µl Incubation was at room temperature overnight, and heat inactivation of the ligase was achieved by placing the tube in 65'C water bath for 10 minutes.

The ligation mix was electroporated in DH5α competent cells, and the colonies used to inoculate 5 ml of LB.

10 clones were randomly picked for analysis. Analysis was done by digestion of pETM60-Leukolectin with NcoI/ACC65I.

The sequence of insert Leukolectin was verified by sequencing of pETM60-Leukolectin with primers #13 and #23.

In Vitro Translation of Leukolectin

BL21(DE3)pLysS contains a plasmid (pLysS with chloramphenicol resistance) that encodes T7 lysozyme to reduce background levels of T7 polymerase prior to induction.

BL21(DE3)pLysS provides tighter control of protein expression of toxic proteins and is a strain for high-level protein expression and easy induction.

The fusion tag used in the recombinant protein expression and purification was NusA which has a 495aa (54.8 kDa) size and is located at the N-terminus and is used to enhance solution of proteins that are overexpressed.

NusA-Leukolectin was efficiently purified by metal affinity and recovered in soluble form after the removal of the fusion partner.

Materials for Expression and Purification of NusA-Leukolectin:
Kanamycin Plate
    2YTG medium
    0.4 mM IPTG (final concentration 0.4 μM.
    HisTrap HP (5 ml) column
    Induction was performed for 3 hours at 26'C.
Purification Protocol:
Inherent enzyme activity of the NusA-Leukolectin supernatant before purification: 0.0060/min Equilibration of the column with 25 ml buffer B (1×PBS, 30 mM imidazole, 0.4 M NaCl)

Sample Application:
28 ml of the supernatant were filtrated and degassed, and 25 ml of it applied to the column The column was washed with 75 ml buffer B. Elution was with 25 ml buffer C (1×PBS, 0.5 M imidazole, 0.4 M NaCl), with a one step elution. 1 ml samples were collected.

Figure 8:
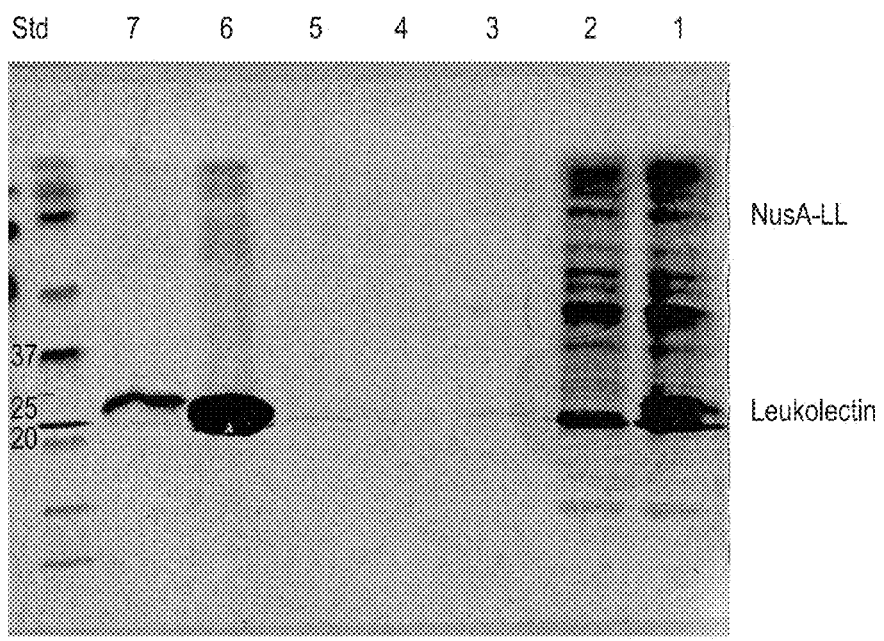
FIG. 8 shows coomassie-stained fractions after purification of recombinant leukolectin by column chromatography. The lanes are 1—supernatant, 2—flow-through, 3—wash, 4—F1, 5—F2, 6—Mix of F3, F4 and F5, 7—F6 and 8—STD.

Results:
Over 98% of the protease activity from the crude recombinant proteins was found in the flow-though and wash. Only 1.6% of the protease activity was recovered in column fractions including the ones (F6 & F7) with the recombinant Leukolectin, identified by SDS-PAGE analysis (see FIG. 8). These fractions contained 0.3% (background levels of protease activity applied to the column).

Conclusion:
Recombinant leukolectin is devoid of serine protease activity, and is thus a true lectin.

The traces of serine protease activity found in some leukolectin preparations from natural source (hatching fluid) must therefore represent traces of zonase.

Leukolectin and Zonase co-exist in hatching fluid, and tend to co-purify during most chromatographic procedures, but may be separated by final ultrafiltration using 100 kDa exclusion size Biomax filters.

Recombinant Protein Analysis

Recombinant salmon LL produced as above and purified by SDS PAGE was analyzed by MS/MS techniques. LL's Peptide Mass Fingerprint spectrum was analyzed in Mascot both in NCBI protein and EST databases for Actinopterygii without finding any significant hits (Riste, unpublished). These spectra compared well with LL spectra obtained from embryonic and leukocytic LL moieties eluted from 2D-gel analysis of such LLs, further confirming the existence of isoforms of LL observed by pH-gradient methods.

Genomic Sequence

In salmon we have established the genomic sequence of genes for this entity by probing Bac-libraries with a 670 NT probe (a full protocol is also described in detail in Example 10). Thus, a full length cDNA sequence for Leukolectin was available from use of degenerate primers designed based on information derived from partial protein AA sequences. PCR-amplifications of cDNA from 370 dd (day degrees) embryos (i.e., embryos close to, but still not hatching) generated the amplikon of 630 bp, which was gel-purified and sequenced.

Lectin gene-specific probes were used to screen a BAC library (18× coverage; average insert size, 188 kb), which was made available by the Salmon Genome Project (SGP) consortium. Probes (size 630 bp) were prepared by incorporating digoxigenin-11-dUTP (Roche) using the PCR method. Screening of the Bac library resulted in the identification of 7 positive clones characterized as A-12/144, L16/143, P6/76, B-5/70, O-20/85, L-7/257, F-7/176. Positive responses are exemplified in Panels A&B.

Specific responses of the selected clones were confirmed by PCR amplification using the same primers as for the DNA-labelled probe used for screening of the BAC-library. The size of the insert inside the vector sequence was estimated by pulse field electrophoresis. Clones were sequenced commercially (MWG-Biotech, Germany) by the shotgun method.

This work established several closely related genes for leukolectins in the genome of the (tetraploid) salmon (FIGS. 9A and B). A variance in segmental sequences would seem to suggest the existence of at least two similar genes. Structurally, leukolectins appear as normal genes with 5 exons and 4 introns, in a gene about 2300 bp from transcription start to the polyadenylation site, a fairly standard size.

Nevertheless, our data enabled us to determine that no genes with a similar sequence had been reported in any organisms to date. Using probes to individual exons or introns, we could establish only the rare similarity of one exon to parts of two other reported proteins, which both are totally unlike the molecular entity we have discovered.

Databases searches indicate that no gene can be found which corresponds to the LL protein, the mRNA transcript of LL, or to the genomic gene for Leukolectin in human chromosomes. Apparently, the Leukolectin gene is either not yet found anywhere, or its sequence is not yet deposited, or the LL gene sequence has not yet been detected in humans. In further searches we used individual small structural elements listed in the Table 2 below, in order to locate such elements in the data bases.

TABLE 2

| LL exon/intron | Length (NTs) | Hits |
|---|---|---|
| From Ts - Start to exon I | 51 | None |
| Exon I | 55 | Chrom. 11, 7, 1, 18, 17, 10 |
| Exon I + intron I | 55 + 89 | Chrom. 11, 14, 18, 13 |
| Exon II | 234 | Protocadherin region, thiamin triphosp. enz. |
| Exon II + intron II | 234 + 163 | none |
| Exon III | 218 | Smooth muscle protein, Tcell Receptor, etc. |
| Exon III + intron III | 218 + 133 | T cell Receptor beta chain V region |
| Exon IV | 116 | None; Chrom. 20 & 21 |
| Exon IV + intron IV | 116 + 682 | Chromosome 8 (x2) |
| Exon V | 142 | None; some ? |
| Exon V + intron V | 142 + 404 | Chromosomes 5 & 4 |
| Ts—Start to polyA end | 2283 | None; some ? |
| cDNA | 765 | None |
| LL Protein | 255 AA | None |
| Intron I | 89 | Chrom. 3, 4, 18, 14 |
| Intron II | 163 | Chrom. 14, X, 4 |
| Intron III | 133 | Chrom. 21, 2, 7, 4, 15, 13, 18, 12, 8, 1, |
| Intron IV | 682 | Chrom. 18 (x2) |
| Intron V | 404 | None; some ? |

The results indicate that some known proteins exhibited some degree of similarity to parts of Leukolectin—the relevant chromosome numbers are provided. Sequences not located to chromosomes are stated as "some ?".

The primary hit was human Transgelin, which is a smooth muscle protein 22-alpha (SM22-alpha) (WS3-10). Transgelin is an actin-binding protein, and is one of the earliest markers of differentiated smooth muscle. The function of this protein has not yet been determined http://harvester.embl.de/harvester/P378/P37802.htm However, aligning protein-sequences of Trangelin and Leukolectin showed minimal consensus sequences. Otherwise, some small similarity in parts of the LL structure was found with respect to a T-cell receptor and with an unknown protein Importantly, this novel gene is specifically expressed in human leukocytes, despite the fact that this gene cannot (yet) be found in published sequences of the human genome. (Some expression is also seen in purified preparations of human thrombocytes.) Only very short segments of this gene may be detected in the human genome, but these segments are widely spread over a multitude of human chromosomes (see FIG. 10).

The observed pattern of distribution on chromosomes is baffling. Such short sequences may not be related to the LL-gene, if the human LL-gene itself until now has not been sequenced or located to a specific chromosome. The resolution of this conundrum is as yet not at hand.

Discussion

A new LL-lectin has been identified in human leukocyte which is nearly identical to LL from fish and chicken. The LL gene in salmon is of standard structure but is not yet found in humans.

EXAMPLE 2

Medical Applications of Leukolectin

Materials and Methods

The following studies were carried out using the salmon leukolectin protein (referred to as LL), prepared as described in Example 1. LL-concentration used was ca. 1-10 microgram/ml. Zonase-protease was present with LL in a ratio of 1:100 in a water and coconut oil emulsion (in which over 30% coconut oil is present). Leukolectin is stable in the presence of zonase.

Results

A. Cold-Cracked Skin

Many people experience seasonal cracking of the skin, particularly on the hands.

Application of leukolectin to the skin during onset of the cold season postponed dramatically, or in many instances prevented, the onset of cold cracks. This phenomenon has been recorded in a dozen cases. Observations on the effects on established cold-cracks of LL are fewer, but some closing of established cold wounds have been revealed.

B. Sunburn-Damaged Skin

Excessive solar exposure to naked skin may cause sunburns, and result in heat sensations, redness, itching and eventual flaking off of the exposed skin.

Application of leukolectin resulted in the fading of redness in minutes, in the cessation of itching and in the eventual non-occurrence of skin flaking. These amazing observations have been repeatedly observed in many individuals.

C. Heat-Damaged Skin

After direct damage by heat to the skin, application of salmon leukolectin seemed to prevent normal consequences of such damage to a considerable extent, and to arrest the damage if applied some time after the original damage and to speed full recovery.

D. Acne

Sub-clinical cases of acne have responded in many juveniles by an immediate cessation of itching and of redness Improvement of acnes per se has been seen in a small pilot study in about half of the cases upon application of LL in the coconut oil emulsion.

E. Topical Psoriasis

Large patches of psoriatic skin have responded to application of salmon leukolectin with first, an almost immediate receding of redness, followed by drastically reduced sensation of itching. The excess congregation of horny skin retracted over the first few weeks, but reoccurred upon cessation of LL application.

F. Open Skin Wounds

Observations were made on human volunteers. We studied cases of chronic open and oozing skin wounds which had resulted from compression heel wounds after broken hip surgery, and which had been unsuccessfully attended by health personnel for months and up to a year. Sores seen were from one half to two cm in diameter.

Upon application of filter-sterilized LL preparations to chronically open wounds on the lower extremities (legs), we observed that liquid stopped oozing from wounds after 2-3 days, followed by rapid shrinking of the wound area, so that after 2-3 weeks, the wounds were vanishing and being replaced by normal skin.

Given the nature of the patients with wounds first appearing on the far end of extremities, we observed that the first wounds to disappear in the above manner were the proximal wounds. This we interpret as the more recently established wounds. The last wounds to disappear were the distal wounds close to the heel, which are the longest-established wounds. Eventually all wounds disappeared.

G. In Vitro Studies

Differentiated human skin epithelium cultures were obtained from SkinEthics (Nice, France) at day 16 after seeding onto plastic growth substrata with micropores allowing nutrients access to the epithelial tissue from below. Such cultures exhibit normal skin morphology after differentiation during the culturing period at 37° C. These cultures were maintained for two more days in vitro so that the upper stratum corneum was exposed to air, and stratum basalis to the growth substratum. Parallel cultures were moved to 30° C. moist atmosphere and presented with a medium Ca, Mg-containing phosphate-buffered saline for 6 hours with or without the presence of 10 µg/ml of salmon leukolectin. Cultures were fixed in formalin and embedded in paraffin according to standard procedures, and stained with hematoxylin/eosin. Rapid induction of large basal cells was observed in the epidermis, with signs of cell proliferation (FIG. 11). We interpret such results to be causally related to the healing effects of leukolectin on skin, in which a combination of cell proliferation and cell differentiation suffices to close the wound and to re-establish skin epithelial integrity.

Discussion:

We have not found expression of LL-gene products in cell cultures of keratinocytes. Also, dendritic cells are the only cells in the epithelial skin related to blood leukocytes. Normal access of leukocytes to the epithelial skin is interfered with after some mechanical or biological insult due to poor circulation, which is where compression wounds often occur in the normal skin. Administration of leukolectin overrides this deficiency and triggers normal mechanisms of healing in the skin.

EXAMPLE 3

Leukolectin Protein Expression in Leukocytes

Salmon blood was obtained from Industrilab, Univ. of Bergen. Whole fish blood was collected in heparinised tubes (Riste, unpublished), and processed according to Miller et al. (1988, Nucleic Acids Research, 16(3) p 1215). Human blood samples were obtained from the Blood Bank at Haukeland University Hospital, Norway.

Whole human blood was collected in 5 ml citrate-buffered tubes, and processed according to Miller et al. (1988, supra) to prepare leukocytes. This preparation was further purified by the Lymphoprep™ (Axis-Shield PoC, Norway) enrichment. Lymphoprep™ was used according to its protocol to prepare a human leukocyte fraction. This fraction was used for immunoblot analysis, as described in Miftari and Walther (unpublished). Analysis by 2D PAGE followed the procedures described by MacGillivray and Rickwood (1974, European Journal of Biochemistry, 41, pp. 181-190), with ~1 µg protein. The LL proteins from these two species were visualized by 2D PAGE using immunoblots for specific detection of LL proteins and their isoforms. Treatments with polyclonal primary antibody to salmon LL followed by goat anti-rabbit antibody, allowed visualizing LL-proteins by ECL-enhanced detection system. The specificity of the immunoreaction was tested in multiple gels applying from 0.5-5 µg of protein, with similar results.

Salmon leukocytes exhibit 2 LL-isoforms of MW ~26 kDa, with pI similar to the more basic forms of the 8 LL isoelectric forms found in salmon PVF. It is difficult to estimate exact MWs by extrapolation from MW standards in the second dimension of 2D PAGE. Human leukocytes contain one main LL-antigen of molecular weight ~30 kDa, which from other observations is close to 27 kDa. The acidic pI corresponds to the average pI of salmon LL-isoforms found in PVF (Riste, supra) (see FIG. 12).

EXAMPLE 4

Salmon Leukolectin Transcripts Identified in Northern Blots

Salmon eggs were obtained from a farmed salmon broodstock at Bolaks as (Fusa, Norway), maintained for multiple generations since 1975 by phenotypic selection, and now part of the salmon stock propagated by Salmo Breed A/S, Norway.

Isolating Total RNA and Polyadenylated RNA

Total RNA was isolated from salmon embryo at later, pre-hatching stages (around 370 dd) using Trizol reagent (Life Technologies) according to manufacturer's instructions. The quality and quantity of total RNA in terms of integrity and purity was assessed on a formaldehyde agarose gel stained with ethidium bromide. Total RNA was quantified spectrophotometrically. The polyadenylated fraction of RNA (mRNA) was isolated from 5-10 µg of total RNA using Dynal beads mRNA purification kit (Invitrogen).

Construction of Probes

Antisense Digoxigenin (DIG) labelled cRNA probe was generated by transcription of SP1 digested plasmid DNA templates with T3 RNA polymerase. Sense DIG-labelled cRNA probe was generated by transcription of XhoI digested plasmid DNA template with T7 RNA polymerase (sense) using DIG RNA Labelling Kit (SP6/T7) (Roche Diagnostics) according to manufacturer's protocols. The digoxigenin (DIG)-labeled LL antisense and sense cRNA probes generated spanned ~650 bp.

Northern Blotting Analysis

Aliquots of 0.5 µg pure mRNA and 1 µg total RNA were electrophoresed and blotted onto positively charged nitrocellulose membrane (Amersham). Membranes were pre-hybridized in DIG Easy Hyb buffer (Roche) at 55° C. for 2 h, and then hybridized at 55° C. for 16 h, with 1 µg/ml LL riboprobe. The washing was performed twice at low stringency in 2×SSC with 0.1% SDS at RT for 15 min each, and twice at high stringency in 0.1×SSC with 0.1% SDS at 65° C. for 20 min each. The membranes were incubated in a blocking solution containing maleic acid buffer (pH 7.5) and 1% blocking reagent (Roche) and subsequently in the blocking solution with anti-DIG-alkaline phosphatase (AP) conjugated antibody (Roche) diluted 1:10,000 at RT for 1 h. After washing with 100 mM maleic acid buffer (pH 7.5) containing 150 mM NaCl and 0.5% Tween 20, the membrane was equilibrated 2 min in detection buffer (0.1 M TrisHCl, 0.1 M NaCl, pH 9.5 at RT). Hybrid probe targets were visualised by chemiluminescent assay using CSPD (Roche) as a substrate, and exposure of the blots to X-ray film (Kodak) for 5-30 min. DIG-labelled RNA molecular weight marker (Roche) was used.

Figure 13B:
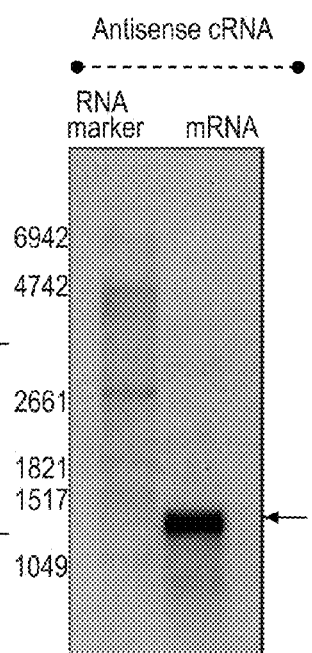
Figure 13C:
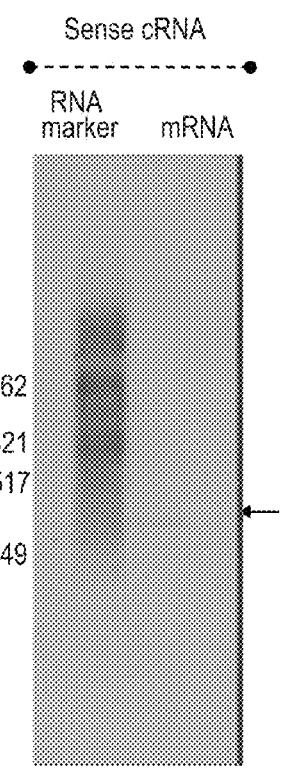

Antisense DIG labelled LL specific riboprobe was used to estimate the size of mature LL transcripts. Northern blot analysis of total RNA (FIG. 13A) revealed a major transcript with the size ~1250 bp, and also a weaker band transcript (~3200 bp) was observed. The dominant band corresponds to a transcript of the mature (intron-less) and translatable LL transcript. Northern blot analysis of purified mRNA using the same riboprobe revealed a single band of ~1250 bp (indicating that the amplified cDNA was close to a full length coding sequence (FIG. 13B). When blots from total RNA and mRNA samples were incubated with a sense LL specific riboprobe absence of a hybridisation signal was observed indicating that the riboprobe that was used was sufficiently specific (FIG. 13C). The minor transcript (~3200 bp) is larger than the full length LL-transcript for salmon. Given the specific conditions for hybridization, this entity probably does reflect an entity containing LL-sequence information. The positive signals from only antisense-probes and not from sense probes, underscore the specificity of the results. The size of the full-length transcript accommodates all LL-exons described above.

EXAMPLE 5

Alignment of LL with Related β-Propeller Proteins

Bioinformatic analyses were carried out on salmon LL sequences compared to information deposited in public sequence banks.

Clustal W analysis (FIG. 14) indicated that the deduced amino acid sequence of salmon leukolectin did not share significant sequence similarity with any reported proteins in the data bank. However, BLAST reveals similarities to more distantly related proteins, including FEL, a fish egg derived lectin from Cyprinus carpio (Gene bank Acc. Nr. P68512) with overall similarity of only 48% (E values of 2.00 E-50). In addition, a hypothetical protein from zebrafish (HPZ; Acc. Nr. LOC678590) exhibited an overall similarity of 45% (E-values of 2.00 E-48). Sequence comparisons also demonstrated that leukolectin was 38%, 28% and 26% identical to TPL-1 (previously Lectin L6) from Horseshoe crab (Acc. Nr.P82151), tectonin I from Physarum polycephalum) (Acc. Nr. 061063) and Tectonin II (061064). (By SwissProt, these numbers were 49, -, 35, 32 and 29% identities, respectively, and E-value for FEL 1 e-51 and for L6, 1 e-40). Our data suggest a higher similarity of LL to the vertebrate than to invertebrate counterparts. Not included, is a 30% identity of LL with human tectonin β-propeller Repeat-containing Protein (KIAAO329_human).

Multiple alignments revealed that of the four biochemically confirmed disulphide bonds in FEL (Galliano et al., 2003, Biochem. J. 376, pp. 433-440), three seem to be conserved in leukolectin. The first bridge connects the N-terminal end to the C-terminal end of both proteins. The bridge connects cysteines at positions 3 and 234 in LL (or 238 in FEL)). The second and third bridges connect Cys 102 to Cys 155 in LL (#157 in FEL), and Cys 132 and Cys 137 in both LL and FEL. The fourth disulphide bond found in carp FEL, involving Cys 208 (212) and Cys 226 (230) is not found in leukolectin.

EXAMPLE 6

3D-Model of LL (Leukolectin)

The leukolectin protein shares a high degree of similarity in terms of TECPR domain architecture with L6 or tachylectin 1 (*Tachypleus tridentaus*), a bacterial lipopolysaccharide-binding lectin from horseshoe crab hemocytes, and other invertebrate tachylectin-related proteins. Nevertheless, differences in terms of the number of domains, along with a slight shift of the β-propeller domains toward the C-terminal of the protein, were observed. Summarizing the information from similarity searches and the SMART searches, we infer that the overall 3-D structure of the leukolectin exhibits a 5-bladed β-propeller protein structure. On this basis we invoke the 3D model (Biesel et al., 1999, EMBO J., 18, pp. 2313-2322) to give a working model of how the leukolectin protein may look. This is only an approximation, as residue numbers from one protein are set equal to residues in the other. Searches in the SMART database indicate a prominent structural feature of the virtually translated leukolectin protein, which consists of five tandem repeats, each containing 35-36 AAs with 32-61% internal sequence identities (FIG. 15, right panel). Internal repeat stretches of the deduced leukolectin protein showed similarity among themselves, being mostly 13 AAs long. Two short consensus sequences, XWXXLPGXLKXXXVGPX (SEQ ID NO:18) and GVNKNDXXYXLVG (SEQ ID NO:19), are highly conserved in each repeat. Apart from a stretch of 20 residues in the N-terminal region of leukolectin, which is not found in the FEL, both proteins show a high degree of similarity between the number and overall domain architecture of TECPR domains, while sharing only 48% sequence identity.

EXAMPLE 7

Purification of Zonase from Salmon Hatching Fluid

The salmon hatching fluid in Example 1 may be further purified to yield a pure zonase preparation. One round of gel filtration was sufficient to separate zonase from the larger molecular components in the filtrate with a 12 fold purification with better than a 50% yield. The matrix utilized may vary, but Sephacryl SR-200® was our usual choice. The buffer was Tris-HCl pH 8.0 or pH 8.5 (0.05 M) or Tris-Acetate (0.025 M, same pHs). The zonase obtained after gel filtration procedures accounted for the predominant zonase moieties in the hatching fluid.

Zonase was purified to a homogeneous protein product by affinity chromatography on commercially available Benzamidine Sepharose 6B®-columns. The specific conditions utilized (with columns of 25 or 125 ml volumes) was again a 0.05 M Tris-HCl buffer (pH 8 or 8.5), which for removing non-specifically bound material on the columns, was adjusted to 1 M NaCl. Zonase was not removed by this step, as the protein remained tightly bound to the column. Elution of zonase from the column was achieved by using a 10-33% dioxane-gradient in 1 M NaCl in the same Tris-HCl buffer. After affinity-purification, the zonase preparation exhibited one protein band on SDS-PAGE analysis, with a molecular weight of around 28 kDa. Whilst, this zonase product was not of sequence-grade purity it was highly purified.

Gel filtration-purified plus affinity-purified zonase was further purified to sequence-grade purity by one final chromatographic procedure. This procedure employed a PBE94® column, with a buffer of Tris-Acetate (10 mM, pH 9.0), where subsequent elution was with a salt gradient (up to 1 M NaCl salt) in this buffer. This step itself increased the catalytic activity of the zonase by a further 7.6 fold, for an overall purification of 714 fold, and with a yield of 28% from the starting material. This purification step left the protein identity of the zonase intact as a 28 kDa moiety.

EXAMPLE 8

Production and Purification of LL Antibodies

Polyclonal rabbit anti-rabbit anti-salmon LL antiserum was prepared as follows: Sequence grade purified leukolectin protein from Example 1 was used for raising polyclonal antibody in 4 kg Chinchilla rabbit, as described by Harlow and Lane (1988, Laboratory Manual, Cold Spring Harbor, N.Y.). Three injections of 80, 40 and 25 mg of sequence-grade leukolectin were placed in multiple subcutaneous sites. The first was emulsified with Freund's complete adjuvant, the last two with incomplete adjuvant after 3 and 6 weeks. Eight days after the final booster, blood was collected and serum prepared after centrifugation at 3,000 rpm (Sorvall SS-34 rotor) for 15 min Aliquots of the antiserum were stored at −80° C. Primary antibodies were affinity-purified using HiTrap 1-ml Protein G columns (Amersham Pharmacia Biotech) with flow rate 1 ml/min. Whole antiserum was filtrated through 45 μm filter unit before being applied to one ml Protein G columns. The column equilibration was carried out using 5-10 column volumes of binding buffer (20 mM Na phosphate, pH 7.0) followed by several washes with the same buffer until no protein was detected by UV absorbance at 280 nm. IgG fraction was eluted with 5 ml of elution buffer (0.1 M glycine HCl, pH 2.7) and divided into 10 tubes containing 25 μl of neutralisation buffer (1 M TrisHCl, pH 9.0). Concentration was determined spectrophotometrically. Purity was estimated by analysing the aliquots of purified IgG fractions in 12% SDS-PAGE with subsequent silver staining Sensitivity was determined by Western blot analysis using goat anti-rabbit IgG, horse radish peroxidase conjugated secondary antibody.

Additionally, polyclonal antibodies were preadsorbed by incubation in zebrafish acetone powder. Fluorescein isothiocyanate (FITC)-labelled swine anti-rabbit F(ab')2 was from Dako (F-0054). Alexa Fluor 647-labelled goat anti-rabbit IgG was obtained from Molecular Probe, Eugene, US (Invitrogen, catalog nr.A-21244) and biotinylated polyclonal swine anti-rabbit immunoglobulins was from Dako (catalog nr.E0353). The optimal concentrations of the primary and secondary antibodies were determined by prior dilution experiments. The polyclonal antibodies were used in the protein expression analysis described in Example 1.

EXAMPLE 9

Identification and Characterisation of LL from Zebrafish

Total RNA was isolated from zebrafish embryo at 4, 6, 12, 24, 48 hpf and 5 dph using Trizol procedure (Life Technologies) according to manufacturer's instructions. The integrity and purity of total RNA was assessed on a formaldehyde agarose gel stained with ethidium bromide. Only samples with a ratio of 28S to 18S rRNA of 2-2.4:1, and no detectable DNA contamination, were used. RNA was quantified spectrophotometrically. Polyadenylated mRNA was isolated from 5-10 µg of RNA using Dynal kits (Invitrogen).

Reverse transcription was performed using 200 U/µl TermoScript (Invitrogen). mRNA (0.5 µg) was heated to 72° C. for 5 min, cooled, pelleted and added to a 20 nl reaction mixture containing 100 ng/µl oligo dT, 10 µM DDT, and 0.8 U/µl RNAse Inhibitor in 2.0 mM cDNA synthesis buffer (Invitrogen). Incubation was at 50° C. for 1 h. Products were purified by phenol/chloroform/isoamyl alcohol extraction, passed through MicroSpin S-200HR column, and ethanol-precipitated. Gene-specific LL primers were designed from salmon LL sequences (Table 3). The PCR mix (20 µl) contained 2 nl of cDNA template, 0.4 µM of primers (LLF1, LLF2, LLR1, LLR2, and LLR3), lx PCR buffer, 0.5 U Taq DNA polymerase (Takara), and 0.2 mM of dNTPs. PCR amplification used 32 cycles of 94° C. for 45 s/58° C. for 45 s/72° C. for 90 s and final extension at 72° C. for 7 min. The reaction mixture was analysed by 1.8% agarose-TBE gel with 0.5 µg/ml ethidium bromide in 1×TBE buffer (pH 8.3) with DNA marker 100 bp ladder (New England Biolabs).

The PCR fragment was ligated into a pGEM T-Easy Vector system 1 (Promega, Madison, Wis.) by standard protocols.

Electroporation used 40 µL of *E. coli* DH5α, and 1 µL of ligated PCR fragment in the pGEM T-Easy Vector. SOC medium (1 ml) was added before bacteria were incubated at 37° C. for 1 h. The recombinant bacteria (200 µL) were plated on standard LB/ampicillin, X-gal, IPTG agar plates and incubated at 37° C. overnight for blue/white screening. Ten white clones were picked and grown in a 5 mL overnight culture in LB medium with 100 µg/mL ampicillin. Plasmid purification used Plasmid Minipurification kit (Qiagen, Chatsworth, Calif.). Plasmids were amplified and sequenced using standard protocols (DNA Sequence Lab, Bergen).

5'- and 3'-RACE PCRs of LL were performed using the GeneRacer core kit (Invitrogen cat. #45-0168) according to instructions. 2 µg of total RNA was used to synthesize the first-strand cDNA in RT using Superscript III (Invitrogen). First round 5'- and 3'-RACE PCR amplification was performed applying 5'- or 3'-GeneRacer primer and reverse or forward gene specific primer LLR2 & LLF3 (Table 3). Nested 5'- or 3'-RACE PCR amplification employed nested 5'- or 3'-RACE PCR GeneRacer primer and nested reverse or forward gene specific primer LLR4 & LLF4. For 5'- and 3'-RACE PCR, first step five cycles, 94° C. for 30 sec and 72° C. for 1 min; next five cycles at 94° C. for 30 sec and 70° C. for 1 min; third step 30 cycles with 94° C. for 30 sec, and 68° C. for 45 sec and 72° C. for 1 min; final extension step 72° C. for 7 min. Nested 5- or 3'-RACE PCR in three steps: first step 5 cycles at 94° C. for 30 sec, 72° C. for 2 min; next step 5 cycles 94° C., 30 sec, 70° C. 2 min; 3 step 25 cycles 94° C. for 30 sec, 65° C. for 30 sec and 68° C. for 1 min; final extension

TABLE 3

Primers used for zebrafish LL amplification

| RT-PCR Primer | Sequence | Position (nt) | Expected size (bp) |
|---|---|---|---|
| $LLF_1$ | 5'-ATGCAGATCGATGCAGGACTGGG-3' (SEQ ID NO: 20) | 94-116 | F1/R1 = ~720 |
| $LLF_2$ | 5'-TGGTTCCCTGAAGCATGTCACTGT-3' (SEQ ID NO: 21) | 186-209 | F1/R2 = ~454<br>F1/R3 = ~340 |
| $LLR_1$ | 5'-GAAAGAGAGATCAATGAGTTCGCA-3' (SEQ ID NO: 22) | 840-817 | F2/R1 = ~655 |
| $LLR_2$ | 5'-CAAAGACACTACCATCAGTTGCCAC-3' (SEQ ID NO: 23) | 595-571 | F2/R2 = ~410 |
| $LLR_3$ | 5'-GTCCGCAGCTGTAGTACTTCACAG-3' (SEQ ID NO: 24) | 457-434 | F2/R3 = ~300 |

| 5' RACE-PCR Primer | Sequence | Primer | Sequence |
|---|---|---|---|
| GeneRacer 5' Primer | 5'-CGACTGGAGCACGAGGACACTGA-3' (SEQ ID NO: 25) | Gene Racer 3' Primer | 5'-GCTGTCAACGATACGCTACGTAACG-3' (SEQ ID NO: 28) |
| GeneRacer 5' Nested Primer | 5'-GGACACTGACATGGACTGAAGGAG TA-3' (SEQ ID NO: 26) | GeneRacer 3' Nested Primer | 5'-CGCTACGTAACGGCATGACAGTG-3' (SEQ ID NO: 29) |
| $LLR_2$ | 5'-CAAAGACACTACCATCAGTTGCCAC-3' (SEQ ID NO: 23) | $LLF_2$ | 5'-TGGTTCCCTGAAGCATGTCACTGT-3' (SEQ ID NO: 21) |
| $LLR_4$ | 5'-AGCCTGGACCCTTGTAGCCAACTGT-3' (SEQ ID NO: 27) | $LLF_4$ | 5'-GTGAGGTGGCAACTGATGGTAGTGTCT-3' (SEQ ID NO: 30) | step 72° C. for 10 min Templates for nested PCR used PCR product from first round RACE PCR diluted 1:25 in distilled water.

Primers for RACE PCR are listed in Table 3. Single PCR products were purified using PCR purification kit (Promega, Madison, Wis., US), and ligated into PCR II Topo vector (Invitrogen) for transformation of JM109 high-efficiency competent E. coli (Invitrogen). Recombinant bacteria were identified by blue/white screening on Lucia Bertani agar plates. Plasmids containing the inserts were purified using Promega purification kit and sequenced with M13 primers. The LL mRNA sequence was analysed using the Blastx and Blastp search programs.

By combining three sets of primers (see Table 3), amplification gave amplicons of sizes (FIG. 16A) predicted from salmon LL. The water blank without zebrafish mRNA was negative. The largest product (720 bp) was sequenced, proving that LL is present in zebrafish. Amplification of different sized PCR products (FIG. 16A) primed by specific oligonucleotides flanking the salmon exons in different positions, further documented high homology between zebrafish and salmon LLs. As a positive control for the amplification reactions, we used β-actin.

Figure 16A:
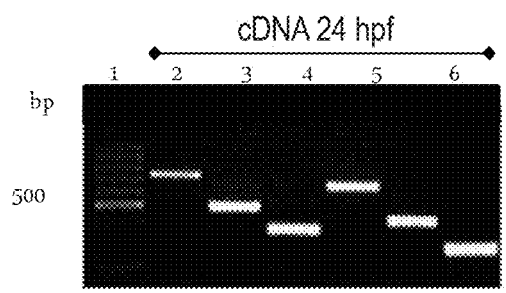
Figure 16B:
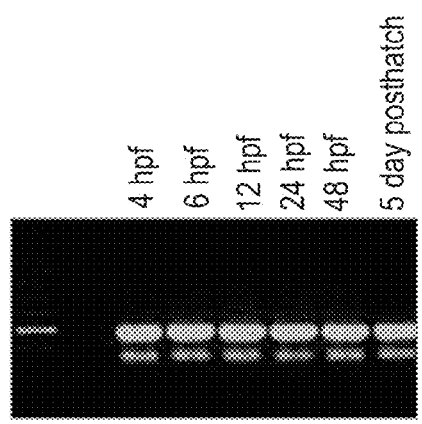
Figure 16C:
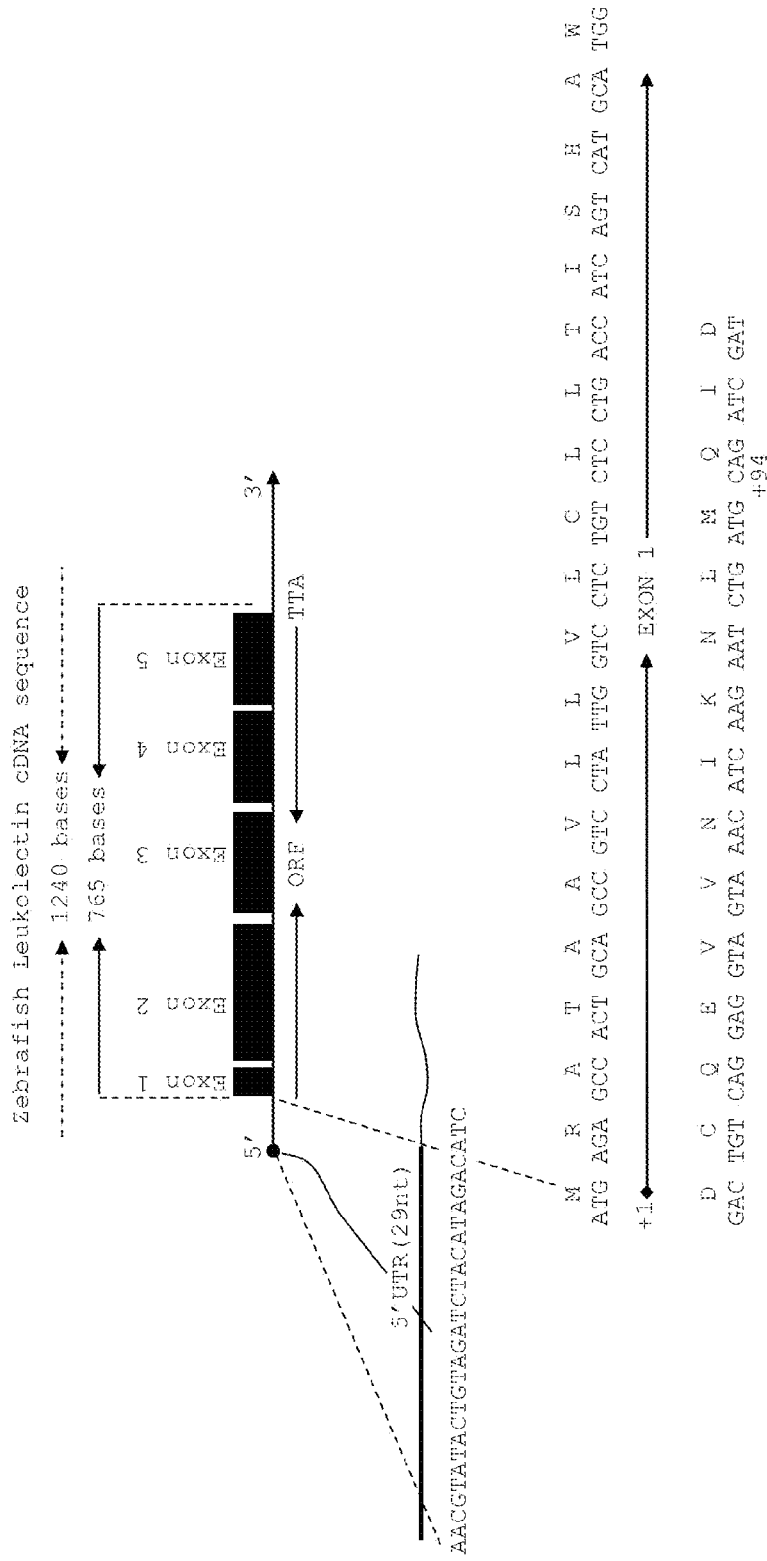
Figure 16D:
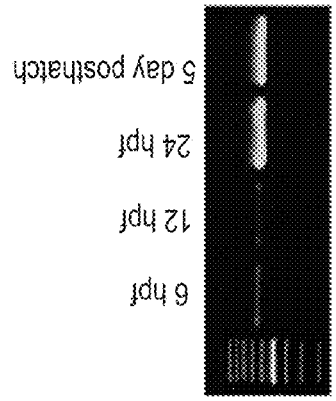

5'-RACE PCR clarified the sequence of 5'-untranslated (5'-UTR) region of zebrafish LL. We used mRNA (FIG. 16B) from 4 hours post fertilization (hpf) until 5 days posthatching (dph). First round of RACE PCR amplification yielded very weak products. Such amplified products from all stages were used for second round RACE PCR using high annealing temperature (65° C.) in order to increase the specificity of the reaction, using a 1:20 dilutions of the first RACE PCR reaction. The same two products (520 and 420 bp) were generated from all stages (FIG. 16B), even from 4 hpf. From these developmental stages, LL-sequence information from more than 20 clones was obtained. All clones contained the 29 nts upstream region (FIG. 16C) detected in salmon LL. The 3'-end was also sequenced by multiple analysis and revealed a structure very similar (almost identical) to the structure found in salmon leukolectin. Based on the full length cDNA sequence, the deduced zebrafish LL-protein was deposited in the NCBI Gene Bank (Acc.nr. FJ 643620). The encoding sequence consists of 1,213 nts with an open reading frame of 765 nucleotides. The deduced amino acid sequence for zebrafish LL suggests a protein of 255 AAs, given a translation start codon at nt position +1 (or nts 30-32; (FIG. 16C). LL cDNA also has a potential start codon at nt +94 (FIG. 16C). In 4 of 20 zebrafish LL clones, the transcript contained the 29 nts upstream from the +1 site, but lacked the next 93 nts (the nt-sequence read correctly up till −1 followed by the nt at +94: FIG. 16C). Thus, the data suggest that two different LL-proteins may be translated (FIG. 16C).

Figure 16E:
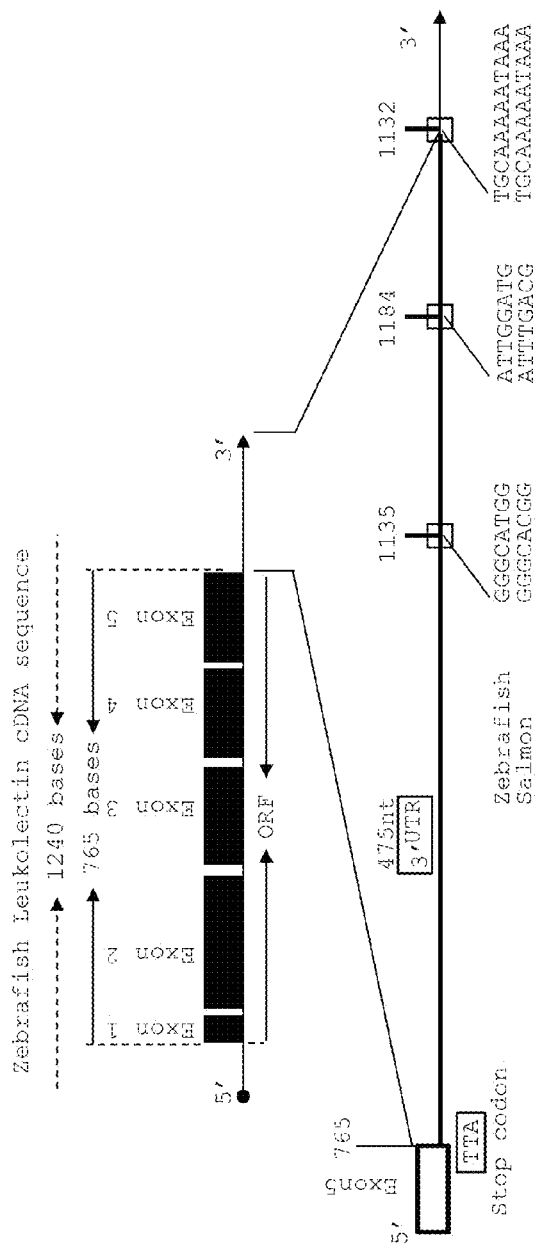

Strong homology between zebrafish and salmon LL proteins was apparent. Zebrafish LL is a hybrid structure compared to the two salmon LLs. Of seven LL-classification criteria established, 4 criteria placed zebrafish LL in category LL-1, while 2 criteria placed it in category LL-2 (FIG. 16E). The seventh criterion is unique for zebrafish LL (FIG. 16E, boxed area). Furthermore, one Cys is missing in exon 3 and replaced by Arg in the sequence "nmnTPYClts", which in zebrafish reads "nmnDTPRlts". In consequence, zebrafish LL has 5 cysteines, where salmon has 6 cysteines, all predicted in disulfide bridges.

Concerning the various exons, exon 1 is identical, while zebrafish exon 2 has three unique AAs not found in salmon (Gly-Arg instead of Ser-Gln at positions #57 & 58, and Val instead of He at position #78). Exon 3 has 4 altered residues (or 2?). In exons 4 & 5 there are no differences apart from the 3 classification sites. Thus, there are 5 (or 7) unique AAs in zebrafish LL (255 AAs total), ignoring classification sites. Zebrafish LL is highly conserved compared to salmon LL, differing only by few percentage points.

Zebrafish LL (FIG. 16D,E) is closely similar to salmon LL. Zebrafish LL lacks one of six Cys seen in salmon LL, and thus may contain only two disulfide bridges: one connecting the N- and C-terminals, plus an internal bridge in exon 4. Comparing salmon and large zebrafish LL (FIG. 16E), the stereotypical structural variations seen in salmon are reinforced by the zebrafish LL structure. One radical difference is observed (residue #131), but mostly conserved substitutions are seen where variations in salmon LL occur. In PVF, LL may have immunoprotective functions. Restricted variations in LL structure may relate to such functions. The truncated leukolectin (tLL) lacks the secretory peptide, suggesting that tLL (FIG. 16D) is not secreted, and tLL may be a 4-bladed β-propeller protein. Different LL-proteins may in theory perform different cellular functions. The function of tLL may function in cells other than lectocytes.

EXAMPLE 10

Isolation and Characterisation of LL Gene from Salmon

Screening of BAC Library

To obtain the genomic structure of the leukolectin gene, we screened a public salmon genomic BAC library (18× coverage,average insert size about 188 kb) made available by the Salmon Genome Project (Oslo, Norway). Highly redundant bacterial artificial chromosome (BAC) library constructed from a Norwegian aquaculture strain of male Atlantic salmon (Salmo Salar) was screened for LL positive clones. The library consists of a total number of 305,557 clones. The average insert size of the library is 188 kbp, representing 18 fold genome coverage. CHORI-214 High density filters Seg. 1 (filter set-007193), each consisting of 18,432 clones spotted in duplicates, have been produced for hybridization screening.

To screen the library, a 620 bp LL-specific cDNA probe was prepared by incorporating digoxigenin-11-dUTP (Roche) by PCR method, using Forward primers LL/F 5'-TACGGACACAGGTCGAATCCCCTACTACC-3' (SEQ ID NO:31) and reverse primer LL/R 5'-ACAGAGAAGAG-GCTAATGTGTGCAC-3' (SEQ ID NO:32). DIG-labelled cDNA probe was incubation at 95° C. for 10 min. and immediately placed in the ice for 5 min before addition to the hybridisation buffer (5×SSC, 50% formamide, 0.02% SDS, 2% Blocking agent (Roche), DEPC-treated water).

Hybridization was carried out in hybridisation tubes at 55° C. overnight. Post-hybridisation washing step was performed twice at low stringency in 2×SSC with 0.1% SDS at RT for 15 min each, and twice at high stringency in 0.1×SSC with 0.1% SDS at 65° C. for 20 min each. The filters were incubated in a blocking solution containing Maleic acid buffer (pH 7.5) and 1% blocking reagent (Roche), and subsequently in blocking solution with anti-Dig-alkaline phosphatase (AP) conjugated antibody (Roche) diluted 1:10,000 for 1 h at RT. After washing with 0.1M Maleic acid buffer (pH 7.5) containing 150 mM NaCl and 0.5% Tween 20, the membrane was equilibrated for 2 min in detection buffer (0.1 M TrisHCl, 0.1 M NaCl, pH 9.5 at RT). Positive duplicated spots were visualised by chemiluminescent assay using CSPD (Roche) as a substrate. Identification of positive signals was achieved by exposing the filters to X-ray film (Kodak). Exposure time varied from 3 to 15 min. Two elected positive clones L-7/257 and A-12/144 were plated on prepared agar plates and incubated at 37° C. overnight. Three clones were picked, grown overnight in a 5 ml shaking culture in LB medium at 37° C. with 20 μg/ml chloramphenicol. Plasmid DNA purification was performed the next day using ultrapure DNA purification kit (Qiagen). BAC DNA was digested with Not I and analyzed by Pulse Field electrophoresis (PFGE)(Osoegawa et al., 1998, Genomics, 52, pp. 1-8). Low Range PFG Marker (New England Biolabs) and λ-Hind III fragment (Takara) were used as DNA size markers.

PCR Verification of Positive Clones

PCR reactions were carried out using purified BAC DNA as a template and gene specific primers. The PCR reactions were incubated at 95° C. for 3 min, followed by 35 cycles at 95° C. for 30 s, annealing at 54° C. for 30 s, and extension at 72° C. for 30 s with a final incubation at 72° C. for 10 min After thermocycling, 2 μl of each PCR reaction was analyzed on a 1.5% agarose gel.

Shotgun Sequencing of Leukolectin BAC Clones

Two clones were sequenced by MRW, Berlin, Germany. The vector inserts were sequenced to an estimated redundancy of 2.4 fold. Reads were cleaned of vector and host elements. From the around 180 reads, a total of respectively 33 and 22 contigs were established from the two BAC clones using bioinformatics. Contigs were examined both by mRNA sequences and by amino acid sequences. Analysis identified exons and introns, both by program searches and by manual inspections. The entire LL gene was identified from overlapping contigs.

Genomic Structure

The results of the above screen identified 7 specific clones named A-12/144, L-16/143, P-6/76, B-5/70, 0-20/85, L-7/257 and F-7/176 according to the BAC library nomenclature. The mean insert size of the genomic BAC clones was estimated from DNA purified from all selected BAC clones, which subsequently was digested with Not I restriction enzyme. The DNA digestion products containing vector were separated by pulse field gel electrophoresis and visualized by ethidium bromide stain. All BAC clones produced only two bands, showing that the vector (pTARBAC2.1) size was ~13 kbp (13,397 bp; Osoegawa et al., 1998, supra). This suggests that the insert size of all clones was ~25 kbp. The sequences of six of the 7 selected BAC clones were verified once more by amplification using as a template DNA purified from a BAC clone, together with LL gene-specific primers. PCR amplification gave a product of ~600 bp from all of these clones. Their identity was further confirmed by direct sequencing.

Shotgun Sequencing of Two BAC Clones

The sequence assembly programs BioEdit and Dna Baser were used on all sequence data. The analysis revealed that both isolated 25 kbp BAC clones contained the complete leukolectin mRNA sequence (after elimination of vector sequence elements), when screened against both mRNA sequences and protein sequences. The data from one of the BAC clones yielded a total of 80 reads, which were assembled in 33 contigs. Of these, at least 6 contigs contained LL-sequences, which allowed the reconstruction of the entire LL gene. In addition to LL sequences, other components were frequently identified in these contigs with a high degree of certainty, and included reverse transcriptase, ionic peptidase and transposable elements.

Features of the LL Genomic Gene Structure

In the first analysis only one of the clones (L7/247) allowed identification of an entire LL-gene, while the other clone (A12/144) revealed most of the genomic structure (see FIG. 16). The data from the genomic clone L7/247 suggested a genomic organization of leukolectin where the gene is composed of 5 exons interrupted by 4 introns, and spans ~2.3 kbp starting from the TATA-box. The genomic LL sequences revealed a TATA box starting at position −81 (TATAAAA) from ATG start codon, indicating an 81 nt 5'UTR (untranslatable element) of the mRNA. The stop codon TAG is located at approximately 1850 nt from ATG in the genomic sequence. A 6 nt long polyadenylation signal AATAAA starts around position 2,250 from ATG. The 3'UTR is a sequence about 400 nt long starting after the stop codon TAG. With a 5'UTR consisting of 81 nts, the LL-gene size is estimated to at least ~2.3 kbp by conventional definitions, with introns accounting for twice as much sequence as exons. In order to verify the exon-intron boundaries of the leukolectin gene, PCR primers were designed from the established genomic intron sequences, and used to amplify each exon from salmon embryonic DNA. These 5 exon sequences were derived by direct sequence analysis of amplicons, and all corresponded to the established genomic sequences.

The sizes of coding exons appeared to be quite unambiguous, and varied between 55 bp (Exon 1) and 234 bp (Exon 2). Notably, two introns were relatively small so that an exact length could be derived from manual reading of the data. In contrast, intron 3 is around 250 nt, while intron 4 spans around 700 bp. The exact length of intron 4 could not be defined from available data. The composite exon sequence data confirm the predicted product of translation, namely a 255 AA protein.

Furthermore, the data support a genomic LL gene structure with 5 exons and 4 introns for one of the two described variants of leukolectin. The N-terminal AA residue of secreted LL protein has been established to be tryptophan by direct Edman degradation of purified LL. This Trp-residue occupies position #20 from the N-Terminal methionine in the 255 AA precursor protein, and is preceded by amino acids #18 (His) and #19 (Ala). A cleavage site is predicted between Ala and Trp for a processing protease, to generate the secreted LL protein. By direct Edman degradation, the sequence of this secreted LL has established as WDCQE VVNIK NLMQI DAGLG Q-V (SEQ ID NO:33), and also verified by multiple virtual protein sequences. Exons are not all in-frame, but do potentially allow some exon skipping without disrupting all reading frames. The genomic sequence analysis indicated the sequences of the exon/intron boundaries. The exception is intron 4 where possibly nonstandard nts flank the intron sequences. In introns 1, 2 and 3, we found the common GT//AG feature flanking the beginning and the end of many vertebrate introns (Shapiro and Senepathy, 1987, Nucleic Acids Research, 15, pp. 7155-7174).

Exon 1 (19 AAs) is 55 nt long, with the sequence MRATA-AVLLV-LCLLT-ISH(A) (SEQ ID NO:34) and stops at the first G of codon for Ala #19 residue preceding the N-terminal tryptophan of the secreted leukolectin. The large R in bold italics signifies a variant AA in this position possibly tied to a Leukolectin-3 gene (see FIG. 17). The genomic gene sequence continues with the nucleotides GT to start intron 1. Intron 1 ends with the nucleotides AG followed by exon II, which contains the last two bases (−CA) of the #19 Ala codon followed by the TGG codon for #20 Trp, the N-terminal of leukolectin. Intron 1 is 89 nt long.

Exon 2 (234 nts) contains 77 AA (234−2 nts/3=77 AA+1 nt). Here, the genomic sequence translates (ala)—WDC-QEVVNIK-NLMQI DAGLG-QVVAT DTSQI-PYYLV G*DKWI-RL*GS LKHIT-VGPAG IWGVN-KDYAI YKYVA-GNWVQAA (G) (SEQ ID NO:35) (=77 AAs+1 nt) before continuing with the nucleotides GT (in intron 2). The asterisk denotes a residue where alternative AAs are found either in the LL protein or in multiple sequences of LL cDNA (see FIG. 17). G* appears to vary in Leukolectin-1, while L* appears to vary in leukolectin-2. Intron 2 is 186 nts long, ending in the nucleotides AG.

Exon 3 (72 AAs) starts after 2 nucleotides with GC (=Gly, residue #78) and continues for another 216 nts (for a total of 218 nts) or 72 AAs. The amino acid sequence of Exon 3 reads: (G)LL*KQL DAGGE-QFIVG ANMN*D TPYCLTSSAT-VGYKG PGSPL-PWTGL PGAVK-YYSCG P*FGCW-AVNKN DDIYL-MS (SEQ ID NO:36), where the residue #150 is S. Three large letters, in bold and underlined, signify variant AAs which serve to distinguish between leukolectin-1 and leukolectin-2. Letters with asterisk again signifies residues with micro-variation (N* in leukolectin-2; P* signifies micro-variation in both leukolectin-1 and leukolectin-2) at such a position (see FIG. 17). Intron 3 follows, starting with the nucleotides GT, and continues for another ~250 nts.

Exon 4 (39 AAs) starts at AA residue #151=LNQDC QNKGW-SHIE*G KLSMI-EVATD GSVFG-VNSA*GSVYT (SEQ ID NO:37), where T is residue #189. Again residue underlined in bold serves to distinguish leukolectin-1 from leukolectin-2, while an asterisk signifies micro-variation at this position (seen in either leukolectin at position E*, and only in leukolectin-2 for position A*). Intron 4 may possibly not start and stop with standard nt-sequences for intron-definition. Data on intron 4 are thus somewhat preliminary, and hence the length of intron 4 is an estimate (~700 nts).

Exon 5 (47 AAs) starts with codon for R (=residue #190) and continues till a C-terminal histidine (residue #236), which is followed by a stop codon TAG, and the 3'UTR. The sequence reads: RDGIT-ASKPE-GTGWS-NIPMG*-MLMGHVTYDL-GRLWV-VSKSAV-TMVCT-H (SEQ ID NO:38), where an asterisk indicates micro-variation in this position in leukolectin-1. Letters in bold signify differences between leukolectin-1 and leukolectin-2. Letters in bold and italics signify the possibility of the existence of leukolectin-3. These data are summarized in FIG. 17.

EXAMPLE 11

Comparison of Leukolectin-1 Genomic Sequence to Leukolectin mRNA Sequences

With more than a dozen separate cloning and sequencing experiments of cDNA from salmon, the aligned sequences revealed that only at 7 positions are clear alternatives of different amino acid residues accommodated. The paucity of overall sequence variation, and the stereotypical limitation to such variations, is remarkable.

The genomic sequence from L-7/247 corresponds to leukolectin clones classified as leukolectin-1. The other sequenced cDNAs termed leukolectin-2, differ at the seven positions indicated. In addition to these positions, there are indications of some further variations in AA. This may suggest additional micro-heterogeneity of the two classified cDNAs, but the data may suggest the existence of a third category of LL cDNA, since for instance in position #226, we do find a tyrosine residue in some clones which was never observed in any leukolectin-1 or leukolectin-2 cDNA (FIG. 17).

A summary of observed variations is shown in FIG. 17. The two types of leukolectins are characterized by respectively (E, I, Y, Y, K, A, V) versus (N, V, F, F, N, G, G) at the seven positions (#88, 91, 101, 147, 158, 229, 230) of the deduced AA sequence for the mature leukolectin. These 7 positions unambiguously classify these two leukolectins, which in addition may exhibit micro-variations at stereotypical positions shown by asterisks in FIG. 17. As the data in FIG. 17 indicate, some mRNA sequences point to a unique Gly in position #2 of the LL signal peptide which is not seen in leukolectins-1&2, and which therefore suggests a possible leukolectin-3. In addition, we have observed a Tyr at position #226 in the mature leukolectin where only Ser is seen in leukolectins-1&2. We conclude that the genomic sequence in L7/247 corresponds to leukolectin-1 sequences found by multiple sequencing of LL cDNA from salmon. Further sequencing of LL BAC clones should reveal the other main leukolectin-2 category, and perhaps also the suspected existence of leukolectin-3, as defined by the above residue-criteria.

The invention claimed is:

1. An isolated or purified polypeptide comprising (i) an amino acid sequence as set forth in any one of SEQ ID NOs:1-8, or (ii) an amino acid sequence having at least 95% sequence identity with an amino acid sequence as set forth in any one of SEQ ID NOs:1-8, wherein the polypeptide treats damaged skin in an animal and wherein the polypeptide is:
    (a) deglycosylated relative to the naturally-occurring protein; or
    (b) a recombinant or synthetic polypeptide prepared by culturing a prokaryotic host cell or an insect host cell containing a nucleic acid molecule encoding the polypeptide under conditions whereby the polypeptide is expressed and recovering the molecule thus produced.

2. A pharmaceutical composition comprising:
    (a) an isolated or purified polypeptide comprising (i) an amino acid sequence as set forth in any one of SEQ NOs:1-8, or (ii) an amino acid sequence having at least 95% sequence identity with an amino acid sequence as set forth in any one of SEQ ID NOs: 1-8, wherein the polypeptide treats damaged skin in an animal;
    (b) an effective amount of an added stabilizing agent, wherein the stabilizing agent stabilizes the polypeptide of (a) against degradation; and
    (c) one or more pharmaceutically acceptable excipients and/or diluents.

3. The isolated or purified polypeptide of claim 1, wherein said amino acid sequence has at least 96% sequence identity with an amino acid sequence as set forth in any one of SEQ ID NOs: 1-8.

4. The isolated or purified polypeptide of claim 1, wherein said amino acid sequence has at least 97% sequence identity with an amino acid sequence as set forth in any one of SEQ ID NOs: 1-8.

5. The isolated or purified polypeptide of claim 1, wherein said amino acid sequence has at least 98% sequence identity with an amino acid sequence as set forth in any one of SEQ ID NOs: 1-8.

6. The isolated or purified polypeptide of claim 1, wherein said amino acid sequence has at least 99% sequence identity with an amino acid sequence as set forth in any one of SEQ ID NOs: 1-8.

7. The isolated or purified polypeptide of claim 1, wherein said polypeptide comprises an amino acid sequence as set forth in any one of SEQ ID NOs:1-8.

8. The isolated or purified polypeptide of claim 1, wherein said damaged skin is irritated skin, inflamed skin, skin cracked by cold, sunburned skin, heat damaged skin or a wound.

9. The pharmaceutical composition of claim 2, wherein said composition is a gel, cream, ointment, lotion, foam, non-aqueous solution, spray, salve, stick, soap, powder, film, aerosol, emulsion, suspension, dispersion, tablet, pill, lozenge, sachet, cachet, syrup, capsule, suppository or solid implant.

* * * * *